Figure 5A:
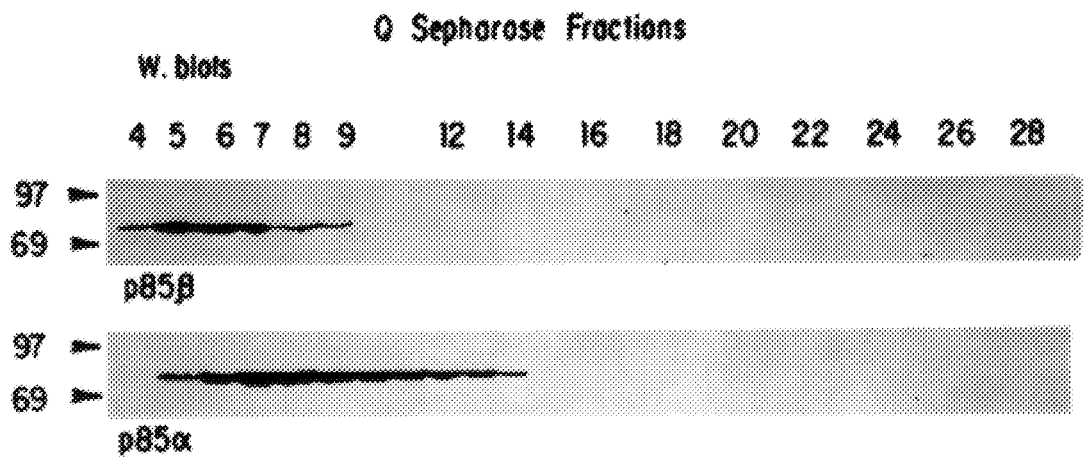

United States Patent [19]
Stephens et al.

[11] Patent Number: 5,859,201
[45] Date of Patent: Jan. 12, 1999

[54] G-BETA-GAMMA REGULATED PHOSPHATIDYLINOSITOL-3' KINASE

[75] Inventors: Len Stephens; Phillip Thomas Hawkins, both of Sawston, England

[73] Assignee: Onyx Pharmaceuticals, Richmond, Calif.

[21] Appl. No.: 972,629

[22] Filed: Nov. 18, 1997

Related U.S. Application Data

[62] Division of Ser. No. 672,211, Jun. 27, 1996.

[51] Int. Cl.$^6$ .............................. C12P 21/04; C07K 1/00
[52] U.S. Cl. ......................... 530/350; 530/829; 435/69.7
[58] Field of Search ........................... 435/69.7; 530/350, 530/829

[56] References Cited

FOREIGN PATENT DOCUMENTS

WO 96/12024 A 7/1996 WIPO.

OTHER PUBLICATIONS

Acaro et al., 1993, "Wortmannin is a Potent Phosphatidylinositol 3–Kinase Inhibitor: the Role of Phosphatidylinositol 3,4,5–triphosphate in Neutrophil Responses," *Biochem. J.* 296:297–301.

Chen et al., 1995, "A Region of Adenylyl Cyclase 2 Critical for Regular by G Protein βγ Subunits", *Science* 268:1166–1169.

Gura, 1996, "Chemokines Take Center Stage in Inflammatory Ills," *Science* 272:954–956.

Inukai et al., 1995, "A Novel 55–kDA Regulatory Subunit for Phosphatidylinositol 3–Kinase Structurally Similar to p55PIK Is Generated by Alternative Splicing of the p85α Gene", *J. Biol. Chem.* 271:5317–5320.

Kurosu et al., 1995, "Radiolabeling of Catalytic Subunits of PI 3–Kinases with 17β–Hydroxy–16α–[$^{125}$I]iodowortmannin: Identification of the Gβγ–Sensitive Isoform as a Complex Composed of 46–kDa and 100–kDa Subunits," *Biochem. Biophys. Res. Commun.* 216:655–661.

Morris et al., 1995, "Regulation of Phosphoinositide–3–Kinase by G Protein βγ–Subunits in a Rat Osteosarcoma Cell Line," *Molecular Pharmacology* 48:532–539.

Otsu et al., 1991, "Characterization of Two 85 kd Proteins That Associate with Receptor Tyrosine Kinases, Middle–T/pp50$^{c-src}$ Complexes, and PI3–Kinase", *Cell* 65:91–104.

Pons et al., 1995, "The Structure and Function of p55$^{PIK}$ Reveal a New Regulatory Subunit for Phosphatidylinositol 3–Kinase", *Mol. Cell. Biol.* 15:4453–4465.

Rodriguez–Viciana et al., 1994, "Phosphatidylinositol–3–Oh Kinase as a Direct Target of Ras," *Science* 370:527–532.

Schu et al., 1993, "Phosphatidylinositol 3–Kinase Encoded by Yeast VPS34 Gene Essential for Protein Sorting," *Science* 260:88–91.

Shaw et al., 1996, "The Plekstrin Homology Domain: An Intriguing Multifunctional Protein Module", *Bioassays* 18:35–46.

Songyang et al., 1993, "SH2 Domains Recognize Specific Phosphopeptide Sequences", *Cell* 72:767–778.

Staub et al., 1996, "WW Domains", *Structure* 4:495–499.

Stephens et al., Feb. 29, 1996, "A Heterotrimeric GTPase–Regulated Isoform of PI3K and the Regulation of its Potential Effectors" *Phil. Trans. R Soc. Lond. B* 351:211–215.

Stephens et al., Apr. 4, 1997, "The GBY Sensitivity of a PI3K is Dependent Upon a Tightly Associated Adaptor, p101," *Cell* 89:105–114.

Stephens et al., 1994, "A Novel Phosphoinositide 3 Kinase Activity in Myeloid–Derived Cells is Activated by G Protein βγ Subunits," *Cell* 77:83–93.

Stephens et al., 1991, "Pathway of Phosphatidylinositol(3,4,5)–Triphosphate Synthesis in Activated Neutrophis," *Nature* 351:33–38.

Stephens et al., 1993, "Agonist–Stimulated Synthesis of Phosphatidylinositol(3,4,5)–Triphosphate: A New Intracellular Signing System?," *Biochim. Biophys. Acta* 1179:27–75.

Stoyanov et al., 1995, "Cloning and Characterization of a G Protein–Activated Human Phosphoinositide–3 Kinase," *Cell* 269:690–693.

Thelan et al., 1994, "Wortmannin Binds Specifically to 1–Phosphatidylinositol 3–Kinase while Inhibiting Suanine Nucleotide–Binding Protein–Coupled Receptor Signaling in Neutrophil Leukoxytes,," *Proc. Natl. Acad. Sci., USA* 91:4960–4964.

(List continued on next page.)

Primary Examiner—Robert A. Wax
Assistant Examiner—Elizabeth Slobodyonsky
Attorney, Agent, or Firm—Pennie & Edmonds LLP; Gregory Giotta

[57] ABSTRACT

The present invention relates to the discovery, identification and characterization of nucleotides that encode the G protein regulated phosphatidylinositol-3' kinase, a heterodimeric enzyme which produces the intracellular messenger phosphatidylinositol (3,4,5)-triphosphate in response to activation of trimeric G protein-linked receptors. This novel protein, comprised of a catalytic subunit, p120, and a regulatory subunit, p101, is found in cells of hematopoietic origin and is involved in immune system responses which cause inflammation. The presence of p101 subunit is largely responsible for the dramatic stimulation of kinase activity in the presence of activated trimeric G proteins. The invention encompasses p101 and p120 nucleotides, host cell expression systems, p101 and p120 proteins, fusion proteins, polypeptides and peptides, antibodies to these proteins, transgenic animals that express a p101 or p120 transgene, or recombinant knock-out cells and animals that do not express the p101 or p120 gene, antagonists and agonists of the enzyme, and other compounds that modulate p101 or p120 gene expression or enzyme activity that can be used for diagnosis, drug screening, clinical trial monitoring, and/or the treatment of inflammatory disorders.

13 Claims, 14 Drawing Sheets

OTHER PUBLICATIONS

Thomason et al., 1994, "A G–Protein βγ–Subunit–Responsive Phosphoinositide 3–Kinase Activity in Human Platelet Cytosol," *J. Biol. Chem.* 269:16525–16528.

Touhara et al., 1994, "Binding of G Protein βγ–Subunits to Pleckstrin Homology", *J. Biol. Chem.* 269:10217.

Volinia et al., 1995, "A Human Phosphatidylinositol 3–Kinase Complex Related to the Yeast Vps34p–Vps15p Protein Sorting System," *EMBO J.* 14:3339–3348.

Yano et al., 1993, "Inhibition of Histamine Secretion by Wortmannin through the Blockade of Phosphatidylinositol 3–Kinase in RBL–2H3 Cells," *J. Biol. Chem.* 368:25846–25856.

```
   1  CCGTGCGCCC CTCAAGACTA ATGGACCCCC GGCTCAGGAA TCGCACGAGG
  51  CAGGCTCACA CCCGAGGCCC ATGGAAGTTC CCAGGCCAGG GGTCAAGTTG
 101  GAACCGAAGC TGCTGCCAGC TTACACCACA GCCACAGCAA CTTGGGATCT
 151  GAGCTGCATC TGTGACCTAC ACCACAGCTC ACGGCAATGC TGGATTCCCA
 201  ACACACCAAG TGGGGCCAGG GATCGAACCC GCATCCTCTT GGACAGTAGT
 251  CAGATTCATT ACCACTGAGC CATTGACAGG AACTCCAGGG GCAGGGGGGA
 301  GTCTCTTGTT TTTGGCTCCT CCCGACACCT GGTGAAATGG ACCAGCGCAG
 351  GCACCCCTTT CCAGTGGCTG TCCCAGGCGA TGACTCAGGA TGCAGCCAGG
 401  GGCCACGACG TGCACGGAGG ACCGCATCCA GCACGCCCTG GAGCGCTGCT
 451  TGCACGGGCT CAGCCTCAGC CGCCGCTCCA CCTCCTGGTC AGCTGGGCTG
 501  TGTCTAAACT GTTGGAGCCT GCAGGAGCTG GTCAGCAGGG ATCCGGGCCA
 551  CTTCCTTATC CTCCTGGAGC AGATCCTGCA GAAAACCCGA GAGGTCCAAG
 601  AGAAGGGCAC CTATGACCTC CTCGCGCCCC TGGCCCTGCT CTTCTATTCT
 651  ACTGTCCTCT GTACGCCACA CTTCCCGCCA GACTCAGATC TCCTTCTGAA
 701  AGCAGCCAGA ACCTACCACC GATTCCTGAC CTGGCCGGTT CCGTACTGCA
 751  GCATCTGCCA GGAACTGCTC ACCTTCATCG ATGCTGAGCT GAAGGCCCCA
 801  GGAATCTCCT ACCAGCGACT GGTGAGGGCG GAGCAGGGCC TGTCCACAAG
 851  GAGTCACCGC AGCTCCACCG TCACGGTGCT CTTGGTGAAC CCCGTGGAGG
 901  TGCAGGCTGA GTTCCTTGAC GTGGCCGACA AGCTGAGCAC ACCAGGGCCC
 951  TCGCCGCACA GCGCCTACAT CACCCTGCTC CTGCATGCCT TCCAGGCCAC
1001  CTTTGGGGCC CACTGTGACC TCTCTGGTCT GCACCGCAGG TTGCAGTCCA
1051  AGACCCTGGC AGAGCTCGAG GCCATCTTCA CGGAGACAGC CGAGGCACAG
1101  GAGCTGGCCT CAGGCATCGG GGATGCAGCT GAGGCCCGGC AGTGGCTCAG
1151  GACCAAGCTG CAGGCGGTGG GAGAGAAGGC CGGCTTCCCT GGTGTCTTAG
```

FIG.1A

```
1201  ACACCGCCAA  ACCTGGCAAG  CTCCGCACCA  TCCCCATCCC  GGTCGCCAGG
1251  TGCTACACCT  ACAGCTGGAA  CCAGGACAGC  TTCGACATCC  TGCAGGAAAT
1301  CCTGCTCAAG  GAGCAGGAGC  TGCTCCAGCC  AGAGATCCTG  GACGACGAGG
1351  AGGACGAGGA  CGAGGAGGAC  GAGGAAGAGG  ACTTGGACGC  CGACGGCCAC
1401  TGCGCGGAGA  GGGACTCCGT  GCTCTCCACC  GGCTCGGCGG  CCTCCCACGC
1451  CTCCACGCTG  TCCCTGGCCT  CGTCCCAGGC  CTCGGGGCCC  ACGCTCTCCC
1501  GCCAGTTGCT  GACCTCCTTC  GTCTCGGGCC  TCTCGGATGG  CGTGGACAGC
1551  GGCTACATGG  AGGACATCGA  GGAGAGCGCC  TACGAGCGGC  CCCGGAGGCC
1601  TGGCGGCCAC  GAGCGCCGGG  GCCACCGCCG  GCCCGGGCAG  AAGTTCAACA
1651  GGATCTATAA  ACTCTTCAAG  AGCACCAGCC  AGATGGTGCT  GCGGAGGGAC
1701  TCGCGCAGCC  TGGAGGGCAG  CCCGGACAGC  GGCCCGCCCC  TGCGTCGGGC
1751  CGGCAGCCTC  TGCAGCCCCC  TGGACAGCCC  GACCCTGCCC  CCGTCCCGGG
1801  CCCAGGGCTC  CCGCTCGCTG  CCCCAGCCCA  AGCTCAGCCC  CCAGCTGCCC
1851  GGCTGGCTCC  TGGCCCCCGC  CTCCCGCCAC  CAGCGCCGCC  GCCCCTTCCT
1901  GAGCGGGGAC  GAGGACCCCA  AGGCTTCCAC  GCTGCGTGTC  GTGGTCTTCG
1951  GCTCGGATCG  GATCTCGGGG  AAGGTGGTCC  GGGCTTACAG  CAACCTGCGG
2001  CGGCTGGAGA  ACAACCGTCC  TCTCCTCACA  CGGTTCTTCA  AGCTACAGTT
2051  CTTCTACGTG  CCTGTCAAGC  GGAGCCGTGG  GACAGGCACC  CCCACCAGCC
2101  CAGCCCCTCG  GAGCCAGACG  CCCCCCCTCC  CCACAGACGC  CCCGAGGCAC
2151  CCGGGCCCTG  CAGAGCTGGG  CGCCGCCCCC  TGGGAGGAGA  GCACCAATGA
2201  CATCTCCCAC  TACCTCGGCA  TGCTCGACCC  CTGGTACGAG  CGAAACGTCC
2251  TGGGCCTCAT  GCACCTGCCT  CCTGAAGTCC  TGTGCCAGTC  CCTGAAGGCT
2301  GAGCCCCGGC  CCCTGGAGGG  CTCCCCTGCC  CAGCTGCCCA  TCCTGGCGGA
2351  CATGCTGCTC  TACTACTGCC  GCTTCGCTGC  CCGGCCGGTG  CTGCTGCAGG
2401  TCTATCAGAC  CGAGCTGACC  TTCATCACCG  GGGAGAAGAC  GACGGAGATC
2451  TTCATCCACT  CCCTGGAGCT  GGGCCACTCT  GCTGCCACAC  GTGCCATCAA
2501  GGCTTCGGGT  CCTGGCAGCA  AGCGGCTGGG  CATCGATGGT  GACCGGGAGG
```

FIG.1B

```
2551  CCGTCCCTCT  AACACTACAG  ATAATTTACA  GCAAGGGGGC  CATCAGCGGC
2601  CGGAGTCGCT  GGAGCAACAT  GGAAAAGCTC  TGCACCTCTG  TCAACCTCAG
2651  CAAGGCCTGC  CGGCAGCAGG  AGGAGCTAGA  CTCCAGCACA  GAGGCCCTGA
2701  CGCTAAACCT  GACAGAAGTG  GTGAAAAGAC  AGACCCCTAA  ATCCAAGAAG
2751  GGCTTTAACC  AGATCAGCAC  CTCGCAGATC  AAAGTGGACA  AGGTGCAGAT
2801  CATCGGCTCT  AACAGCTGCC  CCTTTGCCGT  GTGTCTGGAC  CAGGACGAGA
2851  GGAAGATCCT  GCAGAGTGTC  ATCAGGTGCG  AGGTCTCGCC  CTGCTACAAG
2901  CCTGAGAAGA  GCAGCCTCTG  CCCCCCACCC  CAGAGGCCCT  CCTACCCGCC
2951  AGCGCCGGCC  ACGCCCGACC  TCTGCTCCCT  GCTCTGCCTG  CCCATCATGA
3001  CTTTCAGCGG  AGCTCTGCCC  TAGCCGCCAC  CCTGCACCAG  CCTGGACAGG
3051  GAGCCGGGGG  GCAGCCTCCT  CGGAGCCCCC  TCCCCAGAAG  ACTGGCGGCT
3101  GAGAGGGTCG  TGCTCCCTGT  GGAGAACAGA  GGGGCCGTGT  ACTGGGTCAG
3151  GGTCCCGCTG  TGGGCCCTGC  AGCAGCAAGA  GCGGGGGCTG  CTGGGGCCTC
3201  AGGGCTCTGT  TTGGGCGAGA  AGCAGGCATT  AGGGAGAGGG  GCCTGGCCCC
3251  ACGGCTCTCA  GCTTCCTCAC  GGTAGCGGAG  AGAGGGATGG  GTGAGCTTGA
3301  CCTCAAGGCC  CTGGCCTCCA  GTGGGGGTCC  AGGATCCTTT  CTGGAAGGAA
3351  GATCCCAAGG  CGCTGGTGCT  CTGGGGTGTG  GTGTTAGGGG  CTCCCCCCCC
3401  AGCCCTGGGC  CAGGGCCCCC  CCGTTACTTT  GTCAGAGACT  TGGGGATCCT
3451  GTGTCTGGAG  GGTCAAGTCC  CCCTCCCTGG  GGGTTCAAGC  AGTGGAAGTA
3501  TGGTTGCGAC  TTTTCTGACG  TTGGTGCAAT  CCCCGCCCCC  ACCTCAACCC
3551  CCCCACAAAA  AAACCCCTTC  TCTCTTTCAA  GTTCCCTGGG  TCTTCTGTGA
3601  AACAGCACTA  ACACTTGACC  TGGCTGTGCC  AGCACTTGGA  ACAGATGCTC
3651  CCTGGATCGA  GAGCCTTGGG  AGACAGGACA  AGCTTAGGTT  CGGTGGTGGC
3701  TCAGTTACCT  TCTAGCGAAA  TGAGCAGAAG  GAGGTGAATT  GGCTCCTTCG
3751  AGGCTCCCCT  ACCTGGGCAC  TAAGATGGGG  GGAATAAGGC  CGCCTTAAAG
3801  GGTTGGGGTG  ATGTCGTCTG  CAAAGCGCCT  GGCCCAGTGG  CCGGCTGGTA
3851  GCAAGGTGCG  GCCTCACCCT  CTGGGCGTCG  ACTCCCTCGT  GTGGCGGGAG
```

FIG. 1C

| | | | | |
|---|---|---|---|---|
| 3901 | GCTAAAAGGA | TGCCCTGCCC | CCGTGATGCT | GTCATTCCCT | CCTTCCAATT |
| 3951 | CACTGATGAG | GCAGGACCCA | GACTGAGGGG | GTGAGGGGCG | CACAGTTCTA |
| 4001 | CCTTTGAAGG | AGGAAGTGCC | TTGATCAGAG | TAAGAGGAGG | GTGGCCCAGG |
| 4051 | CGCCCCCAAC | CGCCCCCTCC | TCCTCTCCCA | GGTTGGCCCC | TGTGCCTCCC |
| 4101 | ACTCCCATCT | CACTCCTTGG | GCTGGCGCAC | ATCACGGGCA | CAGTCCTCCA |
| 4151 | GCCCCACAGT | TCACTGGTAC | CATGGCCCCT | GGGTCGGTTC | GCAGAGGATG |
| 4201 | GAGGATAAGA | CTTGCCTCGA | GAACTTGGGT | CTGATGGGGA | AACCGGGTGA |
| 4251 | TGGAAATGAT | TCCGGAAGAT | TAAAACCTCC | CAGGTTCAAG | TGTCGGAGAA |
| 4301 | CCGCCCCCAC | AACCGGACTA | GGTTGGTAGG | GAGAGGGCAG | GGCTTGGGCC |
| 4351 | CGGGATTTGG | ACTAGGAGAG | GCGGGGGGAG | GTAACCAGAG | AAgCAAGACA |
| 4401 | GTTGTATCCC | CGCAAAAGAC | CCTTCCCCGC | CCCTCCCCTC | CTGCTCTGGC |
| 4451 | TCCATCTGCT | TCAAAGGGTC | TGGGCTTTAG | GAGCCCGTGG | TGCCCAGCGC |
| 4501 | AGCGTACTCA | GGACTCGAGA | GACGCGGACC | GTGCCAGTTC | CCACCCTGTG |
| 4551 | CCACTCCAGG | CCCCAGGGAG | GGGTTTGCAA | TATACCCTCA | ACGTTTTTGT |
| 4601 | GTGTGTGGTA | AGGTCGTCCT | AGGACCCcAA | ATGGAATTTA | ACGTTATTGT |
| 4651 | CAAATAAAAC | TTGATTTGTC | TTGGAAAAAA | AAAAAAAAAA | AA |

FIG. 1D

| | | | | |
|---|---|---|---|---|
| 1 MQPGATTCTE | DRIQHALERC | LHGLSLSRRS | TSWSAGLCLN | CWSLQELVSR |
| 51 DPGHFLILLE | QILQKTREVQ | EKGTYDLLAP | LALLFYSTVL | CTPHFPPDSD |
| 101 LLLKAARTYH | RFLTWPVPYC | SICQELLTFI | DAELKAPGIS | YQRLVRAEQG |
| 151 LSTRSHRSST | VTVLLVNPVE | VQAEFLDVAD | KLSTPGPSPH | SAYITLLLHA |
| 201 FQATFGAHCD | LSGLHRRLQS | KTLAELEAIF | TETAEAQELA | SGIGDAAEAR |
| 251 QWLRTKLQAV | GEKAGFPGVL | DTAKPGKLRT | IPIPVARCYT | YSWNQDSFDI |
| 301 LQEILLKEQE | LLQPEILDDE | EDEDEEDEEE | DLDADGHCAE | RDSVLSTGSA |
| 351 ASHASTLSLA | SSQASGPTLS | RQLLTSFVSG | LSDGVDSGYM | EDIEESAYER |
| 401 PRRPGGHERR | GHRRPGQKFN | RIYKLFKSTS | QMVLRRDSRS | LEGSPDSGPP |
| 451 LRRAGSLCSP | LDSPTLPPSR | AQGSRSLPQP | KLSPQLPGWL | LAPASRHQRR |
| 501 RPFLSGDEDP | KASTLRVVVF | GSDRISGKVV | RAYSNLRRLE | NNRPLLTRFF |
| 551 KLQFFYVPVK | RSRGTGTPTS | PAPRSQTPPL | PTDAPRHPGP | AELGAAPWEE |
| 601 STNDISHYLG | MLDPWYERNV | LGLMHLPPEV | LCQSLKAEPR | PLEGSPAQLP |
| 651 ILADMLLYYC | RFAARPVLLQ | VYQTELTFIT | GEKTTEIFIH | SLELGHSAAT |
| 701 RAIKASGPGS | KRLGIDGDRE | AVPLTLQIIY | SKGAISGRSR | WSNMEKLCTS |
| 751 VNLSKACRQQ | EELDSSTEAL | TLNLTEVVKR | QTPKSKKGFN | QISTSQIKVD |
| 801 KVQIIGSNSC | PFAVCLDQDE | RKILQSVIRC | EVSPCYKPEK | SSLCPPPQRP |
| 851 SYPPAPATPD | LCSLLCLPIM | TFSGALP* | | |

FIG.2

```
   1 GGCACGAGGA  ATTTGTTTTG  TTTTCAGAAA  TTAAACAAAT  GATCCTTCAG
  51 CATCATCACC  TCCGCTGCTT  TATCAGGTCG  CATAGGGCAT  GGAGCTGGAG
 101 AACTATGAAC  AGCCCGTGGT  GCTGAGAGAG  GACAACCGCC  GCAGGCGTCG
 151 GAGGATGAAG  CCGCGCAGCA  CGGCAGCCAG  CCTGTCCTCC  ATGGAGCTCA
 201 TCCCCATCGA  GTTTGTTTTG  GCCACCAGCC  AGCGCAACAC  CAAGACCCCC
 251 GAAACGGCAC  TGCTGCACGT  GGCCGGCCAC  GGCAATGTGG  AGAAGATGAA
 301 GGCCCAGGTG  TTGTTGCGCG  CGCTGGAGAC  GAGCGTTTCT  TGGGACTTCT
 351 ACCACCGGTT  CGGCCCCGAC  CACTTCCTCC  TGGTCTTCCA  GAAGAAGGGG
 401 GAGTGGTACG  AGATCTATGA  CAAGTACCAG  GTGGTGCAGA  CCCTGGACTG
 451 CCTGCGCTAC  TGGGAGGTGT  TGCACCGCAG  CCCCGGGCAG  ATCCACGTGG
 501 TCCAGCGGCA  CGCGCCCTCG  GAGGAGACAT  TGGCCTTCCA  GCGCCAGCTC
 551 AACGCCCTCA  TCGGCTACGA  CGTCACCGAC  GTCAGCAACG  TGCATGACGA
 601 TGAGCTGGAG  TTCACGCGGC  GCCGCCTGGT  CACCCCGCGC  ATGGCCGAGG
 651 TGGCCGGCCG  CGACCCCAAG  CTTTACGCCA  TGCACCCCTG  GGTGACATCC
 701 AAGCCCCTCC  CTGAGTACCT  TCTGAAGAAG  ATCACTAACA  ACTGCGTCTT
 751 CATCGTCATT  CACCGCAGCA  CCACCAGCCA  GACCATCAAG  GTCTCGGCCG
 801 ATGACACCCC  AGGCACCATC  CTCCAGAGCT  TCTTTACCAA  GATGGCCAAG
 851 AAGAAATCTC  TGATGGATAT  CCCTGAAAGC  CAGAACGAAC  GGGACTTTGT
 901 GCTGCGCGTC  TGCGGCCGGG  ATGAGTACCT  GGTGGGTGAG  ACGCCCATCA
 951 AAAATTTCCA  GTGGGTGAGG  CAGTGCCTCA  AGAATGGGGA  GGAGATTCAC
1001 CTTGTGCTGG  ACACTCCTCC  AGACCCAGCC  CTGGACGAGG  TGAGGAAGGA
1051 AGAGTGGCCG  CTGGTGGATG  ACTGCACGGG  AGTCACTGGC  TACCACGAGC
1101 AGCTGACCAT  CCACGGCAAG  GACCATGAAA  GTGTGTTCAC  CGTGTCCCTG
1151 TGGGACTGTG  ACCGCAAGTT  CAGGGTCAAA  ATCAGAGGCA  TTGATATCCC
```

FIG.3A

```
1201  TGTCCTGCCC  CGGACCGCTG  ACCTCACGGT  GTTTGTGGAG  GCAAACATCC
1251  AGTATGGGCA  GCAAGTCCTT  TGCCAAAGGA  GAACCAGCCC  CAAACCCTTC
1301  ACGGAGGAGG  TGCTCTGGAA  CGTGTGGCTT  GAGTTCAGTA  TTAAAATCAA
1351  AGACTTACCC  AAAGGGGCTC  TGCTGAACCT  CCAGATCTAC  TGCGGCAAAG
1401  CTCCAGCACT  GTCTGGCAAG  ACCTCTGCAG  AGATGCCCAG  TCCCGAGTCC
1451  AAAGGCAAAG  CTCAGCTTCT  GTACTATGTC  AACCTATTGC  TGATAGACCA
1501  CCGCTTCCTC  CTGCGCCATG  GCGAGTATGT  GCTCCACATG  TGGCAGTTAT
1551  CCGGGAAGGG  GGAAGACCAA  GGGAGCTTCA  ATGCCGACAA  GCTCACGTCG
1601  GGAACCAACC  CGGACAAGGA  GGACTCAATG  TCCATCTCCA  TTCTTCTGGA
1651  CAATTACTGC  CACCCCATAG  CCTTGCCTAA  GCATCGGCCT  ACCCCTGACC
1701  CAGAAGGGGA  CCGGGTTCGG  GCAGAAATGC  CCAATCAGCT  TCGGAAGCAA
1751  CTGGAGGCAA  TCATAGCCAC  GGATCCGCTT  AACCCACTCA  CAGCTGAAGA
1801  CAAAGAACTG  CTCTGGCATT  TCAGATATGA  AAGCCTGAAG  GATCCCAAAG
1851  CGTATCCTAA  GCTCTTTAGC  TCGGTGAAAT  GGGGACAGCA  AGAAATTGTG
1901  GCCAAAACAT  ACCAATTATT  AGCCAAAAGG  GAGGTCTGGG  ATCAGAGTGC
1951  TTTGGATGTG  GGGTTAACCA  TGCAGCTCCT  GGACTGCAAC  TTCTCGGATG
2001  AAAACGTGAG  AGCCATTGCA  GTCCAGAAAC  TGGAGAGCTT  GGAGGATGAT
2051  GACGTGCTCC  ATTACCTGCT  CCAGCTGGTC  CAGGCTGTGA  AATTTGAACC
2101  ATACCATGAC  AGTGCCCTAG  CCAGATTTCT  GCTGAAGCGT  GGTTTAAGAA
2151  ACAAGAGAAT  TGGTCACTTC  TTGTTTTGGT  TCTTGAGAAG  TGAGATTGCC
2201  CAGTCTAGGC  ACTATCAGCA  GAGGTTTGCA  GTGATCCTGG  AAGCCTACCT
2251  GAGGGGCTGT  GGCACAGCCA  TGCTGCACGA  CTTCACCCAG  CAAGTCCAAG
2301  TAATTGACAT  GTTACAAAAA  GTCACCATTG  ACATTAAATC  GCTCTCTGCT
2351  GAAAAGTATG  ACGTCAGTTC  CCAAGTTATT  TCCCAACTTA  AGCAAAAGCT
2401  TGAAAACCTA  CAGAATTTGA  ATCTCCCCCA  AAGCTTTAGA  GTTCCCTATG
2451  ATCCTGGACT  GAAAGCCGGG  GCACTGGTGA  TCGAAAAATG  TAAAGTGATG
2501  GCCTCCAAGA  AGAAGCCCCT  GTGGCTTGAG  TTTAAATGTG  CCGATCCTAC
```

FIG. 3B

```
2551  GGCTCTATCA  AATGAAACAA  TTGGAATTAT  CTTTAAACAC  GGTGACGATC
2601  TGCGCCAAGA  CATGCTTATT  TTACAGATTC  TACGAATCAT  GGAGTCCATT
2651  TGGGAGACCG  AATCTTTGGA  TCTGTGCCTC  CTGCCATATG  GCTGCATTTC
2701  AACTGGTGAC  AAAATAGGAA  TGATCGAGAT  CGTGAAGGAC  GCCACGACAA
2751  TCGCCAAAAT  TCAGCAAAGC  ACAGTGGGCA  ACACGGGTGC  CTTTAAAGAT
2801  GAAGTCCTGA  GTCACTGGCT  CAAAGAAAAA  TGCCCTATTG  AAGAAAAGTT
2851  TCAGGCAGCT  GTGGAGAGAT  TTGTTTATTC  CTGTGCCGGC  TACTGTGTGG
2901  CAACCTTTGT  TCTCGGAATA  GGCGACAGAC  ACAATGACAA  TATTATGATC
2951  TCAGAAACAG  GAAATCTATT  TCATATTGAT  TTCGGACACA  TTCTTGGGAA
3001  TTACAAAAGT  TTCCTGGGCA  TTAATAAAGA  GAGGGTGCCA  TTTGTGCTAA
3051  CCCCAGACTT  CCTGTTTGTG  ATGGGGACTT  CTGGAAAGAA  GACAAGTCTA
3101  CACTTCCAGA  AATTTCAGGA  TGTCTGCGTC  AAGGCTTACC  TAGCCCTTCG
3151  TCATCACACA  AACCTACTGA  TCATCCTCTT  CTCCATGATG  CTGATGACAG
3201  GAATGCCCCA  GTTAACCAGC  AAAGAAGACA  TTGAATACAT  TCGGGATGCC
3251  CTCACAGTGG  GCAAAAGTGA  GGAGGATGCT  AAAAAGTATT  TTCTGGATCA
3301  GATTGAAGTT  TGCAGAGACA  AAGGATGGAC  CGTGCAGTTT  AACTGGTTCT
3351  TACATCTTGT  TCTTGGCATC  AAACAAGGGG  AGAAGCATCC  CGCATAAAAC
3401  TTTGGGCCAA  GAGTTAAAAC  CCAAGTTATT  GTCCTAATGC  TTTACGTCAG
3451  CAGGACAATC  ACCGAACTTG  ATGTCATGTA  GTGGGACATT  ATGAAAGCTG
3501  GCACTTGAGA  AATATAGCTC  TTCCCCTAAC  TGAACTCTTC  ACTGGAGAAA
3551  AACCTTGGCA  TGTTTAAGTA  ATGTTCAGTG  TTAGGCTTAT  TTGCATGTTT
3601  GTTTTTTCTC  ATGTGCCCCC  TCAGTCATGT  TGGAGACTGT  TCTAAATTTA
3651  AGTGGCCTAA  TGACCTCTGA  AGTTTCAACT  TTCTTGGTAC  TGAGTGCTTC
3701  TGAAATTCTT  TACAATAATT  GGTAACATCT  ATTGTCAGCT  GGGTATCCTC
3751  TCAATTTTGG  TTATCCTTGG  GTTTCTCAAA  CTCCTTACAG  GAAAAAAAAA
3801  AAAAAAAA
```

FIG.3C

```
   1  MELENYEQPV  VLREDNRRRR  RRMKPRSTAA  SLSSMELIPI  EFVLATSQRN
  51  TKTPETALLH  VAGHGNVEKM  KAQVLLRALE  TSVSWDFYHR  FGPDHFLLVF
 101  QKKGEWYEIY  DKYQVVQTLD  CLRYWEVLHR  SPGQIHVVQR  HAPSEETLAF
 151  QRQLNALIGY  DVTDVSNVHD  DELEFTRRRL  VTPRMAEVAG  RDPKLYAMHP
 201  WVTSKPLPEY  LLKKITNNCV  FIVIHRSTTS  QTIKVSADDT  PGTILQSFFT
 251  KMAKKKSLMD  IPESQNERDF  VLRVCGRDEY  LVGETPIKNF  QWVRQCLKNG
 301  EEIHLVLDTP  PDPALDEVRK  EEWPLVDDCT  GVTGYHEQLT  IHGKDHESVF
 351  TVSLWDCDRK  FRVKIRGIDI  PVLPRTADLT  VFVEANIQYG  QQVLCQRRTS
 401  PKPFTEEVLW  NVWLEFSIKI  KDLPKGALLN  LQIYCGKAPA  LSGKTSAEMP
 451  SPESKGKAQL  LYYVNLLLID  HRFLLRHGEY  VLHMWQLSGK  GEDQGSFNAD
 501  KLTSGTNPDK  EDSMSISILL  DNYCHPIALP  KHRPTPDPEG  DRVRAEMPNQ
 551  LRKQLEAIIA  TDPLNPLTAE  DKELLWHFRY  ESLKDPKAYP  KLFSSVKWGQ
 601  QEIVAKTYQL  LAKREVWDQS  ALDVGLTMQL  LDCNFSDENV  RAIAVQKLES
 651  LEDDDVLHYL  LQLVQAVKFE  PYHDSALARF  LLKRGLRNKR  IGHFLFWFLR
 701  SEIAQSRHYQ  QRFAVILEAY  LRGCGTAMLH  DFTQQVQVID  MLQKVTIDIK
 751  SLSAEKYDVS  SQVISQLKQK  LENLQNLNLP  QSFRVPYDPG  LKAGALVIEK
 801  CKVMASKKKP  LWLEFKCADP  TALSNETIGI  IFKHGDDLRQ  DMLILQILRI
 851  MESIWETESL  DLCLLPYGCI  STGDKIGMIE  IVKDATTIAK  IQQSTVGNTG
 901  AFKDEVLSHW  LKEKCPIEEK  FQAAVERFVY  SCAGYCVATF  VLGIGDRHND
 951  NIMISETGNL  FHIDFGHILG  NYKSFLGINK  ERVPFVLTPD  FLFVMGTSGK
1001  KTSLHFQKFQ  DVCVKAYLAL  RHHTNLLIIL  FSMMLMTGMP  QLTSKEDIEY
1051  IRDALTVGKS  EEDAKKYFLD  QIEVCRDKGW  TVQFNWFLHL  VLGIKQGEKH
1101  PA*
```

FIG.4

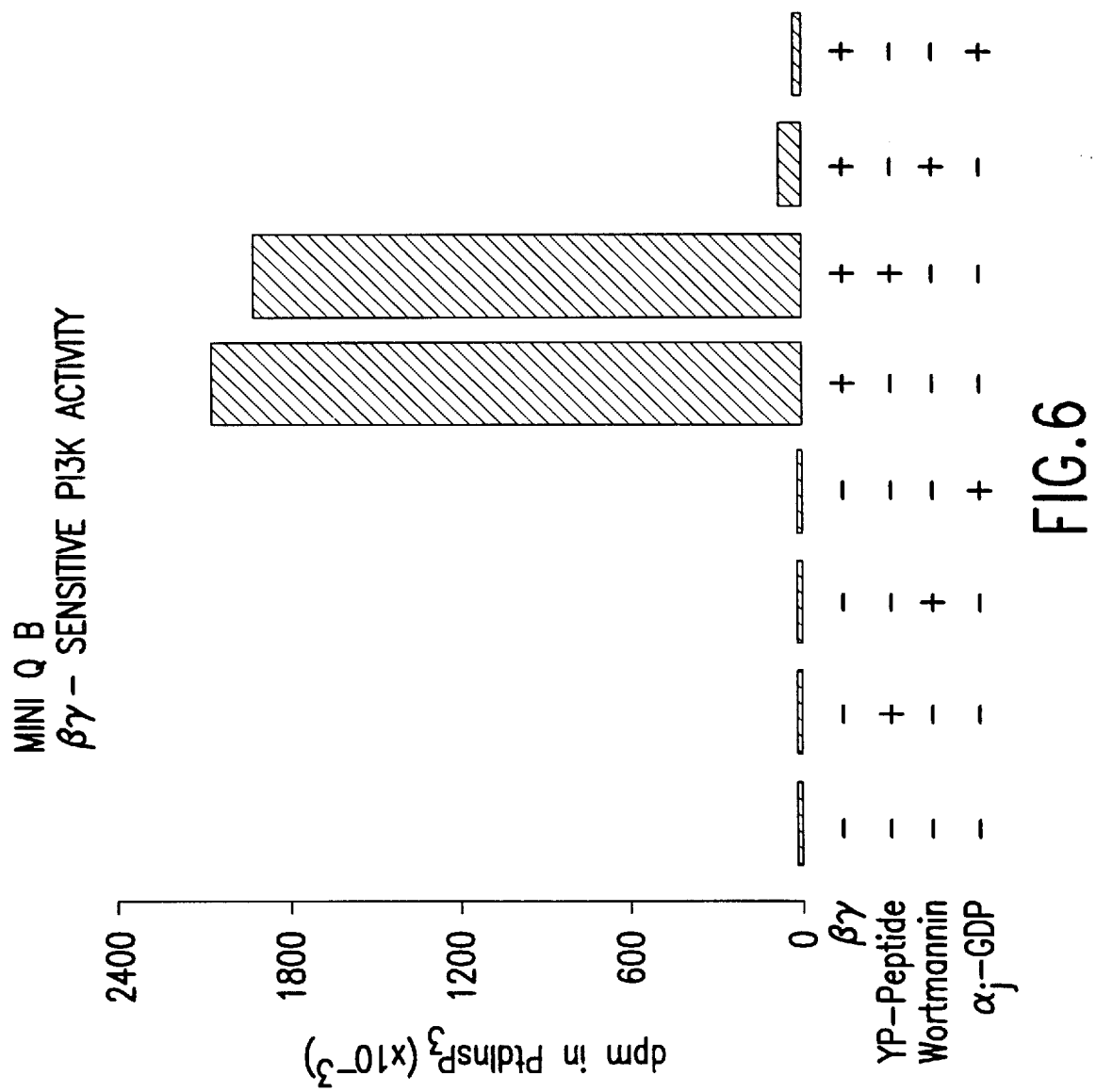

G-BETA-GAMMA REGULATED PHOSPHATIDYLINOSITOL-3' KINASE

This is a division of application Ser. No. 08/672,211, filed Jun. 27, 1996.

INTRODUCTION

The present invention relates to novel G-protein regulated phosphoinositide 3OH-kinase enzymes isolated from cells of hematopoietic lineage which are involved in cellular signal transduction pathways, and to the use of these novel enzymes in the treatment and diagnosis of disease.

BACKGROUND OF THE INVENTION

Phosphoinositide 3OH-kinases (PI3Ks) are a large family of enzymes capable of 3-phosphorylating at least one of the cellular phosphoinositides (Whitman et al., 1988, Nature 332:644–646; Auger et al., 1989, Cell 57:167–175). 3-phosphorylated phosphoinositides are found in all higher eukaryotic cells. A growing body of evidence implicates PI3K and a lipid product of this enzyme, phosphatidylinositol (3,4,5)-triphosphate (hereinafter "PtdIns(3,4,5)$P_3$"), as part of a novel and important second messenger system in cellular signal transduction. The components of this novel PtdIns(3,4,5)$P_3$-based signalling system appear to be independent of the previously characterized signalling pathway based on inositol phospholipids, in which a phosphoinositidase C (PIC) hydrolyses PtdIns(4,5)$P_2$ to release the structurally distinct second messengers inositol (1,4,5)-triphosphate (Ins(1,4,5)$P_3$) and diacylglycerol.

Select extracellular agonists and growth factors will stimulate intracellular PI3K activity and cause the rapid and transient intracellular accumulation of PtdIns(3,4,5)$P_3$. Surprisingly, stimulation of a variety of different types of cell surface receptors, including receptor tyrosine kinases, receptors associated with src family non-receptor tyrosine kinases, cytokine growth factors, and G protein coupled receptors will all activate members of the PI3K family. (Reviewed in Stephens et al., 1993, Biochemica et Biophysica Acta, 1179:27–75). For example, tyrosine kinase receptors which, when activated, result in increased accumulation of PtdIns(3,4,5)$P_3$ are the PDGF receptor, the EGF receptor, members of the FGF receptor family, the CSF-1 receptor, the insulin receptor, the IGF-1 receptor, and the NGF receptor. Receptors associated with src family non-receptor tyrosine kinases which stimulate PtdIns(3,4,5)$P_3$ accumulation are the Il-2 receptor, Il-3 receptor, mIgM receptor, the CD4 receptor, the CD2 receptor, and the CD3/T cell receptor. Additionally, the cytokine Il-4 receptor and the G protein linked thrombin receptor, ATP receptor, and the fMLP receptor all stimulate the activity of a PI3K, resulting in subsequent PtdIns (3,4,5)$P_3$ accumulation. Thus, PtdIns (3,4,5)$P_3$ appears to be a second messenger in extremely diverse signalling pathways.

Support for the proposition that PI3K activity and production of PtdIns(3,4,5)$P_3$ is a physiological relevant pathway of signal transduction for these diverse receptors is derived, inter alia, from two different lines of experimental evidence: inhibition of PI3K activity by fungal metabolites and observations of direct protein associations. Wortmannin, a fungal metabolite, irreversibly inhibits PI3K activity by binding covalently to the catalytic domain of this enzyme. Inhibition of PI3K activity by wortmannin eliminates the subsequent cellular response to the extracellular factor. For example, neutrophils respond to the chemokine fMet-Leu-Phe (fMLP) by stimulating PI3K and synthesizing PtdIns (3,4,5)$P_3$. The synthesis correlates with activation of the respiratory burst involved in neutrophil destruction of invading microorganisms. Treatment of neutrophils with wortmannin prevents the fMLP-induced respiratory burst response. Thelen et al., 1994, PNAS, USA 91:4960–4964. Indeed, these experiments with wortmannin, as well as other experimental evidence, shows that PI3K activity in cells of hematopoietic lineage, particularly neutrophils, monocytes, and other types of leukocytes, is involved in many of the non-memory immune responses associated with acute and chronic inflammation.

PI3K enzymes interact directly with, and may be co-purified with, activated forms of several receptor tyrosine kinases. When purified, receptor tyrosine kinase associated PI3K was found to consist of 170–200 kD heterodimers (Otsu et al., 1991, Cell 65:91–104, Pons et al., 1995, Mol. Cell. Biol. 15:4453–4465, Inukai et al., 1996, J. Biol. Chem. 271:5317–5320) comprising a catalytic subunit and an adaptor (or regulatory) subunit.

Two different homologs of the catalytic subunit, p110α and p110β, have been described and cloned. The catalytic subunit, which irreversibly binds wortmannin, tightly associates with one or other members of a small family of highly related regulatory subunits, p55α, p55PIK, p85α and p85β, to form the 170–200 kD heterodimers. The known regulatory subunits contain a large collection of protein:protein interaction domains, including two SH2 domains (Cantley et al., 1991, Cell 64:281–302).

The presence of the SH2 domains are thought to be responsible for the binding and stimulation of PI3K heterodimers to activated receptor tyrosine kinases. Activated receptors are phosphorylated at key tyrosine residues within local consensus sequences preferred by the SH2 domains found in the 55–87 kD PI3K adaptors (Songyang et al., 1993, Cell 72:767–778). Once the PI3K heterodimer binds, it directly activates the PI3K catalytic subunit (although this effect is relatively small in vitro, Carpenter et al., 1993, J. Biol. Chem. 268:9478–9483, Backer et al., 1992, EMBO J. 11:3469–3479) and translocates the cytosolic PI3K to a source of its phospholipid substrate. The combination of these factors leads to a surge in PtdIns(3,4,5)$P_3$ production. Clearly, these isoforms of PI3Ks (p100α/p110β/p55α, p55PIK) seem structurally adapted to function as dedicated signal transducers downstream of receptor-regulated tyrosine kinases, very like the way the τ-family of PI-PLCs are regulated by receptor-sensitive tyrosine kinases (Lee and Rhee, 1995, Current Biol. 7:193–189).

However, the p110/p85 sub-family of PI3Ks do not seem to be involved in the production of PtdIns(3,4,5)$P_3$ that can occur as a result of activation of cell surface receptors which utilize heterotrimeric GTPases to transduce their signals (e.g., fMLP, PAF, ATP, and thrombin). These types of cell surface receptors have been primarily described in cells of hematopoietic origin whose activation is involved inflammatory responses of the immune system. Recent evidence has suggested that a chromatographically distinct form of wortmannin-sensitive PI3K is present in U937 cells and neutrophils that possesses a native, relative molecular mass of about 220 kD (Stephens et al., 1994, Cell 77:83–93). This PI3K activity can be specifically stimulated by Gβγ subunits, but not Gα-GTP subunits. A similar PI3K activity has also been described in an Osteosarcoma cell line (Morris et al., 1995, Mol. Pharm. 48:532–539). Platelets also contain a Gβγ-sensitive PI3K, although it is unclear whether this is a p85/p110 PI3K family member (Thomason et al., 1994, J. Biol. Chem. 269:16525–16528). It seemed likely that this poorly characterized, Gβγ-sensitive PI3K might be responsible for production of PtdIns(3,4,5)P$_3$ in response to agonists like ATP, fMLP etc.

Stoyanov et al., (1995) have recently published the cloning and expression of a wortmannin-sensitive PtdIns(4,5) P$_2$-selective PI3K, termed p110γ, from a human bone marrow cDNA library. p110γ was amplified by PCR using primers designed to target potential PI3K's as well as PtdIns4-kinase's catalytic centers. It is clearly distinct from p110α and p110β, as it lacks, for example, an aminoterminus binding domain for a member of the p85 adaptor family. p110γ was speculated to be the PI3K activity downstream of heterotrimeric GTPase-linked receptors on the basis of its sensitivity to both Gα-GTP and Gβγ-subunits in vitro and its expression in myeloid-derived cells. Nevertheless, this hypothesis left several unresolved questions regarding the earlier biochemical evidence which indicated that the Gβγ responsive PI3K was not stimulated by Gα-GTP subunits, and that it possessed a much greater molecular mass of about 220 kD.

The effects of Gβγ subunits on p110γ were suggested to be mediated via a putative NH$_2$-terminus pleckstrin homology (PH) domain. However, with the description of an increasing number of Gβγ regulated effectors, mounting evidence suggests that PH domains do not represent a widely used Gβγ binding domain. Recent work, using a panel of relatively small peptides based on the sequence of domains only found in the Gβγ-activated adenylate cyclases (ACs 2 and 4) which specifically block Gβγ activation or inhibition of several effectors, has suggested there may be some grounds for believing Gβγ subunits contain a widely used effector activating domain. Further, regions in different effectors that interact with this effector activating domain show significant sequence similarities. Hence a motif (Gln-X-X-Glu-Arg) within the domain in AC2 highlighted by these peptide studies also appears in regions of potassium channels and β-ARKs already implicated in regulation by Gβγ subunits (Chen et al., 1995, Science 268:1166–1169). However, this motif is not replicated in all proteins known to be regulated by Gβγ subunits, and consequently sequence analysis cannot currently predict whether a protein will be regulated by Gβγ subunits.

Identification of the mechanism by which PI3K activity is activated by cellular agonists which transduce their signals through G protein linked receptors is lacking. It is important to note that the vast majority of agonists which activate the neutrophil respiratory burst involved in the inflammatory response will bind to G-protein-coupled receptors rather than receptor tyrosine kinases. Thus, the mechanism by which PI3K is regulated in response to these types of chemokines is likely to be very different from regulation by growth factors which signal through tyrosine kinases. The present invention is directed towards resolving this issue by the identification, purification, and cloning of a novel and specific form of PI3K which is activated by βγ subunits of trimeric G-proteins.

3. SUMMARY OF THE INVENTION

The present invention relates to the discovery, identification, purification, and cloning of nucleotides that encode the trimeric G protein regulated PI3K, a novel protein that produces accumulation of the second messenger PtdIns(3,4,5)P$_3$ in response to activation of G protein-linked receptors. This novel G-protein regulated PI3K is comprised of a catalytic subunit, p120, and a regulatory subunit, p101. The p120 catalytic subunit shares partial amino acid sequence homology with the PI3K catalytic subunits p110α, p110β, and p110γ, p101, on the other hand, is a completely new protein with no identifiable homology to any other sequence previously available. In the absence of p101 regulatory subunit, activated G protein subunits induce a mild stimulation of catalytic activity by the p120 catalytic subunit. However, in the presence of p101 subunit, the PI3K activity of the catalytic subunit is stimulated over 100 fold by activated G proteins.

The p101 and p120 cDNAs, described herein, encode proteins of about 877 amino acids and about 1102 amino acids, respectively (FIG. 2 and FIG. 4). Although the amino acid sequence of p120 protein is homologous to that of other known PI3K catalytic subunits, the p120 cDNA described herein encodes a protein which diverges from that of the known PI3K catalytic subunits, particularly at, for example, the carboxyl terminus (amino acid residues 1075 to 1102).

The p101 transcript is found primarily in cells of hematopoietic lineage. p120, and other PI3K catalytic subunit proteins, appear to have a far broader tissue and cell type distribution. Notably, the presence of a trimeric G protein sensitive PI3K activity has only been found in a limited number of cells of hematopoietic lineage (e.g., neutrophils, platelets, etc.). Thus, the ability to activate PI3K enzymes in response to stimulation of trimeric G protein linked receptors appears largely dependent on the presence of the p101 subunit.

The invention encompasses the following nucleotides, host cells expressing such nucleotides, and the expression products of such nucleotides: (a) nucleotides that encode mammalian p101 and p120 proteins, including the porcine p101 and p120, and the p101 and p120 gene product; (b) nucleotides that encode portions of p101 and p120 that correspond to its functional domains, and the polypeptide products specified by such nucleotide sequences, including but not limited to the p101 nucleotides encoding, for example, the p101 Gβγ interaction domain, or the catalytic subunit associating domain, or amino acid residues from about 1 to 160, 80–120, 161 to 263, 264 to 414, 415 to 565,566 to 706, 707–832, and/or 833 to 877, and p120 nucleotides that encode the p120 membrane binding domain, or the regulatory subunit domain, or amino acid residues from about 173 to 302 and 310 to 315; (c) nucleotides that encode mutants of p101 and p120 in which all or a part of one of the domains is deleted or altered, and the polypeptide products specified by such nucleotide sequences, including but not limited to mutants of p101 wherein the nucleotides encoding the G protein interaction domain, or the catalytic subunit associating domain, or amino acid residues from about 1 to 160, 80–120, 161 to 263, 264 to 414, 415 to 565,566 to 706, 707–832, and/or 833 to 877 are deleted, and to mutants of p120 wherein the nucleotides encoding the membrane binding domain, or the regulatory subunit domain, or amino acid residues from about 173 to 302 and 310 to 315 are deleted; (d) nucleotides that encode fusion proteins containing the p101 protein or one of its domains (e.g., the Gβγ interaction domain, or the catalytic subunit associating domain, or the domains described by amino acid residues from about 1 to 160, 80–120, 161 to 263, 264 to 414, 415 to 565,566 to 706, 707–832, and/or 833 to 877), or the p120 protein or one of its domains (e.g., the membrane binding domain, or the regulatory subunit domain, or amino acid residues from about 173 to 302 and 310 to 315) fused to another polypeptide.

The invention also encompasses agonists and antagonists of G protein regulated PI3K, including small molecules, large molecules, mutant p101 proteins that compete with native p101, and antibodies, as well as nucleotide sequences that can be used to inhibit p101 gene expression (e.g., antisense and ribozyme molecules, and gene or regulatory sequence replacement constructs) or to enhance p101 gene expression (e.g., expression constructs that place the p101 gene under the control of a strong promoter system), and transgenic cells and animals that express a p101 transgene or "knock-outs" that do not express p101.

In addition, the present invention encompasses methods and compositions for the diagnostic evaluation, typing and prognosis of immune system disorders, including inflammation, and for the identification of subjects having a predisposition to such conditions. For example, p101 nucleic acid molecules of the invention can be used as diagnostic hybridization probes or as primers for diagnostic PCR analysis for the identification of p101 gene mutations, allelic variations and regulatory defects in the p101 gene. The present invention further provides for diagnostic kits for the practice of such methods.

Further, the present invention also relates to methods for the use of the p101 gene and/or p120 gene products for the identification of compounds which modulate, i.e., act as agonists or antagonists, of G protein-regulated PI3K gene expression and or p101 and/or p120 gene product activity. Such compounds can be used as agents to control immune system disorders and, in particular, as therapeutic agents for the treatment of inflammation disorders such as arthritis, septic shock, adult respiratory distress syndrome (ARDS), pneumonia, asthma, allergies, reperfusion injury, atherosclerosis, Alzheimer's disease, and cancer.

Still further, the invention encompasses methods and compositions for the treatment of inflammation disorders such as arthritis, septic shock, adult respiratory distress syndrome (ARDS), pneumonia, asthma, allergies, reperfusion injury, atherosclerosis, Alzheimer's disease, and cancer. Such methods and compositions are capable of modulating the level of p101 gene expression and/or the level of p101 or p120 gene product activity.

This invention is based, in part, on the surprising discovery of a G protein stimulated PI3K activity in isolated neutrophils, the purification and characterization of this activity as a heterodimeric PI3K protein comprised of a p101 subunit and a p120 subunit, the identification and cloning of p101 and p120 cDNA from a library prepared from neutrophil mRNA, characterization of the novel sequences, and studies of isolated recombinantly expressed p101 and p120 protein in insect cells, U937 cells, and Cos-7 cells.

3.1 DEFINITIONS

As used herein, the following terms, whether used in the singular or plural, will have the meanings indicated:

G protein-regulated PI3K: refers to a PI3K enzyme whose activity is stimulated by activated trimeric G proteins such as Gβγ subunits and/or Gα-GTP subunits.

p101: means the regulatory subunit of the G protein-regulated PI3K, also known as the adaptor subunit. p101 includes molecules that are homologous to p101 or which bind to p120 and stimulate PI3K catalytic activity in response to activation of trimeric G proteins. p101 fusion proteins having an N-terminal Glu tag (specifically MEEEEFMPMPMEF) are referred to herein as (EE)101 fusion proteins, while p101 fusion proteins having an N-terminal myc epitope tag are referred to herein as myc101 fusion proteins.

p101 nucleotides or coding sequences: means nucleotide sequences encoding the p101 regulatory subunit protein, polypeptide or peptide fragments of p101 protein, or p101 fusion proteins. p101 nucleotide sequences encompass DNA, including genomic DNA (e.g. the p101 gene) or cDNA, or RNA.

p120: means the catalytic subunit of the G protein-regulated PI3K. Polypeptides or peptide fragments of p120 protein are referred to as p120 polypeptides or p120 peptides. Fusions of p120, or p120 polypeptides or peptide fragments to an unrelated protein are referred to herein as p120 fusion proteins. (EE)120 fusion proteins have the N-terminal Glu tag MEEEEFMPMEFSS. Functional equivalents of p120 refer to a PI3K catalytic subunit protein which binds to the p101 regulatory subunit with high affinity in vivo or in vitro. Other functional equivalents of p120 are homologous catalytic subunits of a G protein-regulated PI3K, such as p117.

p120 nucleotides or coding sequences: means nucleotide sequences encoding the p120 catalytic subunit protein, polypeptide or peptide fragments of p120 protein, or p120 fusion proteins. p120 nucleotide sequences encompass DNA, including genomic DNA (e.g. the p120 gene) or cDNA, or RNA.

4. DESCRIPTION OF THE FIGURES

FIGS. 1A, 1B, 1C, and 1D. Porcine p101 adaptor subunit nucleotide sequence.

FIG. 2. Deduced Porcine p101 amino acid sequence. Tryptic peptides identified by protein sequencing are underlined with a solid line.

FIGS. 3A, 3B and 3C. Porcine p120 catalytic subunit nucleotide sequence.

FIG. 4. Deduced Porcine p120 catalytic subunit sequence. Tryptic peptides identified by protein sequencing are underlined with a solid line. The region of divergence from the published amino acid sequence of p110γ is underscored with a broken line.

Figure 5B:
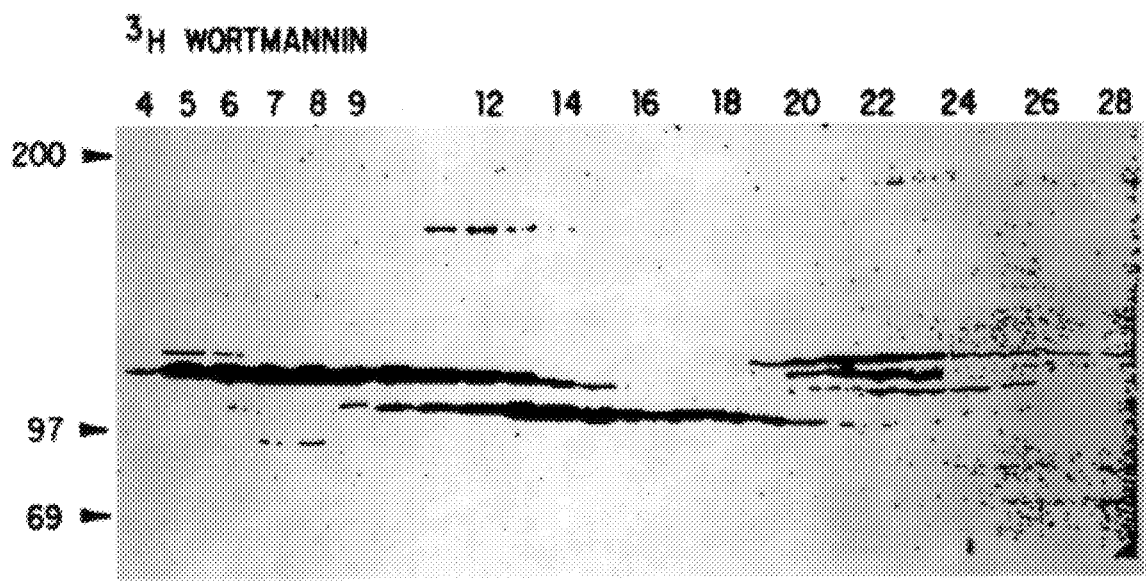

FIG. 5. Gβγ-sensitive PI3K in neutrophil cytosol is distinct to p85/p110 PI3Ks. Aliquots of each of the fractions derived from a Q-sepharose chromatographic profile were either Western blotted and probed-with αp85α or αp85β monoclonal antibodies and visualized with an HRP-linked second antibody (upper panel in FIG. 5), or incubated with 100 nM [$^3$H]-17-hydroxy-wortmannin, resolved by SDS-PAGE (6% acrylamide and fluorographed (lower panel in FIG. 5). Gβγ-sensitive PI3K activity eluted in fractions 20–24.

FIG. 6. Peak B After Final Mini Q Column Purification Contains a Gβγ-sensitive PI3K Activity. The final purification product of the Peak B activity was analyzed after isolation from a Mini Q column in the presence and absence of activated Gβγ subunits (βγ), a tyrosine phosphorylated peptide (YP-peptide), wortmannin, and/or Gα$_i$-GDP subunits (α$_i$-GDP)

Figure 7:
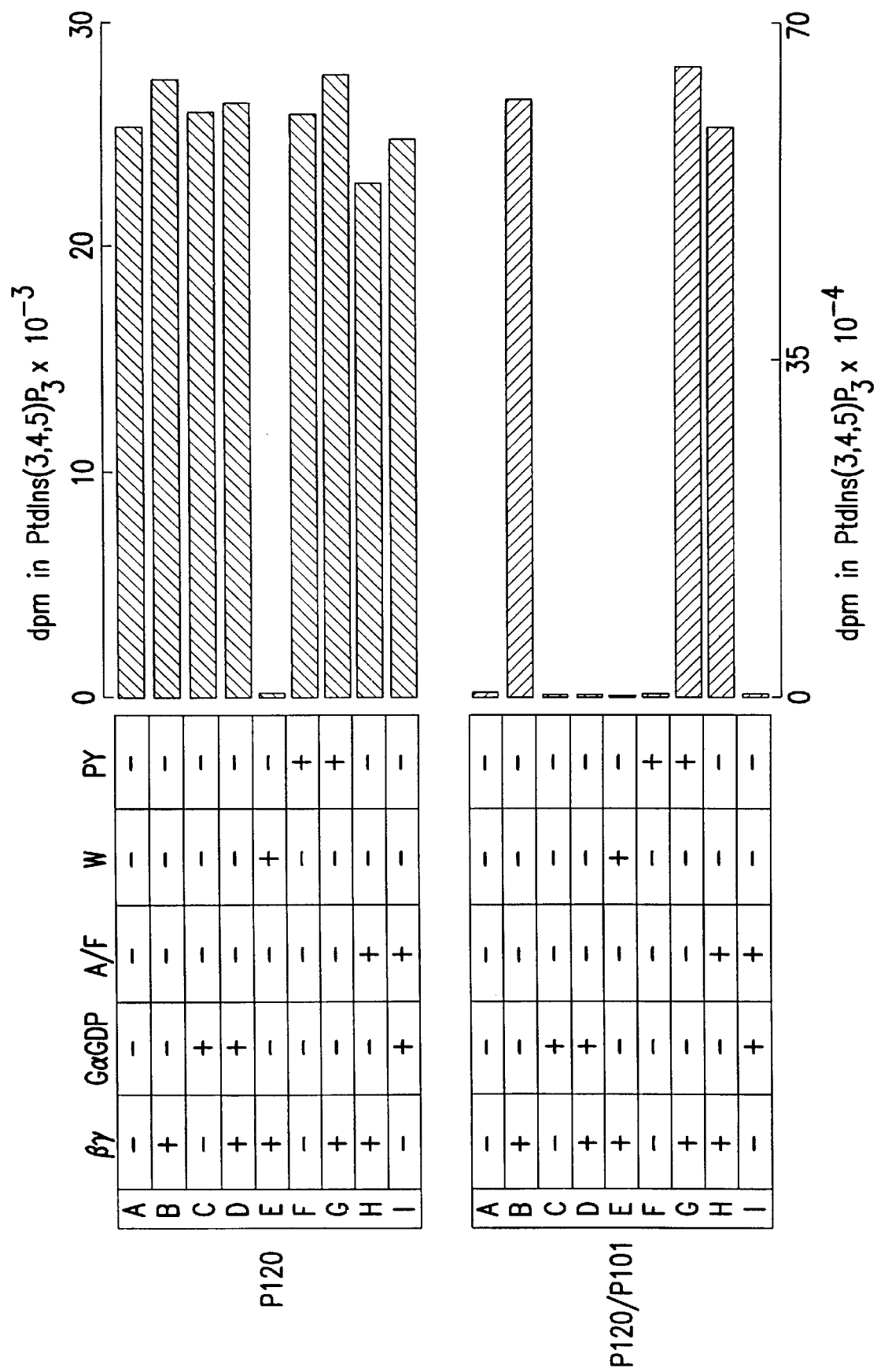

FIG. 7. Pharmacological and regulatory properties of free p120 and p101/p120 PI3Ks recombinantly expressed in Sf9 cells. Assays contained either 7 nM p101/p120 or 36 nM p120 alone (final concentrations) which were incubated with various reagents; 10 mM NaF and 30 µM AlCl$_3$ (A/F); 1 µM Gβγ subunits (βγ); 2 µM Gα-GDP; 100 nM wortmannin (W) or 50 µM tyrosine phosphorylated peptide (PY) for a total of 15 minutes (at 0° C.) prior to starting the assays by adding [γ$^{32}$P]-ATP; [$^{32}$P]-incorporated into [$^{32}$P]-PtdIns (3,4,5)P$_3$ was quantified. The data shown are means (n=2).

Figure 8:
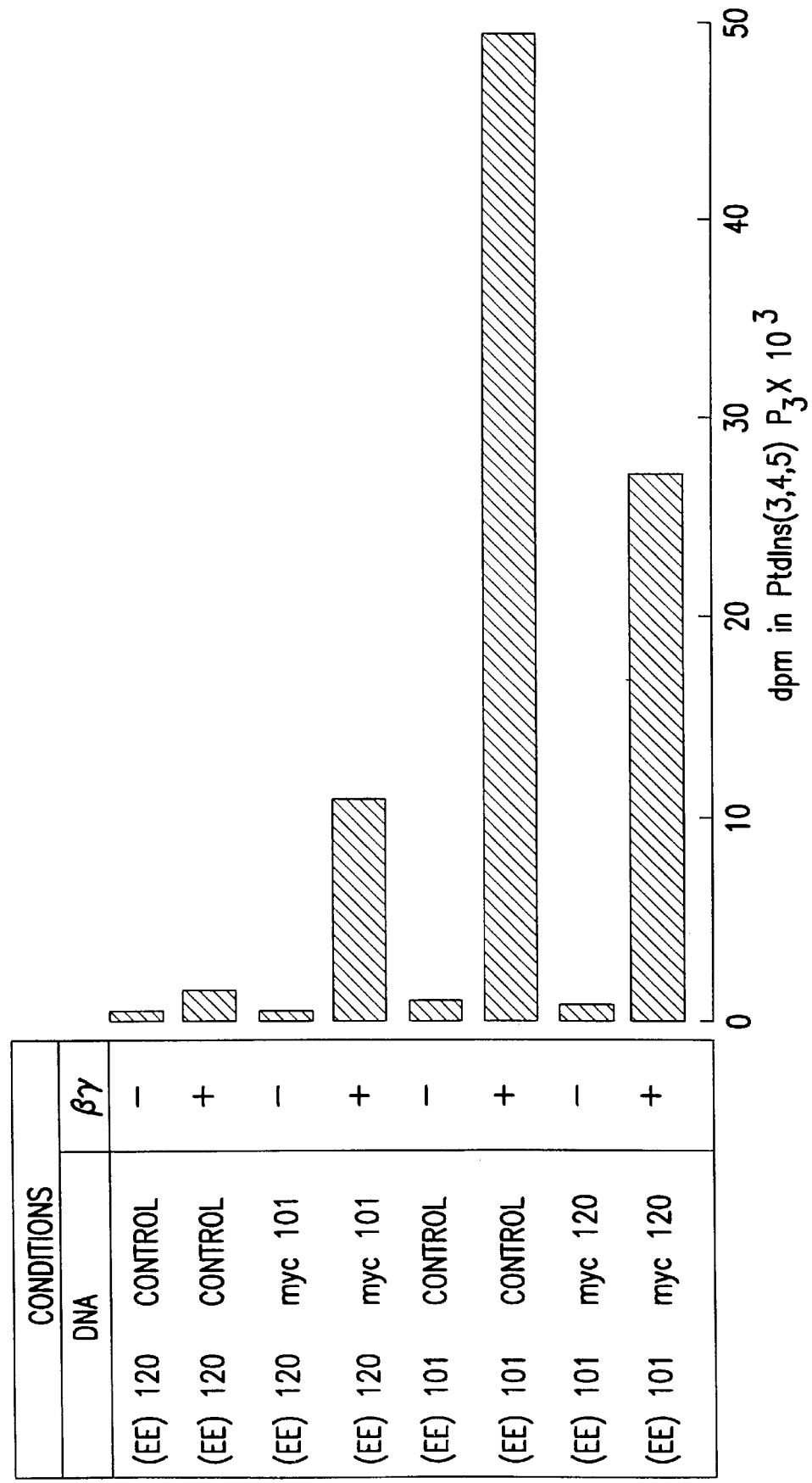

FIG. 8. p101 can associate with a Gβγ-stimulated PI3K activity in U937 cells. U937 cells were transiently transfected with mammalian expression vectors encoding either (EE) 120 or (EE) 101, co-transfected in combination with mammalian expression vectors encoding myc101, myc120, or an irrelevant control myc fusion protein, as indicated. A total of 40 μg of vector DNA was used. After co-transfection, the cells lysed, precleaned and immunoprecipitated with protein G sepharose covalently cross-linked to α-(EE) monoclonal antibody as described more fully in the Examples herein. The resulting immunoprecipitates were washed and Gβγ-activated (1 μM, final concentration) PI3K activity was assayed. The PI3K activity detected in immunoprecipitates from cells transfected with irrelevant (EE)-tagged protein, either with or without Gβγs was subtracted from the data shown (these were means of 1896 dpm and 2862 dpm in-the absence and presence of Gβγs, respectively). Parallel transfections labelled with [$^{35}$S]-methionine showed the amount of [$^{35}$S]-p101 and [35S]-p120 in the immunoprecipitates fell by 40% when they were co-transfected (data not shown).

Figure 9:
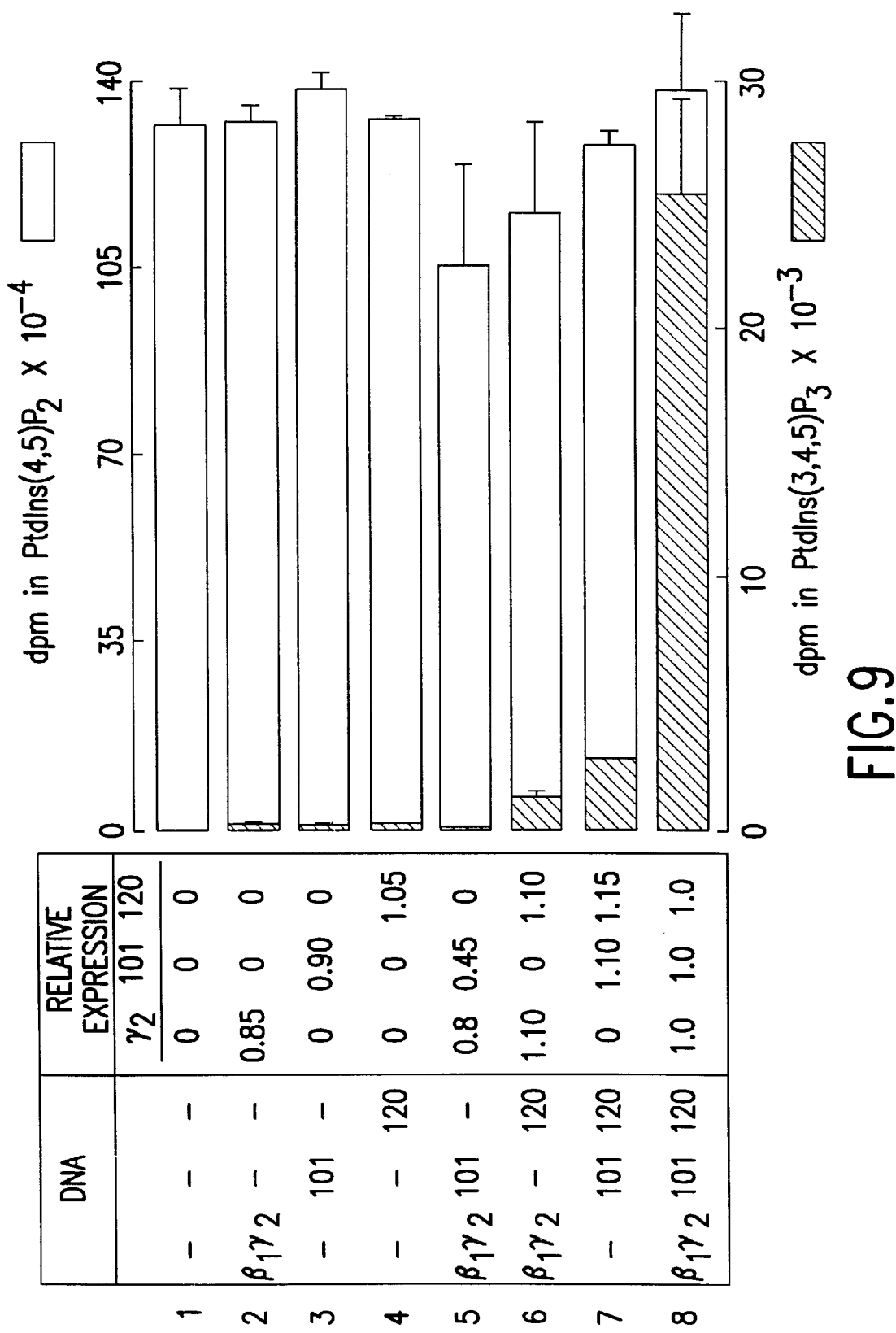

FIG. 9. Regulation of p101/p120 by Gβγs in vivo. Cos-7 cells were transfected with mammalian expression vectors encoding Gβγ subunit ("$β_1γ_2$"), p101 ("101"), and/or p120 ("120"), as indicated. After 48 hours of transient expression, cells from each transfection were either Western blotted to determine "Relative Expression", or assayed for the accumulation of PtdIns(3,4,5)P$_3$ accumulation (shaded bars). For Western blotting, samples were probed with an α-(myc) monoclonal antibody to quantitate the expression of the various (myc)-tagged proteins. Results are given relative to the expression obtained in the presence of all 4 key vectors; the absolute levels of (myc)-p120 and (myc)-p101 were very similar and about 10× greater than that of (myc)-γ$_2$. Parallel batches of cells were labelled with [$^{32}$P]-Pi; after 90 minutes lipids were extracted, deacylated and water-soluble head groups resolved by anion-exchange HPLC and quantitated by liquid scintillation counting. Data shown are means (n=2) +/− ranges. Data for [$^{32}$P]-PtdIns(3,4,5)P$_3$ are above the irrelevant DNA control (972±41 dpm).

5. DETAILED DESCRIPTION OF THE INVENTION

The present invention relates to the identification, purification, and cloning of a specific form of PI3K which is activated by βγ subunits of trimeric G-proteins. p101, described for the first time herein, is a novel subunit of the G-protein regulated P13K. Also described herein is the identification, cloning, and correct sequence of p120, the catalytic subunit of the trimeric G-protein regulated PI3K.

PI3K are enzymes which phosphorylate phosphatidyl inositols at the 3d position to generate the intracellular signaling molecule PtdIns(3,4,5)P$_3$. Although it has been shown that PI3K's are induced in a variety of cell types upon stimulation of tyrosine kinase receptors, PI3K's which are activated by trimeric G-protein linked-receptors have only been detected in a limited number of hematopoietic lineage derived cells such as platelets, monocytes, and leukocytes.

Interestingly, accumulation of PtdIns(3,4,5)P$_3$ in these cells is associated with many of the immune responses involved in acute and chronic inflammation. For example, neutrophils are activated by, inter alia, the chemokine fMLP which is released in response to infection by microorganisms. This agonist binds to a pertussis toxin sensitive G protein coupled receptor and activates the neutrophil respiratory burst, resulting in superoxide production and cytotoxicity. The respiratory burst response correlates with a rapid and transient intracellular increase in PI3K activity.

Studies in neutrophils demonstrates that wortmannin, which selectively inhibits the catalytic component of PI3K's, causes a shutdown of superoxide production. Since the vast majority of agonists which activate this respiratory burst bind to G protein-linked receptors, the G protein regulated PI3K activity represents a candidate for a dominant effector pathway whose inhibition will reduce the destructive cellular effects of inflammation. However, wortmannin is not a clinically appropriate inhibitor of this pathway since wortmannin inhibits all PI3K catalytic activities, including those involved in other cellular pathways such as growth factors.

Reported herein is the discovery that the G-protein regulated PI3K is composed of two subunits: the catalytic subunit (p110γ, p117 or p120); and the p101 regulatory subunit. The ability of PI3K to respond to cell surface receptors which stimulate the release of Gβγ subunits from activated trimeric G-proteins is largely dependent on the presence of the p101 regulatory subunit. Although catalytic subunits exhibit a small stimulation (approximately 1.7 fold) of PI3K activity in vitro in the presence of Gβγ subunits, addition of p101 proteins will increase Gβγ stimulation of PI3K activity 100 fold. Neutralization of p101, removal of p101, or interference of p101 binding to its binding partners, will render the cells incapable of generating greatly increased levels of the intracellular signal PtdIns(3,4,5)P$_3$ in response to activated Gβγ subunits. Thus, the limited distribution of the p101 subunit in bone marrow derived cells appears to be the critical factor in the cell type specificity of this response. Furthermore, p101 contains no significant homologies with any other identified sequence. This discovery makes p101, and the p101/p120 complex, the target of choice to inhibit, activate, or modulate G protein-activated PI3K with minimal non-specific effects.

The invention also encompasses the use of p101 and p120 nucleotides, p101 and p120 proteins and peptides, as well as antibodies to p101 and p120 (which can, for example, act as p101 or p120 agonists or antagonists), antagonists that inhibit G protein-activated PI3K activity or expression, or agonists that activate G protein-activated PI3K activity or increase its expression in the treatment of hematopoietic lineage cell activation disorders, including, but not limited to immune responses associated with acute and chronic inflammation, in animals such as humans. For example, antagonists of Gβγ-activated PI3K will be useful in the treatment of arthritis, including rheumatoid arthritis, septic shock, adult respiratory distress syndrome (ARDS), pneumonia, asthma and other lung conditions, allergies, reperfusion injury, atherosclerosis and other cardiovascular diseases, Alzheimer's disease, and cancer, to name just a few inflammatory disorders. In addition, p101 nucleotides and p101 regulatory subunits, as well as p120 nucleotides and p120 catalytic subunits, are useful for the identification of compounds effective in the treatment of hematopoietic lineage cell activation disorders involving G protein-activated PI3Ks.

Further, the invention encompasses the use of p101 and p120 nucleotides, p101 and p120 proteins and peptides, as well as antibodies to p101 and p120 in the diagnosis of hematopoietic lineage cell activation disorders. The diagnosis of a p101 regulatory subunit or p120 catalytic subunit abnormality in a patient, or an abnormality in the G protein activated PI3K signal transduction pathway, will also assist in devising a proper treatment or therapeutic regimen.

In particular, the invention described in the subsections below encompasses p101 regulatory subunit, polypeptides or peptides corresponding to functional domains of the p101 regulatory subunit (e.g., the catalytic subunit association domain, or the domain which interacts with activated G proteins), mutated, truncated or deleted p101 regulatory subunits (e.g. a p101 regulatory subunit with one or more functional domains or portions thereof deleted), p101 regulatory subunit fusion proteins (e.g. a p101 regulatory subunit or a functional domain of p101 regulatory subunit, fused to an unrelated protein or peptide such as an epitope tag, i.e., the myc epitope), nucleotide sequences encoding such products, and host cell expression systems that can produce such p110 regulatory subunit products.

Additionally, the invention encompasses p120 catalytic subunit proteins, polypeptides, functional domains of the p120 subunit (e.g., the catalytic domain), mutated, truncated or deleted p120 subunit proteins, p120 fusion proteins, nucleotide sequences encoding such products, and host cell expression systems that can produce such p120 catalytic subunit products.

The invention also encompasses antibodies and anti-idiotypic antibodies (including Fab fragments), antagonists and agonists of the G protein-activated PI3K, as well as compounds or nucleotide constructs that inhibit expression of the p101 or p120 gene (transcription factor inhibitors, antisense and ribozyme molecules, or gene or regulatory sequence replacement constructs), or promote expression of p101 regulatory subunit (e.g., expression constructs in which p101 coding sequences are operatively associated with expression control elements such as promoters, promoter/enhancers, etc.). The invention also relates to host cells and animals genetically engineered to express the human p101 regulatory subunit (or mutants thereof) or to inhibit or "knock-out" expression of the animal's endogenous p101 regulatory subunit.

Further, the invention particularly encompasses antagonists which prevent the association of p101 regulatory subunits with their binding partners, including p120 and other PI3K catalytic subunit proteins such as p117 and p110γ, as well as activated trimeric G protein proteins, including Gβγ subunits.

The p101 regulatory subunit proteins or peptides, p101 regulatory subunit fusion proteins, p101 nucleotide sequences, antibodies, antagonists and agonists can be useful for the detection of mutant p101 regulatory subunits or inappropriately expressed p101 regulatory subunits for the diagnosis of immune disorders. The p101 and p120 subunit proteins or peptides, p101 and p120 subunit fusion proteins, p101 and p120 nucleotide sequences, host cell expression systems, antibodies, antagonists, agonists and genetically engineered cells and animals can be used for screening for drugs effective in the treatment of such immune disorders. The use of engineered host cells and/or animals may offer an advantage in that such systems allow not only for the identification of compounds that bind to the p101 regulatory subunit, but can also identify compounds that affect the signal transduced by the activated p101 regulatory subunit, specifically, production of the intracellular signaling molecule PtdIns(3,4,5)P$_3$.

Finally, the p101 regulatory subunit protein products and fusion protein products, antibodies and anti-idiotypic antibodies (including Fab fragments), antagonists or agonists (including compounds that modulate signal transduction which may act on downstream targets in the p101 regulatory subunit signal transduction pathway) can be used for therapy of such diseases. For example, nucleotide constructs encoding functional p101 regulatory subunits, mutant p101 regulatory subunits, as well as antisense and ribozyme molecules can be used in "gene therapy" approaches for the modulation of p101 regulatory subunit expression and/or activity in the treatment of hematopoietic lineage cell activation disorders. Thus, the invention also encompasses pharmaceutical formulations and methods for treating hematopoietic lineage cell activation disorders.

The invention is based, in part, on the surprising discovery of novel PI3K enzymes in porcine neutrophils. Like other PI3K proteins, these enzymes 3-phosphorylate PtdIns, PtdIns4P and PtdIns(4,5)P$_2$ substrates, and were completely inhibited by 100 nM wortmannin. However, unlike the previously described PI3K p85/p101 protein complexes, the PI3K activity was stimulated over 100 fold by incubation with Gβγ subunits. Addition of Gα-GDP subunits could inhibit this Gβγ activation. Furthermore, the PI3K activity was not stimulated by phosphorylated tyrosine peptides. When purified, two distinct heterodimeric protein complex were identified: a p117/p101 complex and a p120/p101 complex.

Peptide sequencing revealed that the p101 protein was identical in each complex. The p120 and p117 proteins were homologous with the exception of the amino terminus (see Examples below). Porcine p101 and p120 cDNAs were then cloned using degenerate probes based upon the peptide sequence to screen an expression library of cDNAs synthesized from porcine neutrophil mRNA. While sequence analysis revealed that the p120 protein is homologous to previously cloned PI3K catalytic subunits (although it diverged significantly at the extreme carboxyl terminus), the p101 protein was unrelated to any sequence in the databases.

Experiments described herein expressing p101 and/or p120 fusion proteins in insect cells demonstrated that p101 binds tightly to p120 in a 1:1 molar stoichiometry. Free purified p120 exhibited PI3K activity which was insensitive to the presence of Gα subunits and tyrosine phosphorylated peptides, and only mildly stimulated by Gβγ subunits. However, when bound to p101, the PI3K activity of p120 was stimulated 100 fold by the presence of Gβγ subunits. When p101 was expressed alone in insect cells, p101 did not exhibit PI3K activity.

An interesting result occurred when p101 was expressed as a tagged fusion protein in human U937 cells. When this recombinantly expressed porcine p101 was immunoprecipitated via the fusion protein tag, these immunoprecipitants did contain G protein regulated PI3K activity. Coexpression of, p120 with p101 slightly decreased the amount of PI3K activity that could be immunoprecipitated. These results indicated the human U937 cells contained a PI3K catalytic subunit which could bind to and be activated by the porcine p101 regulatory subunit. Thus, the components of this signalling pathway appear conserved among different mammalian species.

Further, transient transfections were performed in Cos-7 cells, which do not normally stimulate PI3K activity in response to activated G-proteins, with constructs encoding p101, p120 and/or Gβγ subunits. Transfection of a construct which expressed p120 only produced significant increases in cellular PtdIns(3,4,5)P$_3$ levels in a Gβγ dependent fashion when co-expressed in the presence of p101.

Various aspects of the invention are described in greater detail in the subsections below.

5.1 THE p101 AND p120 GENES

The cDNA sequence (SEQ. ID. No. 1) and deduced amino acid sequence (SEQ. ID. No. 2) of porcine p101 regulatory subunit are shown in FIGS. 1 and 2, respectively. A relatively common allelic variation occurs at amino acid residue 483 in the open reading frame; a serine may be replaced by a glycine at this position.

The nucleotide sequence encoding the first 733 amino acids of the p101 regulatory subunit is believed to be sufficient to bind the catalytic subunit. However, without the 145 carboxyl terminal amino acids, this truncated p101 bound to p120 will not stimulate PI3K activity in response to Gβγ subunits. Therefore, the catalytic subunit associating domain is believed to be contained within the first 732 amino acids, and the carboxyl terminal amino acids 733 to 877 could be involved in the response to Gβγ subunits.

Other domains of p101 are described by amino acid residues from about 1 to 160, 80–120, 161 to 263, 264 to 414, 415 to 565, 566 to 706, 707–832, and/or 833 to 877. The nucleotide sequences which encode amino acid residues from about 161 to 263 define a pleckstrin homology ("PH") domain. (PROSITE:PS50003). PH domains may be involved in binding of proteins to Gβγ subunits (Touhara et al., 1994, J. Biol. Chem. 269:10217) and to membrane phospholipids (see Shaw, 1996, Bioessays 18:35–46). Thus, the PH domain of p101 may be involved in both of these events.

The nucleotide sequences encoding amino acids 1 to 160 of p101 may be responsible for binding to the p120 catalytic subunit. When this region of the p101 protein is analyzed for secondary structure, it is predicted to have a self-contained alternating α-helix/β-sheet structure. Within this structure is found homology to a "WW domain" (Staub et al., 1996, Structure 4:495–499 and TIBS 21:161–163). This WW domain may bind to a proline-rich domain found within the N-terminus of p120 protein (residues 310 to 315). Thus, the WW domain of p101 may be involved in mediating the interaction between the regulatory subunit and the catalytic subunit.

The cDNA sequence (SEQ. ID. No:3) and deduced amino acid sequence (SEQ. ID. No:4) of porcine p120 are shown in FIGS. 3 and 4, respectively. A cryptic thrombin cleavage site is present after the first approximately 40 amino acid residues. The truncated p120 protein lacking these approximately 40 amino terminal residues is still able to bind to p101, but PI3K activity is reduced approximately 20 to 30%. Although the p120 protein was highly homologous to the previously cloned p110γ protein reported by Stoyanov et al. (1995), the extreme C-terminus of p120 diverges from the reported p110γ protein at amino acid residue 1075; thus, the last 28 amino acid residues of p120 have not been published in reports of any homologous protein. As noted above, the nucleotides encoding a proline-rich region including p120 residues 310 to 315 may be involved in the interaction between p120 and p101. Additionally, the nucleotides encoding p120 amino acid residues from about 173 to 302 define a weak PH domain which may be a candidate for membrane binding and/or Gβγ subunit interaction of the p101/p120 complex.

Data presented in the working examples, infra, demonstrate that the p120 cDNA encodes the catalytic subunit of the Gβγ-activated PI3K. The p101 cDNA encodes a novel regulatory subunit protein which binds to the p120 subunit. This heterodimer 3-phosphorylates PtdIns, PtdIns4P and PtdIns(4,5)P$_2$ in response to activation of trimeric G-protein linked receptors.

The p101 nucleotide sequences of the invention include: (a) the DNA sequence shown in FIG. 1 or contained in the cDNA clone pCMV3mycp101 as deposited with the American Type Culture Collection (ATCC) under accession number 97636; (b) nucleotide sequence that encodes the amino acid sequence shown in FIG. 2, or the p101 regulatory subunit amino acid sequence encoded by the cDNA clone pCMV3mycp101 as deposited with the ATCC; (c) any nucleotide sequence that hybridizes to the complement of the DNA sequence shown in FIG. 1 or contained in the cDNA clone pCMV3mycp101 as deposited with the ATCC under highly stringent conditions, e.g., hybridization to filter-bound DNA in 0.5M NaHPO$_4$, 7% sodium dodecyl sulfate (SDS), 1 mM EDTA at 65° C., and washing in 01×SSC/0.1% SDS at 65° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product; and (d) any nucleotide sequence that hybridizes to the complement of the DNA sequences that encode the amino acid sequence shown in FIG. 1 or contained in the cDNA clone of the pCMV3mycp101 as deposited with the ATCC under less stringent conditions, such as moderately stringent conditions, e.g., washing in 0.2×SSC/0.1% SDS at 42° C. (Ausubel et al., 1989, supra), yet which still encodes a functionally equivalent p101 gene product. Functional equivalents of the p101 regulatory subunit include naturally occurring p101 regulatory subunit present in other species, and mutant p101 regulatory subunits whether naturally occurring or engineered which retain at least some of the functional activities of p101 (i.e., binding to the p120 or p117 catalytic subunit, stimulation of catalytic activity in response to Gβγ subunits, and/or interaction with Gβγ subunits). The invention also includes degenerate variants of sequences (a) through (d).

The invention also includes nucleic acid molecules, preferably DNA molecules, that hybridize to, and are therefore the complements of, the nucleotide-sequences (a) through (d), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05 sodium pyrophosphate at 37° C. (for 14-base oligos), 48° C. (for 17-base oligos), 55° C. (for 20-base oligos), and 60° C. (for 23-base oligos). These nucleic acid molecules may encode or act as p101 antisense molecules, useful, for example, in p101 gene regulation (for and/or as antisense primers in amplification reactions of p101 gene nucleic acid sequences). With respect to p101 gene regulation, such techniques can be used to regulate, for example, inflammatory immune responses. Further, such sequences may be used as part of ribozyme and/or triple helix sequences, also useful for p101 gene regulation. Still further, such molecules may be used as components of diagnostic methods whereby, for example, the presence of a particular p101 allele responsible for causing an inflammatory response, such as arthritis, may be detected.

In addition to the p101 nucleotide sequences described above, full length p101 cDNA or gene sequences present in the same species and/or homologs of the p101 gene present in other species can be identified and readily isolated, without undue experimentation, by molecular biological techniques well known in the art. Experimental evidence described herein indicates that the p101 proteins are conserved in different mammalian species since, when expressed in U937 cells, the porcine p101 bound to a human homolog of the catalytic subunit. Additionally, members of the tyrosine kinase regulated PI3K family of proteins, for example the p110/p85 PI3K, are also conserved among different mammalian species. Therefore, the human homologs of p101 and p120 can be readily identified and isolated from, for example, a U937 cDNA library or a human neutrophil cDNA library using the nucleotides and proteins of the present invention. Indeed, homologs of p101 and p120 may be isolated from a variety of mammalian cells known or suspected to contain a trimeric G-protein regulated PI3K, particularly cells of hematopoietic origin, and more particularly platelets, monocytes, leukocytes, osteoclasts, and neutrophils.

The identification of homologs of p101 in related species can be useful for developing animal model systems more closely related to humans for purposes of drug discovery. For example, expression libraries of cDNAs synthesized from neutrophil mRNA derived from the organism of interest can be screened using labeled catalytic subunit derived from that species, e.g., a p120, p117, or p110γ catalytic subunit fusion protein. Alternatively, such cDNA libraries, or genomic DNA libraries derived from the organism of interest can be screened by hybridization using the nucleotides described herein as hybridization or amplification probes. Furthermore, genes at other genetic loci within the genome that encode proteins which have extensive homology to one or more domains of the p101 gene product can also be identified via similar techniques. In the case of cDNA libraries, such screening techniques can identify clones derived from alternatively spliced transcripts in the same or different species.

Screening can be by filter hybridization, using duplicate filters. The labeled probe can contain at least 15–30 base pairs of the p101 nucleotide sequence, as shown in FIG. 1. The hybridization washing conditions used should be of a lower stringency when the cDNA library is derived from an organism different from the type of organism from which the labeled sequence was derived. With respect to the cloning of a human p101 homolog, using porcine p101 probes, for example, hybridization can, for example, be performed at 65° C. overnight in Church's buffer (7% SDS, 250 mM NaHPO$_4$, 2 μM EDTA, 1% BSA). Washes can be done with 2×SSC, 0.1% SDS at 65° C. and then at 0.1×SSC, 0.1% SDS at 65° C.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, New York; and Ausubel et al., 1989, Current Protocols in Molecular Biology, Green Publishing Associates and Wiley Interscience, New York.

Alternatively, the labeled p101 nucleotide probe may be used to screen a genomic library derived from the organism of interest, again, using appropriately stringent conditions. The identification and characterization of human genomic clones is helpful for designing diagnostic tests and clinical protocols for treating hematopoietic lineage cell activation disorders in human patients. For example, sequences derived from regions adjacent to the intron/exon boundaries of the human gene can be used to design primers for use in amplification assays to detect mutations within the exons, introns, splice sites (e.g. splice acceptor and/or donor sites), etc., that can be used in diagnostics.

Further, a p101 gene homolog may be isolated from nucleic acid of the organism of interest by performing PCR using two degenerate oligonucleotide primer pools designed on the basis of amino acid sequences within the p101 gene product disclosed herein. The template for the reaction may be cDNA obtained by reverse transcription of mRNA prepared from, for example, human or non-human cell lines or cell types, such as neutrophils, known or suspected to express a p101 gene allele.

The PCR product may be subcloned and sequenced to ensure that the amplified sequences represent the sequences of a p101 gene. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular source (i.e., one known, or suspected, to express the p101 gene, such as, for example, neutrophils or other types of leukocytes). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

The p101 gene sequences may additionally be used to isolate mutant p101 gene alleles. Such mutant alleles may be isolated from individuals either known or proposed to have a genotype which contributes to the symptoms of hematopoietic lineage cell activation disorders such as inflammation. Mutant alleles and mutant allele products may then be utilized in the therapeutic and diagnostic systems described below. Additionally, such p101 gene sequences can be used to detect p101 gene regulatory (e.g., promoter or promotor/enhancer) defects which can affect hematopoietic lineage cell activation.

A cDNA of a mutant p101 gene may be isolated, for example, by using PCR, a technique which is well known to those of skill in the art. In this case, the first cDNA strand may be synthesized by hybridizing an oligo-dT oligonucleotide to mRNA isolated from cells known or suspected to be expressed in an individual putatively carrying the mutant p101 allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well-known to those of skill in the art. By comparing the DNA sequence of the mutant p101 allele to that of the normal p101 allele, the mutation(s) responsible for the loss or alteration of function of the mutant p101 gene product can be ascertained.

Alternatively, a genomic library can be constructed using DNA obtained from an individual suspected of or known to carry the mutant p101 allele, or a cDNA library can be constructed using RNA from a cell type known, or suspected, to express the mutant p101 allele. The normal p101 gene or any suitable fragment thereof may then be labeled and used as a probe to identify the corresponding mutant p101 allele in such libraries. Clones containing the mutant p101 gene sequences may then be purified and subjected to sequence analysis according to methods well known to those of skill in the art.

Additionally, an expression library can be constructed utilizing cDNA synthesized from, for example, RNA isolated from a cell type known, or suspected, to express a mutant p101 allele in an individual suspected of or known to carry such a mutant allele. In this manner, gene products made by the putatively mutant cell type may be expressed and screened using standard antibody screening techniques in conjunction with antibodies raised against the normal p101 gene product, as described, below, in Section 5.3. (For screening techniques, see, for example, Harlow, E. and Lane, eds., 1988, "Antibodies: A Laboratory Manual", Cold Spring Harbor Press, Cold Spring Harbor.) Additionally, screening can be accomplished by screening with labeled fusion proteins, such as, for example, the (EE)120 or the myc120 fusion proteins. In cases where a p101 mutation results in an expressed gene product with altered function (e.g., as a result of a missense or a frameshift mutation), a polyclonal set of antibodies to p101 regulatory subunit are likely to cross-react with the mutant p101 regulatory subunit gene product. Library clones detected via their reaction with such labeled antibodies can be purified and subjected to sequence analysis according to methods well known to those of skill in the art.

The invention also encompasses nucleotide sequences that encode mutant p101 regulatory subunits, peptide fragments of the p101 regulatory subunit, truncated p101 regulatory subunits, and p101 regulatory subunit fusion proteins. These include, but are not limited to nucleotide sequences encoding mutant p101 regulatory subunits described in section 5.2 infra; polypeptides or peptides corresponding to the catalytic binding, or Gβγ subunit binding domains of the p101 regulatory subunit or portions of these domains; truncated p101 regulatory subunits in which one or two of the domains is deleted, or a truncated, nonfunctional p101 regulatory subunit. Nucleotides encoding fusion proteins may include but are not limited to full length p101 regulatory subunit, truncated p101 regulatory subunit or peptide fragments of p101 regulatory subunit fused to an unrelated protein or peptide, such as for example, an epitope tag which aids in purification or detection of the resulting fusion protein; or an enzyme, fluorescent protein, luminescent protein which can be used as a marker.

The invention also encompasses (a) DNA vectors that contain any of the foregoing p101 regulatory subunit coding sequences and/or their complements (i.e., antisense); (b) DNA expression vectors that contain any of the foregoing p101 regulatory subunit coding sequences operatively associated with a regulatory element that directs the expression of the coding sequences; and (c) genetically engineered host cells that contain any of the foregoing p101 regulatory subunit coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to the baculovirus promoter, cytomegalovirus hCMV immediate early gene promoter, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

Finally, the invention also encompasses nucleotides encoding p120 subunit proteins including the newly described carboxyl terminus of this catalytic subunit, deletion variants of p120 subunit proteins, nucleotides which hybridize to these nucleotides under highly stringent conditions and which encode functionally equivalent products, including the cDNA clone pCMV3mycp120 deposited with the ATCC under accession number 97637, allelic variants of p120 (e.g., mutant alleles or the naturally occurring alleles such as the allelic variation at amino acid residue 483), and equivalent p120 nucleotides from different organisms isolated as described above for the p101 nucleotides of the invention. Additionally, the invention encompasses expression vectors and host cells for the recombinant production of p120.

5.2 p101 AND p120 PROTEINS AND POLYPEPTIDES p101 regulatory subunit and p120 catalytic subunit, polypeptides and peptide fragments, mutated, truncated or deleted forms of the p101 regulatory subunit and/or p101 regulatory subunit fusion proteins and the p120 catalytic subunit and/or p120 catalytic subunit fusion proteins can be prepared for a variety of uses, including but not limited to the generation of antibodies, as reagents in diagnostic assays, the identification of other cellular gene products involved in the regulation of hematopoietic lineage cell activation, as reagents in assays for screening for compounds that can be used in the treatment of hematopoietic lineage cell activation disorders, and as pharmaceutical reagents useful in the treatment of hematopoietic lineage cell activation disorders related to Gβγ-activated PI3K.

FIG. 2 shows the amino acid sequence of a porcine p101 regulatory subunit protein. FIG. 4 shows the amino acid sequence of a human p120 catalytic subunit protein. The broken line underscores the region of p120 which diverges from the published sequences of the PI3K catalytic subunits p110α, p110β, and p110©.

The p101 regulatory subunit sequence begins with a methionine in a DNA sequence context consistent with a translation initiation site. The predicted molecular mass of porcine p101 regulatory subunit is 97 kD.

The p101 regulatory subunit amino acid sequences of the invention include the amino acid sequence shown in FIG. 2 (SEQ. ID. No:2), or the amino acid sequence encoded by the cDNA clone pCMV3mycp101, as deposited with the ATCC. Further, p101 regulatory subunits of other species are encompassed by the invention. In fact, any p101 regulatory subunit protein encoded by the p101 nucleotide sequences described above, are within the scope of the invention.

The p120 catalytic subunit amino acid sequences of the invention include the cDNA clone pCMV3mycp120, as deposited with the ATCC. The invention also encompasses p120 catalytic subunits of other species, and the p120 proteins encoded by the p120 nucleotide sequences described above in the previous section.

The invention also encompasses proteins that are functionally equivalent to the p101 regulatory subunit encoded by the nucleotide sequences described above, as judged by any of a number of criteria, including but not limited to the ability to bind catalytic subunit, the binding affinity for catalytic subunit, the ability to stimulate PI3K activity of the catalytic subunit in response to activated trimeric G proteins, the resulting biological effect of catalytic subunit binding and response to activation of trimeric G proteins, e.g., signal transduction, a change in cellular metabolism (e.g., generation of PtdIns(3,4,5)$P_3$) or change in phenotype when the p101 regulatory subunit equivalent is present in an appropriate cell type (such as the superoxide burst in neutrophils). Such functionally equivalent p101 regulatory subunit proteins include but are not limited to additions or substitutions of amino acid residues within the amino acid sequence encoded by the p101 nucleotide sequences described, above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, non-polar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Similarly, the invention also encompasses functional equivalents of p120 protein, as described above.

While random mutations can be made to p101 DNA (using random mutagenesis techniques well known to those skilled in the art) and the resulting mutant p101 regulatory subunits tested for activity, site-directed mutations of the p101 coding sequence can be engineered (using site-directed mutagenesis techniques well known to those skilled in the art) to generate mutant p101 regulatory subunits with increased function, e.g., higher binding affinity for catalytic subunit, and/or greater signalling capacity; or decreased function, e.g., lower binding affinity for catalytic subunit, and/or decreased signal transduction capacity.

For example, porcine p101 amino acid sequence may be aligned with that of human p101 regulatory subunit. Mutant p101 regulatory subunits can be engineered so that regions of interspecies identity are maintained, whereas the variable residues are altered, e.g., by deletion or insertion of an amino acid residue(s) or by substitution of one or more different amino acid residues. Conservative alterations at the variable positions can be engineered in order to produce a mutant p101 regulatory subunit that retains function; e.g., catalytic subunit binding affinity or activated G protein transduction capability or both. Non-conservative changes can be engineered at these variable positions to alter function, e.g., catalytic subunit binding affinity or signal transduction capability, or both. Alternatively, where alteration of function is desired, deletion or non-conservative alterations of the conserved regions can be engineered. One of skill in the art may easily test such mutant or deleted p101 regulatory subunits for these alterations in function using the teachings presented herein.

Other mutations to the p101 coding sequence can be made to generate p110 regulatory subunits that are better suited for expression, scale up, etc. in the host cells chosen. For example, the triplet code for each amino acid can be modified to conform more closely to the preferential codon usage of the host cell's translational machinery.

Peptides corresponding to one or more domains (or a portion of a domain) of the p101 regulatory subunit (e.g., the p120 binding domain, the G protein interacting domain, or the domains defined by amino acid residues from about 1 to 150, 151 to 300, 301 to 450, 451 to 600, 601 to 732, and 733 to 877), truncated or deleted p101 regulatory subunits (e.g., p101 regulatory subunit in which portions of one or more of the above domains are deleted) as well as fusion proteins in which the full length p101 regulatory subunit, a p101 regulatory subunit peptide or truncated p101 regulatory subunit is fused to an unrelated protein are also within the scope of the invention and can be designed on the basis of the p101 nucleotide and p101 regulatory subunit amino acid sequences disclosed in this Section and above. Such fusion proteins include but are not limited to fusions to an epitope tag (such as is exemplified in the Examples below); or fusions to an enzyme, fluorescent protein, or luminescent protein which provide a marker function.

While the p101 regulatory subunit polypeptides and peptides can be chemically synthesized (e.g., see Creighton, 1983, Proteins: Structures and Molecular Principles, W. H. Freeman & Co., New York), large polypeptides derived from the p101 regulatory subunit and the full length p101 regulatory subunit itself may advantageously be produced by recombinant DNA technology using techniques well known in the art for expressing nucleic acid containing p101 gene sequences and/or coding sequences. Such methods can be used to construct expression vectors containing the p101 nucleotide sequences described above and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding p101 nucleotide sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the p101 nucleotide sequences of the invention. Where the p101 regulatory subunit peptide or polypeptide is a soluble derivative the peptide or polypeptide can be recovered from the culture, i.e., from the host cell in cases where the p101 regulatory subunit peptide or polypeptide is not secreted, and from the culture media in cases where the p101 regulatory subunit peptide or polypeptide is secreted by the cells. However, such engineered host cells themselves may be used in situations where it is important not only to retain the structural and functional characteristics of the p101 regulatory subunit, but to assess biological activity, e.g., in drug screening assays.

The expression systems that may be used for purposes of the invention include but are not limited to microorganisms such as bacteria (e.g., *E. coli*, *B. subtilis*) transformed with recombinant bacteriophage DNA, plasmid DNA or cosmid DNA expression vectors containing p101 nucleotide sequences; yeast (e.g., Saccharomyces, Pichia) transformed with recombinant yeast expression vectors containing the p101 nucleotide sequences; insect cell systems infected with recombinant virus expression vectors (e.g., baculovirus) containing the p101 sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing p101 nucleotide sequences; or mammalian cell systems (e.g., COS, CHO, BHK, 293, 3T3, U937) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the p101 gene product being expressed. For example, when a large quantity of such a protein is to be produced, for the generation of pharmaceutical compositions of p101 regulatory subunit protein or for raising antibodies to the p101 regulatory subunit protein, for example, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the p101 coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). If the inserted sequence encodes a relatively small polypeptide (less than 25 kD), such fusion proteins are generally soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety. Alternatively, if the resulting fusion protein is insoluble and forms inclusion bodies in the host cell, the inclusion bodies may be purified and the recombinant protein solubilized using techniques well known to one of skill in the art.

In an insect system, *Autogralha californica* nuclear polyhidrosis virus (AcNPV) may be used as a vector to express foreign genes. (E.g., see Smith et al., 1983, J. Virol. 46: 584; Smith, U.S. Pat. No. 4,215,051). In a specific embodiment described below, Sf9 insect cells are infected with a baculovirus vectors expressing either a 6× HIS-tagged p120 construct, or an (EE)-tagged p101 construct.

In mammalian host cells, a number of viral-based expression systems may be utilized. Specific embodiments described more fully below express tagged p101 or p120 cDNA sequences using a CMV promoter to transiently express recombinant protein in U937 cells or in Cos-7 cells. Alternatively, retroviral vector systems well known in the art may be used to insert the recombinant expression construct into host cells. For example, retroviral vector systems for transducing hematopoietic cells are described in published PCT applications WO 96/09400 and WO 94/29438.

In cases where an adenovirus is used as an expression vector, the p101 nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the p101 gene product in infected hosts. (E.g., See Logan & Shenk, 1984, Proc. Natl. Acad. Sci. USA 81:3655–3659). Specific initiation signals may also be required for efficient translation of inserted p101 nucleotide sequences. These signals include the ATG initiation codon and adjacent sequences. In cases where an entire p101 gene or cDNA, including its own initiation codon and adjacent sequences, is inserted into the appropriate expression vector, no additional translational control signals may be needed. However, in cases where only a portion of the p101 coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript may be used. Such mammalian host cells include but are not limited to CHO, VERO, BHK, HeLa, COS, MDCK, 293, 3T3, WI38, and U937 cells.

For long-term, high-yield production of recombinant proteins, stable expression is preferred. For example, cell lines which stably express the p101 sequences described above may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the oll gene product. Such engineered cell lines may be particularly useful in screening and evaluation of compounds that affect the endogenous activity of the p101 gene product.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk$^-$, hgprt$^-$or aprt$^-$cells, respectively. Also, antimetabolite resistance can be used as the basis of selection for the following genes: dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147).

The p101 gene products can also be expressed in transgenic animals. Animals of any species, including, but not limited to, mice, rats, rabbits, guinea pigs, pigs, micro-pigs, goats, and non-human primates, e.g., baboons, monkeys, and chimpanzees may be used to generate p101 transgenic animals.

Any technique known in the art may be used to introduce the p101 transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der-Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the p101 transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232–6236). The regulatory sequences required for such a cell-type specific activation will depend upon the particular cell type of interest, and will be apparent to those of skill in the art. When it is desired that the p101 gene transgene be integrated into the chromosomal site of the endogenous p101 gene, gene targeting is preferred. Briefly, when such a technique is to be utilized, vectors containing some nucleotide sequences homologous to the endogenous p101 gene are designed for the purpose of integrating, via homologous recombination with chromosomal sequences, into and disrupting the function of the nucleotide sequence of the endogenous p101 gene. In this way, the expression of the endogenous p101 gene may also be eliminated by inserting non-functional sequences into the endogenous gene. The transgene may also be selectively introduced into a particular cell type, thus inactivating the endogenous p101 gene in only that cell type, by following, for example, the teaching of Gu et al. (Gu et al., 1994, Science 265: 103–106). The regulatory sequences required for such a cell-type specific inactivation will depend upon the particular cell type of interest, and will be apparent to those of skill in the art.

Once transgenic animals have been generated, the expression of the recombinant p101 gene may be assayed utilizing standard techniques. Initial screening may be accomplished by Southern blot analysis or PCR techniques to analyze animal tissues to assay whether integration of the transgene has-taken place. The level of mRNA expression of the transgene in the tissues of the transgenic animals may also be assessed using techniques which include but are not limited to Northern blot analysis of cell type samples obtained from the animal, in situ hybridization analysis, and RT-PCR. Samples of p101 gene-expressing tissue, may also be evaluated immunocytochemically using antibodies specific for the p101 transgene product, as described below.

5.3 ANTIBODIES TO p101 AND p120 PROTEINS

Antibodies that specifically recognize one or more epitopes of p101 regulatory subunit, or epitopes of conserved variants of p101 regulatory subunit, or peptide fragments of the p101 regulatory subunit are also encompassed by the invention. Also encompassed by the invention are antibodies which recognize one or more epitopes of the p120 protein, particularly, the novel carboxyl terminus. Such antibodies include but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention may be used, for example, in the detection of the p101 regulatory subunit or p120 in a biological sample and may, therefore, be utilized as part of a diagnostic or prognostic technique whereby patients may be tested for abnormal amounts of these proteins. Such antibodies may also be utilized in conjunction with, for example, compound screening schemes, as described, below, in Section 5.5, for the evaluation of the effect of test compounds on expression-and/or activity of the p101 or p120 gene products. Additionally, such antibodies can be used in conjunction with the gene therapy techniques described, below, in Section 5.6, to, for example, evaluate the normal and/or engineered p101 regulatory subunit-expressing cells prior to their introduction into the patient. Such antibodies may additionally be used as a method for the inhibition of abnormal p101 regulatory subunit or p120 activity. Thus, such antibodies may, therefore, be utilized as part of inflammatory disorder treatment methods. For the production of antibodies, various host animals may be immunized by injection with the p101 regulatory subunit, a p101 regulatory subunit peptide, truncated p101 regulatory subunit polypeptides, functional equivalents of the p101 regulatory subunit or mutants of the p101 regulatory subunit. Additionally, host animals may be immunized by injection with p120 catalytic subunit or peptides of the p120 subunit. Such host animals may include but are not limited to rabbits, mice, and rats, to name but a few. Various adjutants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrbphenol, and potentially useful human adjutants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technicue which provides for the production of antibody molecules by continuous cell lines in culture. These include, but are not limited to, the hybridoma technique of Kohler and Milstein, (1975, Nature 256:495–497; and U.S. Pat. No. 4, 376, 110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci. USA, 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a porcine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against p101 gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to the p101 regulatory subunit or the p120 catalytic subunit can, in turn, be utilized to generate anti-idiotype antibodies that "mimic" the p101 regulatory subunit or p120 subunit, respectively, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to the p101 regulatory subunit and competitively inhibit the binding of catalytic subunit to the p101 regulatory subunit can be used to generate anti-idiotypes that "mimic" the p101 regulatory subunit and, therefore, bind and neutralize catalytic subunit. Such neutralizing anti-idiotypes or Fab fragments of such anti-idiotypes can be used in therapeutic regimens to neutralize catalytic subunit and reduce inflammation.

5.4 DIAGNOSIS OF HEMATOPOIETIC CELL ACTIVATION DISORDERS

A variety of methods can be employed for the diagnostic and prognostic evaluation of hematopoietic lineage cell activation disorders, including inflammatory disorders, and for the identification of subjects having a predisposition to such disorders.

Such methods may, for example, utilize reagents such as the p101 and p120 nucleotide sequences described above, and p101 regulatory subunit and p120 antibodies, as described, in Section 5.3. Specifically, such reagents may be used, for example, for: (1) the detection of the presence of 101 or p120 gene mutations, or the detection of either over- or under-expression of p101 or p120 mRNA relative to the non-hematopoietic lineage cell activation disorder state; (2) the detection of either an over- or an under-abundance of p101 or p120 gene product relative to the non-hematopoietic lineage cell activation disorder state; and (3) the detection of perturbations or abnormalities in the signal transduction pathway mediated by p101 regulatory subunit and p120 catalytic subunit.

The methods described herein may be performed, for example, by utilizing pre-packaged diagnostic kits comprising at least one specific p101 or p120 nucleotide sequence or p101 or p120 regulatory subunit antibody reagent described herein, which may be conveniently used, e.g., in clinical settings, to diagnose patients exhibiting hematopoietic lineage cell activation disorder abnormalities.

For the detection of p101 or p120 mutations, any nucleated cell can be used as a starting source for genomic nucleic acid. For the detection of p101 or p120 gene expression or p101 or p120 gene products, any cell type or tissue in which the p101 or p120 gene is expressed, such as, for example, neutrophil cells, may be utilized.

Nucleic acid-based detection techniques are described, below, in Section 5.4.1. Peptide detection techniques are described, below, in Section 5.4.2.

5.4.1 DETECTION OF THE p101 GENE AND TRANSCRIPTS

Mutations within the p101 or p120 genes can be detected by utilizing a number of techniques. Nucleic acid from any nucleated cell can be used as the starting point for such assay techniques, and may be isolated according to standard nucleic acid preparation procedures which are well known to those of skill in the art.

DNA may be used in hybridization or amplification assays of biological samples to detect abnormalities involving gene structure, including point mutations, insertions, deletions and chromosomal rearrangements. Such assays may include, but are not limited to, Southern analyses, single stranded conformational polymorphism analyses (SSCP), and PCR analyses.

Such diagnostic methods for the detection of p101 or p120 gene-specific mutations can involve for example, contacting and incubating nucleic acids including recombinant DNA molecules, cloned genes or degenerate variants thereof, obtained from a sample, e.g., derived from a patient sample or other appropriate cellular source, with one or more labeled nucleic acid reagents including recombinant DNA molecules, cloned genes or degenerate variants thereof, as described above, under conditions favorable for the specific annealing of these reagents to their complementary sequences within the p101 or p120 gene. Preferably, the lengths of these nucleic acid reagents are at least 15 to 30 nucleotides. After incubation, all non-annealed nucleic acids are removed from the nucleic acid molecule hybrid. The presence of nucleic acids which have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described above are easily removed. Detection of the remaining, annealed, labeled p101 or p120 nucleic acid reagents is accomplished using standard techniques well-known to those in the art. The p101 or p120 gene sequences to which the nucleic acid reagents have annealed can be compared to the annealing pattern expected from a normal gene sequence in order to determine whether a gene mutation is present.

Alternative diagnostic methods for the detection of p101 or p120 gene specific nucleic acid molecules, in patient samples or other appropriate cell sources, may involve their amplification, e.g., by PCR (the experimental embodiment set forth in Mullis, K. B., 1987, U.S. Pat. No. 4,683,202), followed by the detection of the amplified molecules using techniques well known to those of skill in the art. The resulting amplified sequences can be compared to those which would be expected if the nucleic acid being amplified contained only normal copies of the p101 or p120 gene in order to determine whether a gene mutation exists.

Additionally, well-known genotyping techniques can be performed to identify individuals carrying p101 or p120 gene mutations. Such techniques include, for example, the use of restriction fragment length polymorphisms (RFLPs), which involve sequence variations in one of the recognition sites for the specific restriction enzyme used.

The level of p101 or p120 gene expression can also be assayed by detecting and measuring p101 or p120 transcription. For example, RNA from a cell type or tissue known, or suspected to express the p101 or p120 gene, such as hematopoietic lineage cells, especially myeloid cells and platelets, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the p101 or p120 gene. Such analyses may reveal both quantitative and qualitative aspects of the expression pattern of the p101 or p120 gene, including activation or inactivation of p101 or p120 gene expression.

5.4.2 DETECTION OF THE p101 GENE PRODUCTS

Antibodies directed against wild type or mutant p101 or p120 gene products or conserved variants or peptide fragments thereof, which are discussed, above, in Section 5.3, may also be used as hematopoietic lineage cell activation disorder diagnostics and prognostics, as described herein. Such diagnostic methods, may be used to detect abnormalities in the level of p101 or p120 gene expression, or abnormalities in the structure and/or temporal, tissue, cellular, or subcellular location of the p101 regulatory subunit, and may be performed in vivo or in vitro, such as, for example, on biopsy tissue.

The tissue or cell type to be analyzed will generally include those which are known, or suspected, to contain cells express the p101 or p120 gene, such as, for example, neutrophil cells which have infiltrated an inflamed tissue. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, New York), which is incorporated herein by reference in its entirety. The isolated cells can be derived from cell culture or from a patient. The analysis of cells taken from culture may be a necessary step in the assessment of cells that could be used as part of a cell-based gene therapy technique or, alternatively, to test the effect of compounds on the expression of the p101 or p120 gene.

For example, antibodies, or fragments of antibodies, such as those described, above, in Section 5.3, useful in the present invention may be used to quantitatively or qualitatively detect the presence of p101 or p120 gene products or conserved variants or peptide fragments thereof. This can be accomplished, for example, by immunofluorescence techniques employing a fluorescently labeled antibody (see below, this Section) coupled with light microscopic, flow cytometric, or fluorimetric detection.

The antibodies (or fragments thereof) or fusion or conjugated proteins useful in the present invention may, additionally, be employed histologically, as in immunofluorescence, immunoelectron microscopy or non-immuno assays, for in situ detection of p101 or p120 gene products or conserved variants or peptide fragments thereof, or for catalytic subunit binding (in the case of labeled catalytic subunit fusion protein).

In situ detection may be accomplished by removing a histological specimen from a patient, and applying thereto a labeled antibody or fusion protein of the present invention. The antibody (or fragment) or fusion protein is preferably applied by overlaying the labeled antibody (or fragment) onto a biological sample. Through the use of such a procedure, it is possible to determine not only the presence of the p101 or p120 gene product, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for p101 or 120 gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying p101 or p120 gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled p101 regulatory subunit or p120 subunit antibody or fusion protein. The solid phase support may then be washed with the buffer a second time to remove unbound antibody or fusion protein. The amount of bound label on solid support may then be detected by conventional means.

"Solid phase support or carrier" is intended to encompass any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of p101 regulatory subunit or p120 subunit antibody or fusion protein may be determined according to well known methods. Those skilled in the art will be able to determine operative and optimal assay conditions for each determination by employing routine experimentation.

With respect to antibodies, one of the ways in which the antibody can be detectably labeled is by linking the same to an enzyme and use in an enzyme immunoassay (EIA) (Voller, "The Enzyme Linked Immunosorbent Assay (ELISA)", 1978, Diagnostic Horizons 2:1–7, Microbiological Associates Quarterly Publication, Walkersville, Md.); Voller et al., 1978, J. Clin. Pathol. 31:507–520; Butler, 1981, Meth. Enzymol. 73:482–523; Maggio (ed.), 1980, Enzyme Immunoassay, CRC Press, Boca Raton, Fla., ; Ishikawa et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, , by radioactively labeling the antibodies or antibody fragments, it is possible to detect p101 regulatory subunit through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.5 SCREENING ASSAYS FOR COMPOUNDS THAT MODULATE G-PROTEIN ACTIVATED PI3K EXPRESSION OR ACTIVITY

The following assays are designed to identify compounds that interact with (e.g., bind to) p101 regulatory subunit or the p120 catalytic subunit, compounds that interact with (e.g., bind to) intracellular proteins that interact with p101 regulatory subunit and/or the p120 catalytic subunit, compounds that interfere with the interaction of p101 regulatory subunit with the p120 catalytic subunit or with other intracellular proteins involved in G protein stimulated PI3K mediated signal transduction, and to compounds which modulate the activity of p101 or p120 gene (i.e., modulate the level of p101 or i120 gene expression) or modulate the level of p101 or p120. Assays may additionally be utilized which identify compounds which bind to p101 or p120 gene regulatory sequences (e.g., promoter sequences) and which may modulate p101 or p120 gene expression. See e.g., Platt, K. A., 1994, J. Biol. Chem. 269:28558–28562, which is incorporated herein by reference in its entirety.

The compounds which may be screened in accordance with the invention include but are not limited to peptides, antibodies and fragments thereof, prostaglandins, lipids and other organic compounds (e.g., terpines, peptidomimetics) that bind to the p101 regulatory subunit or p120 catalytic subunit and either mimic the activity triggered by the natural ligand (i.e., agonists) or inhibit the activity triggered by the natural ligand (i.e., antagonists); as well as peptides, antibodies or fragments thereof, and other organic compounds that mimic the p101 regulatory subunit or the p120 catalytic subunit (or a portion thereof) and bind to and "neutralize" natural ligand.

Such compounds may include, but are not limited to, peptides such as, for example, soluble peptides, including but not limited to members of random peptide libraries (see, e.g., Lam, K. S. et al., 1991, Nature 354:82–84; Houghten, R. et al., 1991, Nature 354:84–86), and combinatorial chemistry-derived molecular library peptides made of D- and/or L-configuration amino acids, phosphopeptides (including, but not limited to members of random or partially degenerate, directed phosphopeptide libraries; see, e.g., Songyang, Z. et al., 1993, Cell 72:767–778); antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof); and small organic or inorganic molecules.

Other compounds which can be screened in accordance with the invention include but are not limited to small organic molecules that are able to gain entry into an appropriate cell (e.g., in the neutrophil) and affect the expression of the p101 or p120 gene or some other gene involved in the p101 regulatory subunit signal transduction pathway (e.g., by interacting with the regulatory region or transcription factors involved in gene expression); or such compounds that affect the activity of the p101 regulatory subunit, e.g., by inhibiting or enhancing the binding of p101 to the catalytic subunit of the PI3K or the binding of p101 to some other intracellular factor involved in the p101 regulatory subunit signal transduction pathway, such as, for example, Gβγ.

Computer modelling and searching technologies permit identification of compounds, or the improvement of already identified compounds, that can modulate p101 regulatory subunit or p120 catalytic subunit expression or activity. Having identified such a compound or composition, the active sites or regions are identified. Such active sites might typically be the binding partner sites, such as, for example, the interaction domains of the p120 catalytic subunit with p101 regulatory subunit itself. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modelling can be used to complete the structure or improve its accuracy. Any recognized modelling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential G protein activated PI3K modulating compounds.

Alternatively, these methods can be used to identify improved modulating compounds from an already known modulating compound or ligand. The composition of the known compound can be modified and the structural effects of modification can be determined using the experimental and computer modelling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of p120 catalytic subunit, p101 regulatory subunit, and related transduction and transcription factors will be apparent to those of skill in the art.

Examples of molecular modeling systems are the CHARMm and QUANTA programs (Polygen Corporation, Waltham, Mass.). CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modelling of drugs interactive with specific proteins, such as Rotivinen et al., 1988, Acta Pharmaceutical Fennica 97:159–166; Ripka, New Scientist 54–57 (June 16, 1988); McKinaly and Rossmann, 1989, Annu. Rev. Pharmacol. Toxiciol. 29:111–122; Perry and Davies, QSAR: Quantitative Structure-Activity Relationships in Drug Design pp. 189–193 (Alan R. Liss, Inc. 1989); Lewis and Dean, 1989, Proc. R. Soc. Lond. 236:125–140 and 141–162; and, with respect to a model receptor for nucleic acid components, Askew et al., 1989, J. Am. Chem. Soc. 111:1082–1090. Other computer programs that screen and graphically depict chemicals are available from companies such as DioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Compounds identified via assays such as those described herein may be useful, for example, in elaborating the biological function of the p101 or p120 gene product, and for ameliorating hematopoietic lineage cell activation disorders. Assays for testing the effectiveness of compounds, identified by, for example, techniques such as those described in Section 5.5.1 through 5.5.3, are discussed, below, in Section 5.5.4.

5.5.1 In vitro SCREENING ASSAYS FOR COMPOUNDS THAT BIND TO p101 REGULATORY SUBUNIT In vitro systems may be designed to identify compounds capable of interacting with (e.g., binding to) p101 regulatory subunit or p120 catalytic subunit. Compounds identified may be useful, for example, in modulating the activity of wild type and/or mutant p101 or p120 gene products; may be utilized in screens for identifying compounds that disrupt normal p101 regulatory subunit/catalytic subunit interactions; or may in themselves disrupt such interactions.

The principle of the assays used to identify compounds that bind to the p101 regulatory subunit involves preparing a reaction mixture of the p101 regulatory subunit and the test compound under conditions and for a time sufficient to allow the two components to interact and bind, thus forming a complex which can be removed and/or detected in the reaction mixture. The p101 regulatory subunit species used can vary depending upon the goal of the screening assay. For example, where agonists of the natural ligand are sought, the full length p101 regulatory subunit, or a fusion protein containing the p101 regulatory subunit fused to a protein or polypeptide that affords advantages in the assay system (e.g., labeling, isolation of the resulting complex, etc.) can be utilized.

The screening assays can be conducted in a variety of ways. For example, one method to conduct such an assay would involve anchoring the p101 regulatory subunit protein, polypeptide, peptide or fusion protein or the test substance onto a solid phase and detecting p101 regulatory subunit/test compound complexes anchored on the solid phase at the end of the reaction. In one embodiment of such a method, the p101 regulatory subunit reactant may be anchored onto a solid surface, and the test compound, which is not anchored, may be labeled, either directly or indirectly. In another embodiment of the method, a p101 regulatory subunit protein anchored on the solid phase is complexed with labeled catalytic subunit such as p120. Then, a test compound could be assayed for its ability to disrupt the association of the p101/p120 complex.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for p101 regulatory subunit protein, polypeptide, peptide or fusion protein, or the catalytic subunit protein or fusion protein, or the test compound to anchor any complexes formed in solution, and a labeled antibody specific for the other component of the possible complex to detect anchored complexes.

5.5.2 ASSAYS FOR INTRACELLULAR PROTEINS THAT INTERACT WITH THE p101 OR p120 PROTEINS

Any method suitable for detecting protein-protein interactions may be employed for identifying intracellular proteins that interact with p101 regulatory subunit and/or the catalytic subunit p120. Among the traditional methods which may be employed are co-immunoprecipitation, crosslinking and co-purification through gradients or chromatographic columns of cell lysates or proteins obtained from cell lysates and the p101 regulatory subunit to identify proteins in the lysate that interact with the p101 regulatory subunit. For these assays, the p101 regulatory subunit component used can be a full length p101 regulatory subunit, or a truncated peptide. Similarly, the component may be a p120 catalytic subunit, or a complex of the p101 regulatory subunit with the p120 catalytic subunit. Once isolated, such an intracellular protein can be identified and can, in turn, be used, in conjunction with standard techniques, to identify proteins with which it interacts. For example, at least a portion of the amino acid sequence of an intracellular protein which interacts with the p101 regulatory subunit, PI3K (p101/p120 complex), or p120 catalytic subunit, can be ascertained using techniques well known to those of skill in the art, such as via the Edman degradation technique. (See, e.g., Creighton, 1983, "Proteins: Structures and Molecular Principles", W. H. Freeman & Co., New York, pp. 34–49). The amino acid sequence obtained may be used as a guide for the generation of oligonucleotide mixtures that can be used to screen for gene sequences encoding such intracellular proteins. Screening may be accomplished, for example, by standard hybridization or PCR techniques. Techniques for the generation of oligonucleotide mixtures and the screening are well-known. (See, e.g., Ausubel, supra., and PCR Protocols: A Guide to Methods and Applications, 1990, Innis, M. et al., eds. Academic Press, Inc., New York).

Additionally, methods may be employed which result in the simultaneous identification of genes which encode the intracellular proteins interacting with p101 regulatory subunit and/or the p120 catalytic subunit and/or the PI3K. These methods include, for example, probing expression, libraries, in a manner similar to the well known technique of antibody probing of λgt11 libraries, using labeled p101 regulatory subunit protein, or a p101 regulatory subunit polypeptide, peptide or fusion protein, e.g., a p101 regulatory subunit polypeptide or p101 regulatory subunit domain fused to a marker (e.g., an enzyme, fluor, luminescent protein, or dye), or an Ig-Fc domain.

One method which detects protein interactions in vivo, the two-hybrid system, is described in detail for illustration only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one plasmid consists of nucleotides encoding the DNA-binding domain of a transcription activator protein fused to a p101 nucleotide sequence encoding p101 regulatory subunit, a p101 regulatory subunit polypeptide, peptide or fusion-protein, and the other plasmid consists of nucleotides encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast Saccharomvces cerevisiae that contains a reporter gene (e.g., HBS or lacZ) whose regulatory region contains the transcription activator's binding site. Either hybrid protein alone cannot activate transcription of the reporter gene; the DNA-binding domain hybrid cannot because it does not provide activation function, and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, p101 regulatory subunit may be used as the bait gene product. Total genomic or cDNA sequences are fused to the DNA encoding an activation domain. This library and a plasmid encoding a hybrid of a bait 101 gene product fused to the DNA-binding domain are cotransformed into a yeast reporter strain, and the resulting transformants are screened for those that express the reporter gene. For example, and not by way of limitation, a bait p101 gene sequence, such as the open reading frame of p101 (or a domain of p101), as depicted in FIG. 1 can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait p101 gene product are to be detected can be made using methods routinely practiced in the art. According to the particular system described herein, for example, the cDNA fragments can be inserted into a vector such that they are translationally fused to the transcriptional activation domain of GAL4. This library can be co-transfected along with the bait p101 gene-GAL4 fusion plasmid into a yeast strain which contains a lacZ gene driven by a promoter which contains GAL4 activation sequence. A cDNA encoded protein, fused to GAL4 transcriptional activation domain, that interacts with bait p101 gene product will reconstitute an active GAL4 protein and thereby drive expression of the HIS3 gene. Colonies which express HIS3 can be detected by their growth on petri dishes containing semi-solid agar based media lacking histidine. The cDNA can then be purified from these strains, and used to produce and isolate the bait p101 gene-interacting protein using techniques routinely practiced in the art.

5.5.3 ASSAYS FOR COMPOUNDS THAT INTERFERE WITH p101 REGULATORY SUBUNIT/ INTRACELLULAR MACROMOLECULE INTERACTION

The macromolecules that interact with the p101 regulatory subunit are referred to, for purposes of this discussion, as "binding partners". These binding partners are likely to be involved in the p101 regulatory subunit signal transduction pathway, and therefore, in the role of p101 regulatory subunit in hematopoietic lineage cell activation regulation. Known binding partners are catalytic subunits of the PI3K kinase such as p120, p117, and perhaps certain p110 proteins. Other binding partners are likely to be activated trimeric G proteins such as Gβγ subunits, and or lipids. Therefore, it is desirable to identify compounds that interfere with or disrupt the interaction of such binding partners with p101 which may be useful in regulating the activity of the p101 regulatory subunit and thus control hematodoietic lineage cell activation disorders associated with p101 regulatory subunit activity.

The basic principle of the assay systems used to identify compounds that interfere with the interaction between the p101 regulatory subunit and its binding partner or partners involves preparing a reaction mixture containing p101 regulatory subunit protein, polypeptide, peptide or fusion protein as described in Sections 5.5.1 and 5.5.2 above, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the p101 regulatory subunit moiety and its binding partner. Control reaction mixtures are incubated without the test compound or with a placebo. The formation of any complexes between the p101 regulatory subunit moiety and the binding partner is then detected. The formation of a complex in the control reaction, but not in the reaction mixture containing the test compound, indicates that the compound interferes with the interaction of the p101 regulatory subunit and the interactive binding partner. Additionally, complex formation within reaction mixtures containing the test compound and normal p101 regulatory subunit protein may also be compared to complex formation within reaction mixtures containing the test compound and a mutant p101 regulatory subunit. This comparison may be important in those cases wherein it is desirable to identify compounds that disrupt interactions of mutant but not normal p101 regulatory subunits.

The assay for compounds that interfere with the interaction of the p101 regulatory subunit and binding partners can be conducted in a heterogeneous or homogeneous format. Heterogeneous assays involve anchoring either the p101 regulatory subunit moiety product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance; i.e., by adding the test substance to the reaction mixture prior to or simultaneously with the p101 regulatory subunit moiety and interactive binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the p101 regulatory subunit moiety or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the p101 or p120 gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the p101 regulatory subunit moiety and the interactive binding partner is prepared in which either the p101 regulatory subunit or its binding partners is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt p101 regulatory subunit/intracellular binding partner interaction can be identified.

In a particular embodiment, a p101 regulatory subunit fusion can be prepared for immobilization. For example, the p101 regulatory subunit or a peptide fragment, e.g., corresponding to the CD, can be fused to a glutathione-S-transferase (GST) gene using a fusion vector, such as pGEX-5X -1, in such a manner that its binding activity is maintained in the resulting fusion protein. The interactive binding partner can be purified and used to raise a monoclonal antibody, using methods routinely practiced in the art and described above, in Section 5.3. This antibody can be labeled with the radioactive isotope $^{125}$I, for example, by methods routinely practiced in the art. In a heterogeneous assay, e.g., the GST-p101 regulatory subunit fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the p101 or p120 gene product and the interactive binding partner can be detected by measuring the amount of radioactivity that remains associated with the glutathione-agarose beads. A successful inhibition of the interaction by the test compound will result in a decrease in measured radioactivity.

Alternatively, the GST-p101 regulatory subunit fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the p101 regulatory subunit/binding partner interaction can be detected by adding the labeled antibody and measuring the radioactivity associated with the beads.

In another embodiment of the invention, these same techniques can be employed using peptide fragments that correspond to the binding domains of the p101 regulatory subunit and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

For example, and not by way of limitation, a p101 gene product can be anchored to a solid material as described, above, by making a GST-p101 regulatory subunit fusion protein and allowing it to bind to glutathione agarose beads. The interactive binding partner can be labeled with a radioactive isotope, such as $^{35}S$, and cleaved with a proteolytic enzyme such as trypsin. Cleavage products can then be added to the anchored GST-p101 fusion protein and allowed to bind. After washing away unbound peptides, labeled bound material, representing the intracellular binding partner binding domain, can be eluted, purified, and analyzed for amino acid sequence by well-known methods. Peptides so identified can be produced synthetically or fused to appropriate facilitative proteins using recombinant DNA technology.

5.5.4 ASSAYS FOR IDENTIFICATION OF COMPOUNDS THAT AMELIORATE INFLAMMATORY DISORDERS

Compounds, including but not limited to binding compounds identified via assay techniques such as those described, above, in Sections 5.5.1 through 5.5.3, can be tested for the ability to ameliorate immune system disorder symptoms, including inflammation. The assays described above can identify compounds which affect p101 regulatory subunit activity (e.g., compounds that bind to the p101 regulatory subunit, inhibit binding of the natural ligands, and either activate signal transduction (agonists) or block activation (antagonists), and compounds that bind to a natural ligand of the p101 regulatory subunit and neutralize the ligand activity); or compounds that affect p101 or p120 gene activity (by affecting p101 or p120 gene expression, including molecules, e.g., proteins or small organic molecules, that affect or interfere with splicing events so that expression of the full length or the truncated form of the p101 regulatory subunit can be modulated). However, it should be noted that the assays described herein can also identify compounds that modulate p101 regulatory subunit signal transduction (e.g., compounds which affect downstream signaling events, such as inhibitors or enhancers of activities which participate in transducing the PtdIns(4,5)$P_3$ signal which is generated by catalytic subunit binding to the p101 regulatory subunit). The identification and use of such compounds which affect another step in the p110 regulatory subunit signal transduction pathway in which the p101 or p120 gene and/or p101 or p120 gene product is involved and, by affecting this same pathway may modulate the effect of p101 regulatory subunit on the development of hematopoietic lineage cell activation disorders are within the scope of the invention. Such compounds can be used as part of a therapeutic method for the treatment of hematopoietic lineage cell activation disorders.

The invention encompasses cell-based and animal model-based assays for the identification of compounds exhibiting such an ability to ameliorate hematopoietic lineage cell activation disorder symptoms. Such cell-based assay systems can also be used as the standard to assay for purity and potency of the natural ligand, catalytic subunit, including recombinantly or synthetically produced catalytic subunit and catalytic subunit mutants.

Cell-based systems can be used to identify compounds which may act to ameliorate hematopoietic lineage cell activation disorder symptoms. Such cell systems can include, for example, recombinant or non-recombinant cells, such as, cell lines, which express the p101 and/or p120 gene. For example leukocyte cells, or cell lines derived from leukocyte cells can be used. In addition, expression host cells (e.g., COS cells, CHO cells, fibroblasts, Sf9 cells) genetically engineered to express a functional p101/p120 PI3K and to respond to activation by the natural ligand G$\beta\gamma$ subunits, e.g., as measured by a chemical or phenotypic change, induction of another host cell gene, change in intracellular messenger levels (e.g., PtdIns(3,4,5)$P_3$, etc.), can be used as an end point in the assay.

In utilizing such cell systems, cells may be exposed to a compound suspected of exhibiting an ability to ameliorate hematopoietic lineage cell activation disorder symptoms, at a sufficient concentration and for a time sufficient to elicit such an amelioration of hematopoietic lineage cell activation disorder symptoms in the exposed cells. After exposure, the cells can be assayed to measure alterations in the expression of the p101 or p120 gene, e.g., by assaying cell lysates for p101 or p120 mRNA transcripts (e.g., by Northern analysis) or for p101 or p120 protein expressed in the cell; compounds which regulate or modulate expression of the p101 or p120 gene are valuable candidates as therapeutics. Alternatively, the cells are examined to determine whether one or more hematopoietic lineage cell activation disorder-like cellular phenotypes has been altered to resemble a more normal or more wild type phenotype, or a phenotype more likely to produce a lower incidence or severity of disorder symptoms. Still further, the expression and/or activity of components of the signal transduction pathway of which p101 regulatory subunit is a part, or the activity of the p101 regulatory subunit signal transduction pathway itself can be assayed.

For example, after exposure of the cells, cell lysates can be assayed for the presence of increased levels of the second messenger PtdIns(3,4,5)$P_3$, compared to lysates derived from unexposed control cells. The ability of a test compound to inhibit production of second messenger in these assay systems indicates that the test compound inhibits signal transduction initiated by p101 regulatory subunit activation. The cell lysates can be readily assayed using anion-exchange HPLC. Alternatively, levels of superoxide production or $O_2$ may be assayed by monitoring chemiluminescence from horseradish-peroxidase catalyzed luminol oxidation as described in Wymann et al., 1987, Anal. Biochem. 165:371–378, incorporated herein by reference in its entirety. Finally, a change in cellular adhesion of intact cells may be assayed using techniques well known to those of skill in the art.

In addition, animal-based hematopoietic lineage cell activation disorder systems, which may include, for example, mice, may be used to identify compounds capable of ameliorating hematopoietic lineage cell activation disorder-like symptoms. Such animal models may be used as test systems for the identification of drugs, pharmaceuticals, therapies and interventions which may be effective in treating such disorders. For example, animal models may be exposed to a compound, suspected of exhibiting an ability to ameliorate hematopoietic lineage cell activation disorder symptoms, at a sufficient concentration and for a time sufficient to elicit such an amelioration of hematopoietic lineage cell activation disorder symptoms in the exposed animals. The response of the animals to the exposure may be monitored by assessing the reversal of disorders associated with hematopoietic lineage cell activation disorders such as inflammation. With regard to intervention, any treatments which reverse any aspect of hematopoietic lineage cell activation disorder-like symptoms should be considered as candidates for human hematopoietic lineage cell activation disorder therapeutic intervention. Dosages of test agents may be determined by deriving dose-response curves, as discussed below.

5.6 THE TREATMENT OF DISORDERS ASSOCIATED WITH STIMULATION OF G-PROTEIN ACTIVATED PI3K, INCLUDING INFLAMMATORY DISORDERS

The invention also encompasses methods and compositions for modifying hematopoietic lineage cell activation and treating hematopoietic lineage cell activation disorders, including inflammatory disorders. For example, by decreasing the level of p101 gene expression, and/or p101 regulatory subunit gene activity, and/or downregulating activity of the p101 regulatory subunit pathway (e.g., by interfering with the interaction of p101 regulatory subunit with the p120 catalytic subunit, or by targeting downstream signalling events), the response of leukocyte cells to factors which activate trimeric G protein associated receptors, such as cytokines, may be reduced and the symptoms of chronic inflammatory diseases ameliorated. Conversely, the response of leukocyte cells to activation of G protein associated receptors may be augmented by increasing p101 regulatory subunit activity. For example, such augmentation may serve to boost the response of the immune system to infections. Different approaches are discussed below.

5.6.1 INHIBITION OF p101 ADAPTOR EXPRESSION OR p101 ADAPTOR ACTIVITY TO REDUCE G PROTEIN ACTIVATED PI3K ACTIVITY AND REDUCE INFLAMMATION

Any method which neutralizes catalytic subunit or inhibits expression of the p101 or p120 gene (either transcription or translation) can be used to reduce the inflammatory response. Such approaches can be used to treat inflammatory response disorders such as arthritis, including rheumatoid arthritis, septic shock, adult respiratory distress syndrome (ARDS), pneumonia, asthma and other lung conditions, allergies, reperfusion injury, atherosclerosis and other cardiovascular diseases, Alzheimer's disease, and cancer, to name just a few inflammatory disorders.

In one embodiment, immuno therapy can be designed to reduce the level of endogenous p101 or p120 gene expression, e.g., using antisense or ribozyme approaches to inhibit or prevent translation of p101 or p120 mRNA transcripts; triple helix approaches to inhibit transcription of the p101 or p120 gene; or targeted homologous recombination to inactivate or "knock out" the p101 or p120 gene or its endogenous promoter.

Antisense approaches involve the design of oligonucleotides (either DNA or RNA) that are complementary to p101 or p120 regulatory subunit mRNA. The antisense oligonucleotides will bind to the complementary p101 or p120 mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently shown to be effective at inhibiting translation of mRNAs as well. See generally, Wagner, R., 1994, Nature 372:333–335. Thus, oligonucleotides complementary to either the 5'- or 3'- non-translated, non-coding regions of the p101 or p120 shown in FIG. 1 and FIG. 3 could be used in an antisense approach to inhibit translation of endogenous p101 or p120mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of p101 regulatory subunit mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. W088/09810, published Dec. 15, 1988), or hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al., 1988, Nucl. Acids Res. 16:3209. Methylphosphonate oligonucleotides can be prepared by use of controlled pore glass polymer supports (Sarin et al., 1988, Proc. Natl. Acad. Sci. U.S.A. 85:7448–7451).

While antisense nucleotides complementary to the p101 or p120 coding region sequence could be used, those complementary to the transcribed untranslated region are most preferred.

The antisense molecules should be delivered to cells which express the p101 regulatory subunit in vivo, e.g., cells of hempatopoetic origin such as platelet, and neutrophils and other leukocytes. A number of methods have been developed for delivering antisense DNA or RNA to cells; e.g., antisense molecules can be injected directly into the tissue or cell derivation site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous p101 or p120 transcripts and thereby prevent translation of the p101 or p120mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc. Any type of plasmid, cosmid, YAC or viral vector can be used to prepare the recombinant DNA construct which can be introduced directly into the tissue or cell derivation site; e.g., the bone marrow. Alternatively, viral vectors can be used which selectively infect the desired tissue or cell type; (e.g., viruses which infect cells of hematopoietic lineage), in which case administration may be accomplished by another route (e.g., systemically).

Ribozyme molecules designed to catalytically cleave p101 or p120 mRNA transcripts can also be used to prevent translation of p101 or p120mRNA and expression of p101 regulatory subunit. (See, e.g., PCT International Publication WO90/11364, published Oct. 4, 1990; Sarver et al., 1990, Science 247:1222–1225). While ribozymes that cleave mRNA at site specific recognition sequences can be used to destroy p101 or p120 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. There are hundreds of potential hammerhead ribozyme cleavage sites within the nucleotide sequence of human p101 or p120 cDNA (FIG. 3). Preferably the ribozyme is engineered so that the cleavage recognition site is located near the 5' end of the p101 or p120 mRNA; ie., to increase efficiency and minimize the intracellular accumulation of non-functional mRNA transcripts.

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug et al., 1984, Science, 224:574–578; Zaug and Cech, 1986, Science, 231:470–475; Zaug et al., 1986, Nature, 324:429–433; published International Patent Application No. WO 88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in p101 or p120.

As in the antisense approach, the ribozymes can be composed of modified oligonucleotides (e.g. for improved stability, targeting, etc.) and should be delivered to cells which express the p101 regulatory subunit in vivo, e.g., neutrophils. A preferred method of delivery involves using a DNA construct "encoding" the ribozyme under the control of a strong constitutive pol III or pol II promoter, so that transfected cells will produce sufficient quantities of the ribozyme to destroy endogenous p101 or p120 messages and inhibit translation. Because ribozymes unlike antisense molecules, are catalytic, a lower intracellular concentration is required for efficiency.

Endogenous p101 or p120 gene expression can also be reduced by inactivating or "knocking out" the p101 or p120 gene or its promoter using targeted homologous recombination. (E.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional p101 regulatory subunit (or a completely unrelated DNA sequence) flanked by DNA homologous to the endogenous p101 or p120 gene (either the coding regions or regulatory regions of the p101 or p120 gene ) can be used, with or without a selectable marker and/or a negative selectable marker, to transfect cells that express p101 regulatory subunit in vivo. Insertion of the DNA construct, via targeted homologous recombination, results in inactivation of the p101 or p120 gene. Such approaches are particularly suited in the agricultural field where modifications to ES (embryonic stem) cells can be used to generate animal offspring with an inactive p101 regulatory subunit (e.g., see Thomas & Capecchi 1987 and Thompson 1989, supra). However this approach can be adapted for use in humans provided the recombinant DNA constructs are directly administered or targeted to the required site in vivo using appropriate viral vectors.

Alternatively, endogenous p101 or pp120 gene expression can be reduced by targeting deoxyribonucleotide sequences complementary to the regulatory region of the p101 or p120 gene gene (i.e., the p101 or p120 promoter and/or enhancers) to form triple helical structures that prevent transcription of the p101 or p120 gene in target cells in the body. (See generally, Helene, C. 1991, Anticancer Drug Des., 6(6):569–84; Helene, C. et al., 1992, Ann, New York Acad. Sci., 660:27–36; and Maher, L. J., 1992, Bioassays 14(12):807–15).

In yet another embodiment of the invention, the activity of p101 regulatory subunit can be reduced using a "dominant negative" approach to interfere with trimeric G protein activation of PI3K. To this end, constructs which encode defective p101 regulatory subunits can be used in gene therapy approaches to diminish the activity of the p101 regulatory subunit in appropriate target cells. For example, nucleotide sequences that direct host cell expression of p101 regulatory subunits in which the Gβγ interacting domain is deleted or mutated can be introduced into hematopoietic cells (either by in vivo or ex vivo gene therapy methods described above). Alternatively, nucleotide sequences which encode only a functional domain of p101 could be used as an inhibitor of native p101/p120 interactions. Alternatively, targeted homologous-recombination can be utilized to introduce such deletions or mutations into the subject's endogenous p101 or p120 gene in the bone marrow. The engineered cells will express non-functional receptors (i.e., a regulatory subunit that is capable of binding the catalytic subunit, but incapable of stimulating the catalytic activity in response to G protein activation). Such engineered cells, i.e. neutrophils or other leukocyte lineages, should demonstrate a diminished response to activation of G protein linked receptors to extracellular chemokines, resulting in reduction of the inflammatory phenotype.

5.6.2 RESTORATION OR INCREASE IN p101 REGULATORY SUBUNIT EXPRESSION OR ACTIVITY TO PROMOTE IMMUNE SYSTEM ACTIVATION

With respect to an increase in the level of normal p101 or p120 gene expression and/or p101 regulatory subunit gene product activity, p101 or p120 nucleic acid sequences can be utilized for the treatment of hematopoietic lineage cell activation disorders, including reduced immune system responses to chemokines. Where the cause of the immune system disfunction is a defective p101 regulatory subunit, treatment can be administered, for example, in the form of gene replacement therapy. Specifically, one or more copies of a normal p101 gene or a portion of the p101 gene that directs the production of a p101 gene product exhibiting normal function, may be inserted into the appropriate cells within a patient or animal subject, using vectors which include, but are not limited to adenovirus, adeno-associated virus, retrovirus and herpes virus vectors, in addition to other particles that introduce DNA into cells, such as liposomes.

Because the p101 or p120 gene is expressed in the hematopoietic lineage cells, including the neutrophils and other leukocytes, such gene replacement therapy techniques should be capable of delivering p101 or p120 gene sequences to these cell types within patients. Alternatively, targeted homologous recombination can be utilized to correct the defective endogenous p101 or p120 gene in the appropriate cell type; e.g., bone marrow cells or neutrophils and/or other leukocytes. In animals, targeted homologous recombination can be used to correct the defect in ES cells in order to generate offspring with a corrected trait.

Finally, compounds identified in the assays described above that stimulate, enhance, or modify the signal transduced by activated p101 regulatory subunit, e.g., by activating downstream signalling proteins in the p101 regulatory subunit cascade and thereby by-passing the defective p101 regulatory subunit, can be used to achieve immune system stimulation. The formulation and mode of administration will depend upon the physico-chemical properties of the compound.

5.7 PHARMACEUTICAL PREPARATIONS AND METHODS OF ADMINISTRATION

The compounds that are determined to affect p101 or p120 gene expression or p101 regulatory subunit activity, or the interaction of p101 with any of its binding partners including but not limited to the catalytic subunit, can be administered to a patient at therapeutically effective doses to treat or ameliorate hematopoietic cell activation disorders, including inflammatory response disorders such as arthritis, including rheumatoid arthritis, septic shock, adult respiratory distress syndrome (ARDS), pneumonia, asthma and other lung conditions, allergies, reperfusion injury, atherosclerosis and other cardiovascular diseases, Alzheimer's disease, and cancer. A therapeutically effective dose refers to that amount of the compound sufficient to result in amelioration of symptoms of hematopoietic lineage cell activation disorders.

5.7.1 EFFECTIVE DOSE

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

5.7.2 FORMULATIONS AND USE

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The following examples are presented to illustrate the present invention and to assist one of ordinary skill in making and using the same. The examples are not intended in any way to otherwise limit the scope of the disclosure or the protection granted by Letters patent hereon.

6 EXAMPLE: Purification and characterization of Gβγ-activated PI3K activities

6.1 MATERIALS & METHODS

6.1.1 PI3K ASSAYS

Purified aliquots of Sf9-derived or pig neutrophil cytosol-derived PI3K were diluted in ice-cold 0.12M NaCl, 25 mM HEPES, 1 mM EGTA, 1 mM DTT, 1 mg-ml$^{-1}$ BSA, 1% betaine, 0.02%, w/v, Tween-20, pH 7.4, 0° C. to an appropriate extent, then 5 μl aliquots were stored on ice until assayed. If the PI3K assays were performed on immunoprecipitates from U937 cells (see following examples) then the PI3K was immobilized on 10 μl of packed protein G Sepharose beads in an ice-cold buffer defined above. 30 μl of a mixture of phospholipids with or without Gβγs and/or Gαs (either GDP-bound or activated) was added to the 5 μl fractions, or 10 μl of beads, and mixed. After 10 minutes on ice, 5–10 μl of last wash buffer, supplemented with MgCl$_2$ to give a final concentration in the extant assay volume of 3.5 mM, was added and mixed. Six minutes later, 5 μl of last wash buffer was added (to give a final assay volume of 50 μl) containing [γ$^{32}$P]-ATP (typically 10 μCi assay$^{-1}$, Amersham, PB10168) and 3.5MM MgCl$_2$, tubes were mixed and transferred to a 30° C. water bath. Assays were quenched after 15 minute with 500 μl of chloroform:methanol:H$_2$O (29:54:13.1, v/v/v). One μl of 100 mM ATP, 103 μl of 2.4 HCl and 434 μl of chloroform were subsequently added to generate a two phase 'Folch' solvent distribution. After mixing and centrifugation, the lower phases were removed and transferred to clean tubes containing 424 μl of fresh 'upper phase' (methanol:1M HCl: chloroform; 48:47:3, v/v/v). After mixing and centrifugation the lower phase was removed to a fresh tube (during the purification or porcine neutrophil PI3Ks, [$^{32}$P]-lipid product was quantitated at this point with a geiger counter), dried under vacuum, deacylated and resolved by TLC on PEI plates (with 0.6M HCL; PtdIns(3,4,5)P$_3$ has an Rf of 0.47) (Stephens et al., 1994, Cell 77:83–93). In some experiments the dried lipid was redissolved in chloroform: methanol/2:1, v/v), applied to a potassium oxalate-impregnated TLC plated and resolved in a mixture of chloroform: acetone: methanol: acetic acid: H$_2$O (40:15:13:12:8, v/v/v/v/v; Traynor-Kaplan et al., 1988).

The lipid/G protein subunit mixtures were prepared as follows: PtdIns(4,5)P$_2$ (which was prepared from Folch phosphoinositide fractions by 2 cycles of chromatography on immobilized neomycin) and PtdEtn (Sigma) were dried under vacuum (sufficient to give final concentrations in the assay of 50 μM and 0.5 mM, respectively). In some experiments PtdIns4P (prepared similarly to the PtdIns(4,5)P$_2$) and/or PtdIns (Sigma) were included. The dried lipid was bath-sonicated (at room temperature) into final wash buffer (above) supplemented with 0.1%, sodium cholate. After cooling on ice, portions of this dispersed lipid stock were mixed with a mixture, totaling 1 μl assay$^{-1}$, of Gβγ storage buffer (1k cholate; 50 mM HEPES, pH 7.5, 4° C., 0.1M NaCl; 1 mM DTT; 0.5 mM EDTA), active Gβγ, or an equivalent volume of boiled Gβγ from 3–7 mg-ml$^{-1}$ stocks in storage buffer. In some experiments the 1M1 would include Gα subunits or their storage buffer in which case the Gαβs were premixed with the Gα subunits (either GDP bound or activated; see below) for 10 minutes on ice.

Gα subunits (an equimolar mixture of Gα:o, i, i$_2$ and i, prepared as described in, and stored in the same buffer as the Gβγ subunits except supplemented with 10 μM GDP) were activated by incubation on ice with 10 mM NaF, 30 μM AlCl, (A/F) for 10 mins; assays into which these subunits were diluted also contained A/F. a) Protein Purification Pigs blood (42 batches) was collected directly into anti-coagulant in 21 containers. Within 40 minute of collection the blood/ anti-coagulant was mixed with 3% (w/v) polyvinylpyrrolidone (PVP, 360 kD) in isotonic saline (4.2 of blood mixture: 0.8 of PVP). After 35 minutes standing (in 25 containers) the erythrocytes had settled adequately to allow the supernatant to be siphoned off and centrifuged (8 minutes, 1000× g) in 1 liter containers. Approximately 28 liters of this primary supernatant was recovered. The sedimented cells were resuspended in Hank's saline such that the final accumulated volume was contained in two 1 liter centrifuge bottles. The cells were sedimented by centrifugation (8 minute 1000× g). Supernatants were aspirated and the cell pellet was hypotonically shocked (to lyse any residual, contaminating erythrocytes) by the addition of 70 mls of ice-cold H$_2$O. After 25–30 seconds of mixing, 77 mls of 10× Hank's saline (without calcium) was added. After one wash with Hank's saline, the cells were combined into one centrifuge bottle, pelleted and resuspended in 500 mls of ice-cold; 40 mM TRIS, pH 7.5, 4° C.; 0.12M NaCl; 2.5 mM MgCl$_2$. Di-isopropylfluorophosphate was added (final concentration 0.5 mM), after 5 minute on ice the cells were pelleted (approximately 80–90 mls packed volume) and resuspended in 300 mls of ice-cold 40 mM TRIS, pH 7.5; 0.1M NaCl; 2.5MM MgCl$_2$; 1 mM EGTA; 0.2 mM EDTA and antiproteases I. The cell suspension was sonicated (Heat Systems Probe sonicator, setting 9.25, 4×15 seconds with 1 minute mixing, on ice, between each burst) then centrifuged (2000× g 10 min) to sediment unbroken cells and nuclei (less than 5% of cells remained intact). The supernatant was centrifuged (at 100,000× g 60 min, 4° C.) and the supernatants were decanted, pooled, mixed with EDTA, betaine and DTT (final concentrations of 5 mM, 1% and 1 mM; respectively) and finally frozen in liquid nitrogen and stored at −80° C. Cytosolic fractions prepared in this manner typically had a protein concentration of 8 to 9 mg-ml$^{-1}$ (about 2.5 g protein per preparation). Once the cytosol from the equivalent of 750 liters of blood (18 to 42 preparations, 9×10$^{12}$ cells, 40 g protein) had been collected and stored at −80° C., they were thawed in three batches separated by 5 hr. From this point onwards all procedures were carried out at 2°–4° C.

The freshly thawed cytosol was supplemented with Tween-20 (0.05%, w/v, final concentration), centrifuged (20 000× g for 30 min, 2° C.) filtered (5 μm cellulose nitrate, 4.5 cms diameter; Whatman) diluted approximately 2.5× with buffer K (see below) to a final conductivity of 200 μS (at 4° C.), then loaded (12.5 ml-min$^{-1}$ with a peristaltic pump) onto a 800 ml (5 cms diameter) column of fast flow Q Sepharose equilibrated with buffer K. The total volume of diluted cytosol was approximately 15.5 liters. Once loaded, the column was washed with 1 liter of buffer K then eluted with a 4.5 liter, linear gradient, of 0.1 to 0.6M NaCl in buffer K at 8 ml-min$^{-1}$. Fifty 1 ml fractions were collected. The conductivity and Absorbance (at 280 nm) of the column eluate were monitored continuously (and in all subsequent steps). Buffer K had the following composition: 40 mM TRIS/Hl, 1 mM EGTA, 0.2 mM EDTA, 1% betaine; 0.05% w/v Tween 20, 5 mM β-glycerophosphate pH 7.5 at 4° C., 15 mM P-mercaptoethanol with 4 μgml$^{-1}$ each of antipain, leupeptin, bestatin, pepstatin A and aprotinin and 0.1 mM PMSF ('antiproteases II'). This solution, as well as those that follow, was 0.2 μm filtered.

Once the relevant fractions had been identified by PI3K assays, they were pooled and immediately loaded (10 ml-min$^{-1}$) onto a 1.8 column (5 cms diameter) of Sephadex-G25-fine, which had been pre-equilibrated with 18 buffer L (only last 2 liters with antiproteases II), (buffer L contained: 5 mM β-glycerophosphate, 20 mM KCl, 0.05% w/v Tween 20, 1% betaine, 0.1 mM EDTA, 10 mM potassium phosphate pH 7.0 at 4° C., 15 mM β-mercaptoethanol plus antiproteases II). The desalted pool from Q sepharose was immediately loaded (5 ml-min$^{-1}$) onto 80 ml of hydroxylapatite (2.6 cms diameter; Macroprep-ceramic, BioRad) equilibrated with 1 liter of buffer M (5 mM β-glycerophosphate; 10 mM potassium phosphate, pH 7.0, 4° C., 0.05% w/v Tween 20, 1% Betaine, 15 mM β-mercaptoethanol) at a flow rate of 10 ml-min$^{-1}$, and then with 100 mls of buffer N, (comprised of buffer M supplemented with 0.1 mM EDTA and antiproteases I) immediately prior to loading the sample. After loading, the column was washed with 100 mls of buffer N and eluted with an 100 ml linear gradient of 0.05 to 0.35M potassium phosphate in buffer N (4 ml-min$^{-1}$). 25 ml fractions were collected and assayed for Gβγ-stimulated PI3K activity.

Relevant fractions were pooled (typically a total of 100 mls), diluted 3× with buffer O (to a conductivity of 250 μS, 4° C.) and loaded (1.1 ml-min$^{-1}$) onto Heparin Sepharose HR (1.6 cms diameter column that had been pre-equilibrated with 150 mls of buffer O (see below, at 2 ml-min$^{-1}$). After loading, the column was washed with buffer O (30 mls) and eluted with a 140 ml linear gradient of 0.1–0.7M KCl in buffer O (flow rate 1 ml-min$^{-1}$), the elute was collected in 5 ml fractions. Buffer O was: 20 mM HEPES, 1 mM EGTA, 0.2 EDTA, 0.05w/v/Tween 20, 1.0 butane, 1 mM β-glycerophosphate pH 7.2, 4° C., 15MM β-mercaptoethanol, plus antiproteases II.

Gβγ-stimulated PI3K activity eluted from Heparin sepharose HR in two peaks, designated peaks A and B. Both A and B were further purified by sequential use of the same combination of columns. Peak A was in 15 mls (0.4M KCl) and was diluted 8 fold into buffer P (see below) to a final conductivity of 200 μS, 4° C.), peak B was in 15 mls (0.6M KCl) and was diluted 10× into buffer P (to a final conductivity of 200 μS, 4° C.). Dilution was immediately prior to loading at 1 ml-min$^{-1}$ onto a Mono Q 5/5 HR column pre-equilibrated with 20 mls of buffer P. After loading, the column was washed with 5 mls of buffer P. Eluate was collected in 0.5 ml fractions. Buffer P contained: 10 mM Tris, 1 mM EGTA, 0.2 EDTA, 0.05% w/v Tween 20, 1% betaine, 1 mM β-glycerophosphate, pH 7.1, 4° C., 15 mM β-mercaptoethanol plus antiproteases II.

The relevant fractions from Mono Q (A) and (B) were pooled independently (both had a total volume of 3 mls) concentrated with an ultrafiltration unit (50 kD cut-off pre-washed with buffer P) to 0.8 mls, centrifuged (10, 000× g for 10 minutes, 0° C.) and loaded (0.25 ml-min$^{-1}$) directly onto a high performance size exclusion chromatography column (V$_o$ 72 mls, V$_t$ 172 mls) pre-equilibrated with buffer Q (see below; 2 liters without antiproteases II, then 150 mls with antiproteases II) 1.5 ml fractions were collected just prior to the V$_o$. Buffer Q contained: 0.17M KCl, 1% betaine, 0.05% w/v Tween 20, 1 mM β-glycerophosphate, 1 mM EGTA, 0.2 mM EDTA, 1.5 m-M potassium phosphate, 40 mM HEPES, pH 6.9 at 4° C., 15 mM β-mercaptoethanol.

Relevant fractions from A and B were pooled independently (both had a total volume of 6 mls) diluted with buffer R to 24 mls (final conductivity 250 μS, 4° C.) and loaded (0.8 ml-min$^{-1}$) onto an acrylic-based cation-exchange HPLC column (2.5 mls volume, BioRad) and eluted with a 25 ml linear gradient of KCl (0.1 to 0.6M) in buffer R. The eluate was collected in 1 ml fractions. Buffer R contained: 1% betaine, 0.05% w/v Tween 20, 1 mM EGTA, 0.2 mM EDTA, 20 mM HEPES, pH 6.8 at 4° C., 15 mM β-mercaptoethanol plus antiproteases II.

Relevant fractions were pooled (3 mls for (A), 2 mls for (B)), diluted 7× with buffer S (final conductivity of 180 μS, 4° C.) and loaded (0.15 ml-min$^{-1}$); onto a Mini Q column (0.24 mls, operated on a Pharmacia Smart™ system). The column was washed with 1 ml of buffer S and eluted with a linear gradient of NaCl (0.1 to 0.5M NaCl) in buffer S at 0.1 ml-min$^{-1}$. The elute was collected 75 μl fractions. Buffer S contained: 1% betaine, 0.05w w/v Tween 20, 1 mM EGTA, 0.2 mM EDTA, 2 mM β-glycerophosphate, 10 mM TRIS, pH 7.7, 4° C., 1 mM DTT (without antiproteases).

Protein concentrations throughout the purification were was estimated in four ways: (a) with a protein binding dye (BioRad; this was only used on lysates, cytosolic and Q sepharose fractions); (b) by integration of Abs 280 nm peak areas (this was calibrated by using the dye binding assay); (c) proteins on filters were stained with Ponceau S and compared with the staining intensity of defined aliquots of a similarly immobilized standard; and (d) proteins resolved by SDS-PAGE and stained with Coomassie R250 were compared with aliquots of proteins of known concentration run on the same, gel.

Final preparation of PI3K (or first stage purified material) were incubated with 100 nM [$^3$H]-17-hydroxy-wortmannin (17.7 Ci mmol$^{-1}$, Amersham, custom made), resolved by SDS-PAGE, stained with Coomassie Blue, and photographed. [$^3$H] was then detected fluorographically.

6.2 RESULTS

Analysis of porcine neutrophil cytosol by an ion-exchange chromatography showed it contained a Gβγ-activated PI3K activity of similar properties to ones already described in U937 and osteosarcoma cells. Use of [$^3$H]-17-hydroxy-wortmannin as a probe identified a doublet of proteins of apparent size 117 kD and 120 kD which eluted in the fractions containing Gβγ-activated PI3K activity, and further, that they were at 2–4% of the levels of [$^3$H]-17-hydroxy-wortmannin bound by p101α and/or p110β (see FIGS. 5). This peak of Gβγ activated PI3K activity was purified further (all figures and tables detail the purification of the preparations of PI3Ks that were ultimately sequenced). During this procedure, it split into two peaks (A and B) both which displayed apparent, native, relative, molecular masses of 220 kD. Once essentially pure, as assessed by Coomassie-stained SDS-PAGE gels, it was clear that both activities co-migrated with two proteins: (A) with proteins of 117 kD (which specifically bound [$^3$H]-17-hydroxy-wortmannin and was assumed therefore to be the catalytic subunit) and 101 kD; and (B) with proteins of 120 kD (which also bound [$^3$H]-17-hydroxy-wortmannin) and 101 kD. This result indicated that the PI3K activities were p117/p101 and p120/p101 heterodimers in their native state. In their final forms PI3Ks A and B had been purified approximately 180,000× and 380,000× from neutrophil lysates (1,000,000,000× from blood) with 5.5% overall recovery of activity. Table 1 defines the recoveries of protein and PI3K activity through each step).

TABLE 1

Purification of pig leukocyte G-protein βγ subunit activated PI3K's

| Pool of activity | | Total protein in pools | Pool Volume | Total Activity in pools | Fold Purification |
|---|---|---|---|---|---|
| Cytosol | | 40 g | 151 | 100% | 1 |
| Q-Sepharose | | 1.5 g | 40 mls | 90% | 24 |
| (desalted) | | (1.5 g) | (450 mls) | (124%) | |
| Hydroxylapatite | | 162 mg | 100 mls | 125% | 309 |
| Heparin Sepharose | Peak A | 19 mg | 15 mls | 46% | 970 |
| | Peak B | 12 mg | 15 mls | 53% | 1769 |
| Mono Q pool | A | 5.4 mg | 3 mls | 16% | 1187 |
| | B | 1.4 mg | 3 mls | 15% | 4291 |
| Size exclusion | A | 0.722 mg | 6 mls | 16% | 8902 |
| (850 μl applied) | | | | | |
| | B | 0.2 mg | 6 mls | 15.5% | 51038 |
| Cation Exchange | A | 0.13 mg | 3 mls | 6% | 18489 |
| | B | 0.014 mg | 2 mls | 9.5% | 271761 |
| Mini Q pool | from A | 15 μg | 0.225 mls | 2.2% | 58754 |
| | from B | 10 μg | 0.225 mls | 3.1% | 174151 |

These extents of enrichment are consistent with the quantities of [$^3$H]-17-hydroxy-wortmannin bound by these proteins compared to p85/p110 family members. All of these proteins are thus considered to be of low abundance.

Purified preparations of PI3Ks A and B were indistinguishable on the basis of their lipid kinase activities. Both preparations were (a) activated over 100× by Gβγ subunits, in a Gβ-GDP-sensitive fashion, (b) completely inhibited by 100 nM wortmannin (with 5 μM ATP in the assays), (c) insensitive, either in the presence or absence of Gβγs, to tyrosine phosphorylated peptides which activate p85/p110 family PI3Ks five fold (see FIG. 6), and (d) able to 3-phosphorylate PtdIns, PtdIns4P and PtdIns(4,5)P$_2$ (the identity of the products was established by sequential deacylation and deglyceration followed by anion-exchange HPLC analysis of the [$^{32}$P]-labelled water-soluble products with internal [$^3$H]-labeled standards). Further, the purified preparations of PI3K A and B displayed the lowest apparent Km for the latter substrate (8 and 10 μM for A and B, respectively) utilizing the γ-phosphate of ATP as the phosphate donor (results not shown)

7. EXAMPLE: PEPTIDE SEQUENCING OF GBγ-ACTIVATED PI3K A AND B

In this example, both PI3K proteins were analyzed by amino acid sequencing. PI3Ks A and B, purified from the equivalent of 40 g of cytosolic protein, were Western blotted onto nitrocellulose, stained with Ponceau S, the bands corresponding to all four subunits were excised, treated with trypsin and processed for internal amino acid sequence analysis.

7.1 MATERIALS AND METHODS

Generation of peptides and peptide sequencing. Aliquots of protein for sequencing were Western blotted (in a wet blotter) onto nitrocellulose (0.45 μm pore size BA85; Schleicher and Schuell). The transfer buffer contained 192 mM glycine, 25 mM TRIS and 10% v/v methanol. Prior to assembling the final transfer unit the Whatman No. 1 filter paper supports on the (−) side of gel/filter sandwich, and the gel (1 mm thick), were soaked (2–3 mins) in transfer buffer containing 0.0005% (w/v) SDS. The transfer was for 16 h at a fixed 35 V (0.25 to 0.35 Amps, at 5° C.). The filters were stained with 0.1% Ponceau S in 1% acetic acid for 1 min, then destained for 1 minute in 1% acetic acid. Approximately 85–90% of the protein loaded on the gel was recovered the filter. The bands of interest were excised from the nitrocellulose and processed for internal amino acid sequence analysis as described (Tempst et al., 1990, Electrophoresis 11:537–552), with modifications (Lui et al., 1996). Briefly, in situ proteolytic cleavage was done using 0.5 μg trypsin (Promega, Madison, Wis.) in 25 μl 100 mM NH$_4$HCO$_3$ (supplemented with 1% Zwittergent 3–16) at 37° C. for 2 hours. The resulting peptide mixture was reduced and S-alkylated with, respectively 0.1% β-mercaptoethanol (BioRad, Richmond, Calif.) and 0.3% 4-vinyl pyridine (Aldrich, Milwaukee, Wis.), and fractionated by reversed phase HPLC. An enzyme blank was done on an equally sized strip of nitrocellulose.

HPLC solvents and system configuration were as described (Elicone et al., 1994), except that an 2.1 mm 214 Tp54 Vydac C4 (Separations Group, Hesperia, Calif.) column was used with gradient elution at a flow rate of 100 μl/min. Identification of Trp-containing peptides was done by manual ratio analysis of absorbances at 297 and 277 nm, monitored in real time using an Applied Biosystems (Foster City, Calif.) model 1000S diodarray detector (Erdjument-Bromage et al., 1994). Fractions were collected by hand, kept on ice for the duration of the run and then stored at −70° C. before analysis.

Purified peptides were analyzed by combination of automated Edman degradation and matric-assisted laser-desorption ionization time-of-flight (MALDI-TOF) mass spectrometry; details about this combined approach, including mass-aided post-chemical sequencing routines can be found elsewhere (Geromanos et al., 1994, Techniques in Protein Chemistry V 143–150; Elicone et al., 1994, J. Chromatogr. 676:121–137; Erdjument-Bromage et al., 1994, Protein Sci. 3:2435–2446). After storage, column fractions were supplemented with neat TPA (to give a final concentration of 10%) before loading onto the sequencer disks and mass spectrometer target. Mass analysis (on 2% aliquots) was carried out using a model Voyager RP MALDI-TOF instrument (Vestec/PerSeptive, Framingham, Mass.) in the linear mode, with a 337 nm output nitrogen laser, an 1.3 m flight tube and α-cyano-4-hydroxy cinnamic acid (premade solution obtained from Linear Sci., Reno, Nev.) as the matrix. A 30 kV ion acceleration voltage (grid voltage at 70%, guide wire voltage at 0.1%) and −2.0 kV multiplier voltage were used. Laser fluence and number of acquisitions were adjusted as judged from optimal deflections of specific maxima, using a TDS 520 Tektronix (Beaverton, Oreg.) digitizing oscilloscope. Mz (mass to charge) spectra were generated from the time-of-flight files using GRAMS (Galactic Ind., Salem, N.H.) data analysis software. Every sample was analyzed twice, in the presence and absence of two calibrants (25 femtomoles each of APID and P8930), as described (Geromanos et al., 1994). Chemical sequencing (on 95% of the sample) was done using a model 477A instrument from Applied Biosystems (AB). Stepwise liberated PTH-amino acids were identified using an 'on-line' 120A HPLC system (AB) equipped with a PTH C18 (2/1× 220 mm; 5 micron particle size) column (AB). Instruments and procedures were optimized for femtomole level phenyl thihydantoin amino acid analysis as described (Erdjument-Bromage et al., 1994, Protein Sci. 3:2435–2446; Tempst et al., 1994, Methods CompanionMeth. Enzymol. 6:284–261).

Peptide average isotopic masses were summed from the identified residues (including the presumed ones) using ProComp version 1.2 software (obtained from Dr. P. C. Andrews, University of Michigan, Ann Arbor, Mich.).

A doubly tyrosine phosphorylated peptide (18 residues) based on the sequence surrounding tyrosines 740 and 751 in the PDGF βR was prepared by the microchemical facility at the Babraham Institute.

7.2 RESULTS

Peptide sequence data immediately resolved several issues regarding the relationships between these proteins. The p101s derived from both PI3Ks A and B were identical and further a relatively common allelic-variant was identified at 483 in the ORF, (marked in FIG. 4) such that a serine was replaced by a glycine. p117 and p120 displayed virtually identical tryptic HPLC profiles and all apparently common peptides that were sequenced from both species were identical with the exception of a amino-terminal blocked peptide from p117 (see below). Peptide sequence information was then used to design probes for retrieving the nucleotide sequence encoding these proteins.

8. EXAMPLE: Cloning of the cDNAs encoding p120 and p101

Degenerate oligonucleotide probes, based on the sequence of a peptide from p120 and a peptide from p101 were used to screen an oligo-dT-primed, amplified, cDNA library (made from pig neutrophil poly A-selected RNA). Described blow is the cloning and characterization of cDNA's encoding both the p101 and p120 proteins.

8.1 MATERIALS AND METHODS

We prepared 0.7 mg total RNA from $4.2 \times 10^9$ pig neutrophils (Chomczynski & Sacchi, 1987, Anal. Biochemistry 162:156–159). This RNA was used by Stratagene (San Diego, Calif.) to produce PolyA-selected mRNA from which they prepared oligodT- and random-primed cDNA libraries in λZAPII (approximately $5.4 \times 10^{-6}$ and $3.2 \times 10^6$ primary p.f.u. respectively). Amplified libraries were constructed from approximately $2 \times 10^6$ original recombinants and these were used to screen for p120 and p101 cDNAs by standard procedures. $2.5 \times 10^6$ plaques derived from the oligodT-primed library were screened using a [$^{32}$P]-labelled oligo based on peptide sequence from p120 [CA(T/C) GA(T/C) TT(T/C) ACI CA(A/G) CA(A/G) GTI CA(A/G) GTI AT(T/C/A) GA(T/C) ATG (SEQ ID NO:5)]. Twelve positive clones were identified isolated as Bluescript™ based plasmids and both DBA strands sequenced (using the ABI automatic sequencing facility at the Babraham Institute). The inserts of these plasmids represented a series of overlapping clones with two clones defining a full length ORF encoding all of the peptide sequence derived from p117/p120 tryptic digests (FIG. 4).

$0.9 \times 10^6$ plaques derived from the oligodT-primed library were screened using a [$^{32}$P]-labelled oligo based on peptide sequence from p101 [GCITA(T/C)ATGGA(A/G)GA(T/C) ATIGA(A/G)GA](SEQ ID NO:6). 1 positive clone was identified, isolated and sequenced. The 5' end of this clone (D11) represented part of the sequence for one of the tryptic peptides, thus identifying it as a partial clone. A further $0.6 \times 10^6$ plaques from the oligoT-primed library were screened using a [$^{32}$P]-labelled Cla-1 restriction fragment derived from D11. Sixty-six positive clones were identified, 49 of which were isolated and some partially sequenced. These represented a series of overlapping clones all of which contained D11 sequence but all of which were smaller than D11 itself. $3.5 \times 10^6$ plaques from the random-primed library were then screened using a [$^{32}$P]-labelled Apa-1 restriction fragment derived from D11. Ninety-eight positive clones were identified. These clones were re-screened (at the stage of primary plaque isolates) by a PCR-based approach using primers designed against the Bluescript™ vector (either 'forward' and 'reverse' primers) and internal D11 sequence. This enabled us to identify (independent of orientation) the longest potential N-terminal extensions encoding p101 sequence. The 3 clones giving the largest PCR-fragment were isolated and sequenced. These represented overlapping clones which, together with D11, defined a full length ORF encoding all of the peptide sequence derived from the p101 tryptic digest (FIG. 1 and FIG. 2)

8.2 RESULTS

Two clones defined a full length ORF encoding all of the p117/p120 tryptic peptides (see FIGS. 1–4). Of three potential start methionines, the central one was identified as active (in contrast to the assumption of Stoyanov et al., 1995, Science 269:690–693) on the basis of the precise match between the measured mass of an amino-terminal blocked p120-derived peptide and the theoretical masses of amino-terminal peptides that would be derived as a result of initiating translation at each of the three methionines. As such, p120 has a theoretical size of 126 kD. Comparison of the mass of the amino-terminal blocked peptide produced from p117 with the relevant regions of the amino-terminal end of p120 indicates no precise matches (allowing for usual amino-terminal blocking). Hence p117 is unlikely to be a proteolytically or post-translationally modified form of p120, nor is it likely to result from use of a second translation start point within the p120 message. However, a cDNA with an ORF encoding p117 has not been isolated.

The protein and DNA sequences defining p120 were used to search data bases for similar structures. Similarities with all previously cloned PI3Ks were identified. However, the sequence was nearly identical, allowing for species differences, to p110γ (Stoyanov et al., 1995). The only significant discrepancy between our sequence and that Stoyanov et al., is found in the extreme COOH terminus. On the basis of primary structure only, the identification of a COOH terminal pleckstrin homology domain in p120 could not be confirmed.

By utilizing several overlapping fragments, derived from both oligo-dT and random-primed, pig neutrophil-derived, cDNA libraries, a full length ORF encoding all of the peptide sequence derived from p101 has been defined. A p101-derived, amino-terminal blocked peptide was identified; its mass was precisely equivalent to that predicted for an amino-terminal acetylated version of the first 12 residues defined by the predicted start in the ORF described. The predicted relative molecular mass of p101 is 97 kD. Although the protein and DNA sequence data bases were searched for similar structures or sub-structures, no significant matches were identified.

9. EXAMPLE: Expression of p120 and p101 in insect cells

Recombinant, clonal, baculo-viruses (rbv) harboring either a amino-terminal, 6× HIS-tagged p120 (pAcHLT p120) cDNA or a amino-terminal, (EE)-tagged p101 cDNA (pAcO-Gl) p101) were prepared and used to drive production of the above proteins in insect (Sf9) cells.

9.1 MATERIALS AND METHODS
9.2 CONSTRUCTION OF EXPRESSION VECTORS

The use of N-terminal PCR and appropriate restriction sites allowed the p120 and p101 ORFs to be manipulated into a form where they could be inserted in frame into various expression vectors. In each case, the first amino acid encoded after the N-terminal tag was the start methionine. The 3'-untranslated region of the p120 cDNA was used in full and that of the p101 cDNA truncated at a BamHI site (nucleotide 192, FIG. 1). The vectors used for baculovirus-driven expression in Sf9 cells were pAcHLT (which encodes an N-terminal '6× His-tag' followed by a thrombin cleavage site, Pharminogen; the p120 ORF was inserted into the XhoI-EcoRI sites) and pAcO-Gl (which encodes an N-terminal 'EE-tag', ONYX Pharmaceuticals; the p101 ORF was inserted into the EcoRI-NotI sites). All vectors were N-terminally sequenced before use.

9.2.1 Sf9 cell transfections and production of recombinant proteins

Sf9 cells were grown in TNM FH with 11% HI-FBS in a spinner flask and were maintained at between 0.5 and $2\times10^6$ cells $ml^{-1}$. Sf9 cells were transfected with Insectin™ (Invitrogen) liposomes with linearized baculo-gold DNA (Pharminogen) and relevant baculo-virus transfer vectors as recommended (Invitrogen). The resulting recombinant baculo viruses were plaque-purified and amplified to yield high-titre viral stocks. The optimal (for production of protein) dilutions were determined for each high-titre stock. pAcO-Gl p101 virus were allowed to infect adherent Sf9 cells for 2.2 days at 27° C.; pAcHLT p120 virus were allowed to infect in a spinner culture (usually) for 1.9 days at 27° C. Cells were harvested into ice-cold 0.41% KCl; 2.66% sucrose; 20 mM $MgCl_2$; 8 mM $NaH_2PO_4$, pH 6.2, 25° C.; treated with 1 mM di-isopropylfluorophosphate (5 minutes on ice), and washed once in the harvesting solution. Centrifugally packed aliquots of cells were frozen in liquid $N_2$ and stored at −80° C.

9.2.2 Purification of Sf9-derived proteins p120 was purified using a metal-ion chelation column (Talon, Clontech). Cell pellets were thawed into 0.10M NaCl; 50 mM sodium phosphate, pH 8.0, 4° C.; 10 mM Tris.HCl, pH 8.0, 4° C.; 1 mM $MgCl_2$ and antiproteases I (see above) at a ratio of 1 liter of infected Sf9 cell culture into 50 mls of sonication buffer, probe-sonicated (4×15 second bursts on ice), and centrifuged (120,000× g for 40 minutes, 4° C.). The supernatant was removed and pooled (cloudy supernatant at the top of the tube was removed separately, 0.45 $\mu$M filtered with a low-protein binding filter and then pooled with the remainder). The cytosolic fraction was supplemented with Tween-20 and betaine (0.05%, w/v, and 1%, respectively) then pumped onto a column of Talon resin equilibrated in equivalent buffer (1.2 mls of resin per liter of original infected Sf9 culture at a linear flow velocity of 20 cms $hr^{-1}$). This, and all subsequent steps were carried out at 4° C. The column was sequentially washed (same flow) with 20 column volumes each of: Buffer A, 50 mM sodium phosphate, pH 8.0, 4° C.; 10 mM Tris/HCl, pH 8.0, 4° C.; 0.15M NaCl; 1% betaine; 0.05%, w/v, Tween-20; buffer B, 1%, w/v, Triton X-100; 0.15M NaCl; 50 mM sodium phosphate, pH 8.0, 4° C.; 10 mM Tris, pH 8.0, 4° C.; 1% betaine 0.05%, w/v, Tween-20; buffer C, 0.15M NaCl; 50 mM sodium phosphate, pH 7.1, 4° C.; 1% betaine; 0.05%, w/v, Tween-20; buffer D; 0.15M NaCl; 30 mM Tris, pH 7.5, 4° C. %, 1% betaine, 0.02%, w/v, Tween-20; 10%, v/v, ethylene glycol; 1 mM $MgCl_2$; and then 8 column volumes buffer E, comprised of buffer D supplemented with 10 mM imidazole (pH 7.5). During the Buffer E wash, 2 ml fractions were collected. Finally, at half the flow used previously, the column was washed with buffer F, which was comprised of buffer D supplemented with 70 mM imidazole (pH 7.5; final concentration). Typically 1 ml fractions were collected. With experience fractions were pooled on the basis of the Abs 280 nm trace (continuously recorded) and supplemented with 1 mM DTT and 1 mM EGTA (final concentrations) immediately. Typically this process yielded 4 mg of p120 per liter of Sf9 culture. The p120 prepared in this manner was usually greater than 90% pure. The final pool of p120 was desalted via a 15 ml column of G-25 superfine equilibrated in buffer G, which was comprised of buffer D supplemented with 1 mM DTT and 1 mM EGTA (final concentrations). 'p120 blank' preparations used in some experiments were prepared in precise parallel to a normal p120 preparations except the starting cells were either infected with wild type baculo-virus, or were uninfected. The final fractions derived from these 'blank' preparations were pooled on a 'parallel volume' basis because they contained virtually no protein.

The p120 6× HIS tag contained a thrombin cleavage recognition motif. Careful titration with thrombin and analysis with 6% polyacrylamide SDS-gels revealed two thrombin sites, with similar sensitivities to thrombin, both close to the amino-terminal (because an αCOOH-terminal antibody still immunoprecipitated the twice-cut p120). One site was at the expected location for the site engineered into the tag; the other site was approximately 40-residues in from the amino-terminal (in a region with no favored thrombin recognition sequences). Under optimized conditions (2 U $ml^{-1}$, thrombin; 0.2 $mg \cdot ml^{-1}$ p120; 4 hours, 4° C., with 1 mM EGTA and 1 mM $MgCl_2$) it was possible to generate preparations of thrombin cleaved p120 which contained 15% uncut p120, 50% cut at the authentic amino-terminal thrombin site and 35% with an additional approximately 40 residues cleaved. In these experiments thrombin action was terminated by the addition of 100 nM N-acetyl D-Phe Pro-2-amido-5 guanidino butane boronic acid; a potent thrombin inhibitor (Sigma). Throughout this work, preparations of partially cleaved p120 were used parallel with totally uncleaved p120. It was clear that: (A) all three p120's bound to p101 with very similar affinity, (B) p101 bound to the p120 mixture was activated by Gβγs to a similar extent to p101 bound to uncleaved p120 and, (C) both the uncleaved and partially cleaved p120 s were virtually insensitive to Gβγ subunits in the absence of p101 (although complete thrombin cleavage tended to reduce overall p120 catalytic activity by 20–30% and increase the 1.7 fold apparent activation by Gβγ in the absence of p101 to about 2.5 fold).

(EE)-p101 was purified from frozen pellets of Sf9 cells as follows. Cells from 2 liters of infected Sf9 culture were sonicated into 50 mls of 0.12M NaCl; 1mM $MgCl_2$; 25 mM HEPES, pH 7.4, 4° C.; 1 mM EGTA plus antiproteases I as described above. After centrifugation (120, 000×g, 4° C., 40 minutes), the supernatant was removed (as described above), supplemented with 1% w/v, Triton X100, 0.4% sodium cholate, 0.4M NaCl (final concentrations), and mixed with 2 mls of packed protein G sepharose covalently cross-linked to an α-(myc) irrelevant, monoclonal antibody (washed in an equivalent solution). After 30 minutes mixing at 4° C., the beads were sedimented and the supernatant was removed and mixed with 1 ml of protein G Sepharose covalently cross-linked to an α-(EE) monoclonal antibody (equilibrated in an equivalent solution). After 2 hours mixing at 4° C. the beads were washed as described below for U937 cell α-(EE) immunoprecipitations, except (a) the washes were in a 20 ml centrifuge tube, and (b) the beads were finally washed 3× with buffer H, comprised of buffer G with 1k, w/v, Triton X-100. 'p101 blank' (p101C) preparations used in some experiments were prepared from either wild-type baculo-virus infected or uninfected cells exactly as described above.

p101/p120 heterodimers formed in vivo by co-infection of Sf9 cells with both forms of recombinant baculo-virus were purified as described for (EE)-p101 except the immunoprecipitates were washed 4× with buffer I, 1%, w/v, Triton X-100; 0.15M NaCl; 20 mM HEPES, pH 7.4, 4° C.; 1 mM EGTA; 2× with buffer J, comprised of buffer I supplemented with 0.4M NaCl (final concentration), then 3× with buffer G before being eluted with 1 bed volume of 150 μg ml$^{-1}$ (final concentration) of (EE)-peptide in buffer G. The (EE)-peptide, amino-terminal-acetylated EYMPTD, has a very high affinity for the α-(EE) monoclonal antibody. After the beads were incubated with (EE)-peptide, on ice, for 40 minutes, the supernatant was removed. Aliquots of the eluted proteins were diluted and assayed for PI3K activity (see above) or mixed with SDS sample buffer directly.

In in vitro reconstitution experiments, p120 preparations in buffer G supplemented with 1%, w/v, Triton X-100 (now equivalent to buffer H) were mixed with (EE)-p101 (10:1 molar ratio of protein) still bound to the protein G matrix, mixed for 2 hours (end on end at 4° C.), then washed and eluted with (EE)-peptide as described for the purification of p101/p120-PI3K reconstituted in vivo, in the Example below.

9.3 RESULTS

Single-step purifications utilizing the tags yielded purified protein preparations as assessed by Coomassie staining; their apparent sizes matched expectation. Further, both were correctly recognized in Western blots by specific, COOH Terminal directed and internal-sequence directed, antipeptide, rabbit polyclonal sera (not shown) indicating their authenticity.

p120 bound tightly, and in 1:1 molar stoichiometry, to p101 both (a) in vitro, when both proteins had been independently purified, mixed (with p101 still associated with the protein G matrix used to isolate it) then washed stringently before being eluted with (EE)-peptide or, (b) in vivo, when Sf9 cells were co-infected with both forms of rbv and proteins were purified via the p101 tag (data not shown).

Free, purified p120 was a PtdIns(4,5)P$_2$-selective, wortmannin-sensitive PI3K. Gβγs had a small and bi-modal effect on free p120 PI3K activity. An equimolar mixture (final total concentration of 2 μM) of Gα's o, $i_{1-2}$ and $i_3$ bound to GDP and in the presence of aluminum fluoride had no significant effect on free p120 PI3K activity (this was a preparation of Gαs which, when added in a 1.5 fold molar excess, could completely inhibit the effects of Gβγs, on PI3K). Tyrosine phosphorylated peptides able to activate p85/p110-PI3K family members also had no detectable effect on p120 PI3K activity. When bound to p101 (either in vivo or in vitro) p120's , PI3K activity could be activated greater than 100× by Gβγ subunits. Tyrosine phosphorylated peptides and Gβ-GDP/aluminum fluoride had no effect on Gβγ activated, or basal, p101/p120 PI3K activity. In the absence of Gβγs the specific activity of p120 in a p101/p120 complex is lower than the specific activity of free p120 but is increased greater than 50× in their presence (see FIG. 7).

Comparison of the specific catalytic activities of pig neutrophil-derived PI3K (B) and the Sf9-derived p101/p120 heterodimers, under identical, Gβγ-stimulated, assay conditions, showed the Sf9 derived material to have a 2× higher activity per mg protein. This result is not inconsistent with the likely 'age at assay' of a PI3K preparation derived from circulating neutrophils via a 4 day purification protocol and indicates the bulk of the recombinant PI3K is correctly folded and that any critical post-translational modifications must be in place.

10. EXAMPLE: Expression of p101 and p120 in mammalian cells

A family of mammalian expression vectors were constructed that enabled, amino-terminal epitope-tagged forms (either (myc) or (EE)) of p101 and p120 to be transiently expressed. This example describes the production of purified recombinant p101 and p120 fusion proteins from mammalian cells, and subsequent analysis of their properties.

10.1 MATERIALS AND METHODS 10.1.1 CELL CULTURE

U937 cells were grown in RPMI 1640 with 10%, v/v, heat-inactivated (HI)-FBS and diluted 4 fold every 2 days. Cos-7 cells were grown in DMEM 10% HI-FBS.

10.1.2 CONSTRUCTION OF EXPRESSION VECTORS

The use of N-terminal PCR and appropriate restriction sites allowed the p120 and p101 ORFs to be manipulated into a form where they could be inserted in frame into various expression vectors (in each case the first amino acid encoded after the N-terminal tag was the start methionine. The 3'-untranslated resin of the p120 cDNA was used in full and that of the p101 cDNA truncated at a BamHI site (nucleotide 192, FIG. 1). The vectors used for cytomegalovirus-driven (CMV) expression in mammalian cells were (A) pCMV(EE) (encoding an N-terminal MEEEEFMPMPMEF (SEQ ID NO:7) or MEEEEFMP-MEFSS (SEQ ID NO:8) 'EE-tag' for p101 or p120 expression, respectively) and (B) pCMV(myc) (encoding an N-terminal MEQKLISEEDLEF (SEQ ID NO:9) or MEQK-LISEEDLEFSS (SEQ ID NO:10) 'myc-tag' for p101 or p120 expression, respectively). All vectors were N-terminally sequenced before use.

10.1.3 U937 TRANSFECTION PROTOCOLS

Exponentially growing U937 cells (diluted 12 hours previously) were washed 2× with PBS and resuspended in sterile electroporation medium (EM) containing; 30 mM NaCl, 0.12M KCl, 8.1 mM Na$_2$HPO$_4$, 1.46 mM KH$_2$PO$_4$ and 5MM MgCl$_2$, at room temperature. Circular plasmid DNA was added in 1× EM to the cells to produce a 0.5 ml final volume containing 1.4×10$^7$ cells and 40 μg total DNA (usually made up to 40 μg with an expression plasmid with the same promoter and expressing a similarly tagged but irrelevant protein) and were transferred to a cuvette (0.4 cms gap, BioRad). After 15 minutes standing at room temperature the cells were electroporated (1 pulse at 280V and 960 μF, with a BioRad Gene pulser; time constants were typically 18 msec) then-placed on ice for a further 8 minutes before being diluted into 5 mls of RPMI, 10% HI-FBS. After standing for 5 minutes, to allow dead cells to clump together, the cells were diluted with 35 ml of RPMI, 10% HI-FES, supplemented with penicillin and streptomycin, then TPA and ZnCl$_2$ were added (both of which substantially amplify expression from CMV promoters in U937 cells) to final concentrations of 5×10$^{-8}$M and 200 μM, respectively. If the cells were to be labelled with [35S]-methionine (trans-label, ICN) then the RPMI used after the electroporation was methionine-, and leucine-free and contained 2 mM NaHCO$_3$ and 25 mM HEPES and 10% dialyzed HI-FBS and the cells resuspended in a final volume of 10 mls with 20 μCi/ml [3S]-methionine/leucine (phs TPA and ZnCl$_2$, as above)

After 12 hours (either with or without [35S]) the cell suspensions were mixed with di-isopropyl fluorophosphate (1 mM final concentration), left for 5 minutes, then collected by centrifugation, washed 1× with PBS, and lysed for immunoprecipitation. (EE)-epitope tagged proteins were immunoprecipitated from U937 cell lysates as follows. Cells from 1 electroporation were lysed into 1.25 mls of lysis buffer containing 1%, w/v, Triton X-100, 25 mM HEPES, pH 7.4, 4° C.; 1mM EGTA; 1 mM $MgCl_2$; 0.15 m NaCl and 0.1 mM PMSF, 10 μg $ml^{-1}$ leupeptin, 10 $\mu gml^{-1}$ aprotinin, 10 $\mu gml^{-1}$ antipain 10 $\mu gml^{-1}$ pepstatin A and 10 $\mu gml^{-1}$ of bestatin (henceforth known as antiproteases I). The lysates were centrifuged (12,000 rpm, 0° C., 15 minutes). The resulting supernatants was removed and mixed with 4M NaCl (0.1 ml), 20% sodium cholate (25 μl) and protein G sepharose (40 μl packed volume) covalently coupled to an irrelevant, isotype-matched, mouse monoclonal antibody (at approx. 5–10 mg-$ml^{-1}$ sepharose). The supernatants were mixed end over end for 20 minutes, then the beads were sedimented and the supernatant transferred to another tube with protein G sepharose beads (10 μl, packed) covalently crosslinked to α-(EE)-mouse monoclonal antibody (at approx. 5–10 mg-$ml^{-1}$ sepharose). After 2 hours mixing at 4° C. the immunoprecipitates were washed 5× with 1.0%, w/v, Triton X-100; 0.4% cholate; 0.004% SDS; 0.4M NaCl; 1 mM EGTA; 25 mM HEPES, pH 7.4, at 0° C.; 1× with 0.5M LiCl, 0.1M Tris, pH 8.0, 4° C.; 2× with 0.12M NaCl; 1 mM EGTA; 25 mM HEPES, pH 7.4, at 0° C. The last buffer wash was supplemented with 1 mM DTT (final wash buffer). If the immunoprecipitates were prepared from [3S]S-methionine labelled cells the last wash was omitted and the beads were boiled in SDS sample buffer. Otherwise, the samples were assayed for PI3K activity as described below.

10.1.4 COS-7 CELL TRANSFECTIONS

Exponentially growing Cos-7 cells were trypsinized/replated at about 50–70% confluence 3 hours prior to transfection. At the time of transfection they were again trypsinized, diluted into DMEM 10% FBS, counted, washed 2× in PBS and resuspended in EM ($1\times10^7$ per cuvette) mixed with circular plasmid DNA (40 μg total per cuvette, made up of combinations of 10 μg of EXV-(EE)-$\beta_1$, 10 μg of EXV-(myc)-$\tau_2$, 10 μg of pCMV-(myc)-p120 or 10–40 μg of an irrelevant mammalian expression vector), to give a final volume of 500 μl and then transferred to an electroporation cuvette (0.4 cms gap, BioRad). After 10 minutes at room temperature the cells were electroporated (250V, 960 μF), placed on ice for 8 minutes then diluted into DMEM 10% FBS. Aggregated cells were allowed to clump and were avoided as the cells were aliquoted into 6 cm dishes (four from each cuvette).

After 48 hours, the four dishes from each treatment were washed into HEPES-buffered DMEM containing 1 mM $NaHCO_3$ and 0.2% fatty acid-free BSA. After 10 hours two replicate dishes were harvested for Western blotting (with α-(myc) monoclonal antibody as the 1° detection reagent, α-mouse-HRP as the 2° detection system and quantitation by ECL and densiometric scanning). Two dishes were washed into phosphate-free, DMEM, with 1 mM $NaHCO_3$ and 0.2% fatty acid-free BSA, then incubated for a further 90 minutes at 37° C. with 300 μCi [$^{32}$P]-Pi per dish (in 4 mls). Media was aspirated and 1 ml of ice-cold 1M HCl was added. The cells were scraped, removed and the dishes washed with 1.33 mls of methanol. The HCl and methanol washes were pooled with 2.66 mls of chloroform (to yield a 'Folch' two phase, solvent distribution) mixed and centrifuged. The lower phases were removed and mixed with 1.95 mls of fresh upper phase (see above) containing 0.5 mM EDTA and 1 mM tetrabutylammonium sulphate. After mixing and centrifugation, the lower phases were removed, dried down, deacylated and prepared for analysis by anion-exchange HPLC (Stephens et al., 1991, Nature. Lond. 351:33–39, the disclosure of which is incorporated herein by reference in its entirety).

10.2 RESULTS

When transiently expressed in U937 cells, (EE)-p101 and (EE)-p120 could be specifically immunoprecipitated from [35S]-methionine labelled cells in approximately equal amounts (allowing for their relative compliment of methionines; 8:25 respectively, data not shown). Stringently washed α-(EE)-p101 immunoprecipitates contained a wortmannin-sensitive, PtdIns(4,5)$P_2$-selective, Gβγ-sensitive PI3K activity that was absent in controls using either an irrelevant monoclonal antibody for the immunoprecipitation, or a cDNA encoding an (EE)-tagged irrelevant protein which was expressed, as judged by [$^{35}$S]-methionine labelling, to similar levels as (EE)-p101.

The activation by Gβγτs could be blocked by preincubation with a 2 fold molar excess of Gα-GDP. Further, the PI3K activity in these p101 immunoprecipitates was insensitive to Gα-GDP/aluminum fluoride. Co-transfection of (myc)-p120 with (EE)-p101 did not increase the PI3K activity specifically recovered in α-(EE) immunoprecipitates. Indeed it decreased, probably because the expression of (EE)-p101 was relatively lower in the presence of (myc)-p120 expression vectors. In contrast, cells transfected with (EE)-p120 α-(EE)-immunoprecipitates contained barely detectable PI3K activity either in the presence or absence of Gβγs. These cells contained comparable moles of [$^{35}$S]-methionine labelled p120 as there was (EE)-p101 in α-(EE)-immunoprecipitates from (EE)-p101 transfected cells. Co-transfection with (myc)-p101 resulted in a substantial increase in, specifically, the Gβγτ-stimulated PI3K activity that could be recovered, despite a fall in the expression of (EE)-p120 (as judged by [35S]-methionine labelling) (see FIG. 8). This data indicates that U937 cells (human) contain an endogenous PI3K catalytic subunit that can bind to a transiently expressed p101 (pig). When bound to p101 (pig) that endogenous catalytic subunit displays substantial regulation by Gβγs because all of the p120 present in the immunoprecipitates is bound to p101.

In contrast, in α-(EE) immunoprecipitates from (EE)-p120 transfected cells much of the p120 is unassociated with p101 and hence relatively inactive (compared to that bound to p101 and in the presence of Gβγs). However, this PI3K activity, when assayed in the presence of Gβγs, is substantially amplified by co-transfection with (myc)-p101. The alternative explanation for these data—that the p120 is 'denatured' (although soluble and capable of being immunoprecipitated) unless expressed in the presence of p101—is unlikely in view of the data obtained with independently Sf9-purified, derived proteins.

To test whether the p101/p120 PI3K could be activated by Gβγs and produce PtdIns(3,4,5)$P_3$ in vivo, we transiently expressed various combinations of (myc)-$\gamma_2$, (EE)-$\beta_1$, (myc)-p101 and (myc)-p120 in Cos-7 cells and measured their effects on the levels of [35P]-phosphoinositides in cells 48 hours after transfection (see FIG. 9). p120 only produced significant increases in PtdIns(3,4,5)$P_3$ and PtdIns(3, 4)$P_2$ in a $\beta_1\gamma_2$-dependent fashion in the presence of p101. This pattern of results could not be explained by changes in the relative expression of the different cDNAs when introduced in combinations (see FIG. 9).

11. DEPOSIT OF CLONES

The following microorganisms or clones were deposited with the American Type Culture Collection (ATCC), Rockville, Md., on the dates indicated and were assigned the indicated accession number:

| Clone | ATCC Access. No. | Date of Deposit |
|---|---|---|
| pCMV3mycp101 | 97636 | June 27, 1996 |
| pCMV3mycp120 | 97637 | June 27, 1996 |

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. An isolated p101 regulatory subunit polypeptide having the amino acid sequence shown in SEQ ID NO:2, or the amino acid sequence encoded by the cDNA contained in the cDNA clone pCMV3mycp101 as deposited with the ATCC having accession No. 97636.

2. A chimeric protein comprising a p101 regulatory subunit polypeptide having the amino acid sequence shown in SEQ ID NO:2, or the amino acid sequence encoded by the cDNA contained in the cDNA clone pCMV3mycp101 as deposited with the ATCC having accession NO. 97636, fused to a heterologous polypeptide.

3. The chimeric protein of claim 2 in which the heterologous polypeptide is a Glu tag or a myc epitope tag.

4. An isolated p101 regulatory subunit polypeptide encoded by a nucleic acid molecule having a nucleotide sequence that;
   a) encodes the amino acid sequence shown in SEQ ID NO:2 or the amino acid sequence encoded by the cDNA contained in the cDNA clone pCMV3mycp101 as deposited with the ATCC having accession No. 97636; or
   b) hybridizes under highly stringent conditions to the nucleotide sequence of (a) or to its complement.

5. A chimeric protein comprising a p101 regulatory subunit polypeptide encoded by a nucleic acid molecule having a nucleotide sequence that:
   a) encodes the amino acid sequence shown in SEQ ID NO:2 or the amino acid sequence encoded by the cDNA contained in the cDNA clone pCMV3mycp101 as deposited with the ATCC having accession No. 97636; or
   b) hybridizes under highly stringent conditions to the nucleotide sequence of (a) or to its complement, fused to a heterologous polypeptide.

6. The chimeric protein of claim 5 in which the heterologous polypeptide is a Glu tag or a myc epitope tag.

7. An isolated p101 regulatory subunit polypeptide encoded by a nucleic acid molecule having a nucleotide sequence that:
   a) is the sequence shown in SEQ ID NO:1 or the cDNA contained in the cDNA clone pCMV3mycp101 as deposited with the ATCC having accession No. 97636; or b) hybridizes under highly stringent conditions to the nucleotide sequence of (a) or to its complement.

8. A chimeric protein comprising a p101 regulatory subunit polypeptide encoded by a nucleic acid molecule having a nucleotide sequence that:
   a) is the sequence shown in SEQ ID NO:1 or the cDNA contained in the cDNA clone pCMV3mycp101 as deposited with the ATCC having accession No. 97636; or
   b) hybridizes under highly stringent conditions to the nucleotide sequence of (a) or to its complement, fused to a heterologous polypeptide.

9. The chimeric protein of claim 8 in which the heterologous polypeptide is a Glu tag or a myc epitope tag.

10. The isolated p101 regulatory subunit polypeptide of claim 4 further comprising a p120 catalytic subunit polypeptide.

11. The isolated p101 regulatory subunit polypeptide of claim 7 further comprising a p120 catalytic subunit polypeptide.

12. The isolated p101 regulatory subunit polypeptide of claim 1 further comprising a p120 catalytic subunit polypeptide.

13. An isolated p101 regulatory subunit, or a fragment thereof, comprising an amino acid sequence selected from the group consisting of amino acid residues 1–732 of SEQ ID NO:2, amino acid residues 733–877 of SEQ ID NO:2, amino acid residues 1–160 of SEQ ID NO:2, amino acid residues 161–263 of SEQ ID NO:2, amino acid residues 161–877 of SEQ ID NO:2, and amino acid residues 1–160 and 264–877 of SEQ ID NO:2.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 4692 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO:1:

```
CCGTGCGCCC  CTCAAGACTA  ATGGACCCCC  GGCTCAGGAA  TCGCACGAGG  CAGGCTCACA      60
CCCGAGGCCC  ATGGAAGTTC  CCAGGCCAGG  GGTCAAGTTG  GAACCGAAGC  TGCTGCCAGC     120
TTACACCACA  GCCACAGCAA  CTTGGGATCT  GAGCTGCATC  TGTGACCTAC  ACCACAGCTC     180
ACGGCAATGC  TGGATTCCCA  ACACACCAAG  TGGGGCCAGG  GATCGAACCC  GCATCCTCTT     240
GGACAGTAGT  CAGATTCATT  ACCACTGAGC  CATTGACAGG  AACTCCAGGG  GCAGGGGGA     300
GTCTCTTGTT  TTTGGCTCCT  CCCGACACCT  GGTGAAATGG  ACCAGCGCAG  GCACCCCTTT     360
CCAGTGGCTG  TCCCAGGCGA  TGACTCAGGA  TGCAGCCAGG  GGCCACGACG  TGCACGGAGG     420
ACCGCATCCA  GCACGCCCTG  GAGCGCTGCT  TGCACGGGCT  CAGCCTCAGC  CGCCGCTCCA     480
CCTCCTGGTC  AGCTGGGCTG  TGTCTAAACT  GTTGGAGCCT  GCAGGAGCTG  GTCAGCAGGG     540
ATCCGGGCCA  CTTCCTTATC  CTCCTGGAGC  AGATCCTGCA  GAAACCCGA   GAGGTCCAAG     600
AGAAGGGCAC  CTATGACCTC  CTCGCGCCCC  TGGCCCTGCT  CTTCTATTCT  ACTGTCCTCT     660
GTACGCCACA  CTTCCCGCCA  GACTCAGATC  TCCTTCTGAA  AGCAGCCAGA  ACCTACCACC     720
GATTCCTGAC  CTGGCCGGTT  CCGTACTGCA  GCATCTGCCA  GGAACTGCTC  ACCTTCATCG     780
ATGCTGAGCT  GAAGGCCCCA  GGAATCTCCT  ACCAGCGACT  GGTGAGGGCG  GAGCAGGGCC     840
TGTCCACAAG  GAGTCACCGC  AGCTCCACCG  TCACGGTGCT  CTTGGTGAAC  CCCGTGGAGG     900
TGCAGGCTGA  GTTCCTTGAC  GTGGCCGACA  AGCTGAGCAC  ACCAGGGCCC  TCGCCGCACA     960
GCGCCTACAT  CACCCTGCTC  CTGCATGCCT  TCCAGGCCAC  CTTTGGGGCC  CACTGTGACC    1020
TCTCTGGTCT  GCACCGCAGG  TTGCAGTCCA  AGACCCTGGC  AGAGCTCGAG  GCCATCTTCA    1080
CGGAGACAGC  CGAGGCACAG  GAGCTGGCCT  CAGGCATCGG  GGATGCAGCT  GAGGCCCGGC    1140
AGTGGCTCAG  GACCAAGCTG  CAGGCGGTGG  GAGAGAAGGC  CGGCTTCCCT  GGTGTCTTAG    1200
ACACCGCCAA  ACCTGGCAAG  CTCCGCACCA  TCCCCATCCC  GGTCGCCAGG  TGCTACACCT    1260
ACAGCTGGAA  CCAGGACAGC  TTCGACATCC  TGCAGGAAAT  CCTGCTCAAG  GAGCAGGAGC    1320
```

```
TGCTCCAGCC AGAGATCCTG GACGACGAGG AGGACGAGGA CGAGGAGGAC GAGGAAGAGG    1380

ACTTGGACGC CGACGGCCAC TGCGCGGAGA GGGACTCCGT GCTCTCCACC GGCTCGGCGG    1440

CCTCCCACGC CTCCACGCTG TCCCTGGCCT CGTCCCAGGC CTCGGGGCCC ACGCTCTCCC    1500

GCCAGTTGCT GACCTCCTTC GTCTCGGGCC TCTCGGATGG CGTGGACAGC GGCTACATGG    1560

AGGACATCGA GGAGAGCGCC TACGAGCGGC CCCGGAGGCC TGGCGGCCAC GAGCGCCGGG    1620

GCCACCGCCG GCCCGGGCAG AAGTTCAACA GGATCTATAA ACTCTTCAAG AGCACCAGCC    1680

AGATGGTGCT GCGGAGGGAC TCGCGCAGCC TGGAGGGCAG CCCGGACAGC GGCCCGCCCC    1740

TGCGTCGGGC CGGCAGCCTC TGCAGCCCCC TGGACAGCCC GACCCTGCCC CCGTCCCGGG    1800

CCCAGGGCTC CCGCTCGCTG CCCCAGCCCA AGCTCAGCCC CCAGCTGCCC GGCTGGCTCC    1860

TGGCCCCCGC CTCCCGCCAC CAGCGCCGCC GCCCCTTCCT GAGCGGGGAC GAGGACCCCA    1920

AGGCTTCCAC GCTGCGTGTC GTGGTCTTCG GCTCGGATCG GATCTCGGGG AAGGTGGTCC    1980

GGGCTTACAG CAACCTGCGG CGGCTGGAGA ACAACCGTCC TCTCCTCACA CGGTTCTTCA    2040

AGCTACAGTT CTTCTACGTG CCTGTCAAGC GGAGCCGTGG GACAGGCACC CCCACCAGCC    2100

CAGCCCCTCG GAGCCAGACG CCCCCCCTCC CCACAGACGC CCCGAGGCAC CCGGGCCCTG    2160

CAGAGCTGGG CGCCGCCCCC TGGGAGGAGA GCACCAATGA CATCTCCCAC TACCTCGGCA    2220

TGCTCGACCC CTGGTACGAG CGAAACGTCC TGGGCCTCAT GCACCTGCCT CCTGAAGTCC    2280

TGTGCCAGTC CCTGAAGGCT GAGCCCCGGC CCCTGGAGGG CTCCCCTGCC CAGCTGCCCA    2340

TCCTGGCGGA CATGCTGCTC TACTACTGCC GCTTCGCTGC CCGGCCGGTG CTGCTGCAGG    2400

TCTATCAGAC CGAGCTGACC TTCATCACCG GGAGAAGAC GACGGAGATC TTCATCCACT    2460

CCCTGGAGCT GGGCCACTCT GCTGCCACAC GTGCCATCAA GGCTTCGGGT CCTGGCAGCA    2520

AGCGGCTGGG CATCGATGGT GACCGGGAGG CCGTCCCTCT AACACTACAG ATAATTTACA    2580

GCAAGGGGGC CATCAGCGGC CGGAGTCGCT GGAGCAACAT GGAAAAGCTC TGCACCTCTG    2640

TCAACCTCAG CAAGGCCTGC CGGCAGCAGG AGGAGCTAGA CTCCAGCACA GAGGCCCTGA    2700

CGCTAAACCT GACAGAAGTG GTGAAAAGAC AGACCCCTAA ATCCAAGAAG GGCTTTAACC    2760

AGATCAGCAC CTCGCAGATC AAAGTGGACA AGGTGCAGAT CATCGGCTCT AACAGCTGCC    2820

CCTTTGCCGT GTGTCTGGAC CAGGACGAGA GGAAGATCCT GCAGAGTGTC ATCAGGTGCG    2880

AGGTCTCGCC CTGCTACAAG CCTGAGAAGA GCAGCCTCTG CCCCCCACCC CAGAGGCCCT    2940

CCTACCCGCC AGCGCCGGCC ACGCCCGACC TCTGCTCCCT GCTCTGCCTG CCCATCATGA    3000

CTTTCAGCGG AGCTCTGCCC TAGCCGCCAC CCTGCACCAG CCTGGACAGG GAGCCGGGGG    3060

GCAGCCTCCT CGGAGCCCCC TCCCCAGAAG ACTGGCGGCT GAGAGGGTCG TGCTCCCTGT    3120

GGAGAACAGA GGGGCCGTGT ACTGGGTCAG GGTCCCGCTG TGGGCCCTGC AGCAGCAAGA    3180

GCGGGGGCTG CTGGGGCCTC AGGGCTCTGT TTGGGCGAGA AGCAGGCATT AGGGAGAGGG    3240

GCCTGGCCCC ACGGCTCTCA GCTTCCTCAC GGTAGCGGAG AGAGGGATGG GTGAGCTTGA    3300

CCTCAAGGCC CTGGCCTCCA GTGGGGGTCC AGGATCCTTT CTGGAAGGAA GATCCCAAGG    3360

CGCTGGTGCT CTGGGGTGTG GTGTTAGGGG CTCCCCCCCC AGCCCTGGGC CAGGGCCCCC    3420

CCGTTACTTT GTCAGAGACT TGGGGATCCT GTGTCTGGAG GGTCAAGTCC CCTCCCTGG    3480

GGGTTCAAGC AGTGGAAGTA TGGTTGCGAC TTTTCTGACG TTGGTGCAAT CCCCGCCCCC    3540

ACCTCAACCC CCCCACAAAA AAACCCCTTC TCTCTTTCAA GTTCCCTGGG TCTTCTGTGA    3600

AACAGCACTA ACACTTGACC TGGCTGTGCC AGCACTTGGA ACAGATGCTC CCTGGATCGA    3660

GAGCCTTGGG AGACAGGACA AGCTTAGGTT CGGTGGTGGC TCAGTTACCT TCTAGCGAAA    3720
```

|  |  |  |  |  |  |
|---|---|---|---|---|---|
| TGAGCAGAAG | GAGGTGAATT | GGCTCCTTCG | AGGCTCCCCT | ACCTGGGCAC | TAAGATGGGG | 3780 |
| GGAATAAGGC | CGCCTTAAAG | GGTTGGGGTG | ATGTCGTCTG | CAAAGCGCCT | GGCCCAGTGG | 3840 |
| CCGGCTGGTA | GCAAGGTGCG | GCCTCACCCT | CTGGGCGTCG | ACTCCTCGT | GTGGCGGGAG | 3900 |
| GCTAAAAGGA | TGCCCTGCCC | CCGTGATGCT | GTCATTCCCT | CCTTCCAATT | CACTGATGAG | 3960 |
| GCAGGACCCA | GACTGAGGGG | GTGAGGGGCG | CACAGTTCTA | CCTTTGAAGG | AGGAAGTGCC | 4020 |
| TTGATCAGAG | TAAGAGGAGG | GTGGCCCAGG | CGCCCCAAC | CGCCCCTCC | TCCTCTCCCA | 4080 |
| GGTTGGCCCC | TGTGCCTCCC | ACTCCATCT | CACTCCTTGG | GCTGGCGCAC | ATCACGGGCA | 4140 |
| CAGTCCTCCA | GCCCCACAGT | TCACTGGTAC | CATGGCCCCT | GGGTCGGTTC | GCAGAGGATG | 4200 |
| GAGGATAAGA | CTTGCCTCGA | GAACTTGGGT | CTGATGGGA | AACCGGGTGA | TGGAAATGAT | 4260 |
| TCCGGAAGAT | TAAAACCTCC | CAGGTTCAAG | TGTCGGAGAA | CCGCCCCAC | AACCGGACTA | 4320 |
| GGTTGGTAGG | GAGAGGGCAG | GGCTTGGGCC | CGGGATTTGG | ACTAGGAGAG | GCGGGGGGAG | 4380 |
| GTAACCAGAG | AAGCAAGACA | GTTGTATCCC | CGCAAAAGAC | CCTTCCCCGC | CCCTCCCCTC | 4440 |
| CTGCTCTGGC | TCCATCTGCT | TCAAAGGGTC | TGGGCTTTAG | GAGCCCGTGG | TGCCCAGCGC | 4500 |
| AGCGTACTCA | GGACTCGAGA | GACGCGGACC | GTGCCAGTTC | CCACCCTGTG | CCACTCCAGG | 4560 |
| CCCCAGGGAG | GGGTTTGCAA | TATACCCTCA | ACGTTTTTGT | GTGTGTGGTA | AGGTCGTCCT | 4620 |
| AGGACCCCAA | ATGGAATTTA | ACGTTATTGT | CAAATAAAAC | TTGATTTGTC | TTGGAAAAAA | 4680 |
| AAAAAAAAAA | AA |  |  |  |  | 4692 |

(2) INFORMATION FOR SEQ ID NO:2:

(i) SEQUENCE CHARACTERISTICS:
        (A) LENGTH: 877 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:2:

```
Met Gln Pro Gly Ala Thr Thr Cys Thr Glu Asp Arg Ile Gln His Ala
 1               5                  10                  15

Leu Glu Arg Cys Leu His Gly Leu Ser Leu Ser Arg Arg Ser Thr Ser
             20                  25                  30

Trp Ser Ala Gly Leu Cys Leu Asn Cys Trp Ser Leu Gln Glu Leu Val
         35                  40                  45

Ser Arg Asp Pro Gly His Phe Leu Ile Leu Leu Glu Gln Ile Leu Gln
     50                  55                  60

Lys Thr Arg Glu Val Gln Glu Lys Gly Thr Tyr Asp Leu Leu Ala Pro
 65                  70                  75                  80

Leu Ala Leu Leu Phe Tyr Ser Thr Val Leu Cys Thr Pro His Phe Pro
                 85                  90                  95

Pro Asp Ser Asp Leu Leu Leu Lys Ala Ala Arg Thr Tyr His Arg Phe
            100                 105                 110

Leu Thr Trp Pro Val Pro Tyr Cys Ser Ile Cys Gln Glu Leu Leu Thr
        115                 120                 125

Phe Ile Asp Ala Glu Leu Lys Ala Pro Gly Ile Ser Tyr Gln Arg Leu
    130                 135                 140

Val Arg Ala Glu Gln Gly Leu Ser Thr Arg Ser His Arg Ser Ser Thr
145                 150                 155                 160

Val Thr Val Leu Leu Val Asn Pro Val Glu Val Gln Ala Glu Phe Leu
                165                 170                 175
```

```
Asp  Val  Ala  Asp  Lys  Leu  Ser  Thr  Pro  Gly  Pro  Ser  Pro  His  Ser  Ala
               180                 185                      190

Tyr  Ile  Thr  Leu  Leu  Leu  His  Ala  Phe  Gln  Ala  Thr  Phe  Gly  Ala  His
          195                 200                 205

Cys  Asp  Leu  Ser  Gly  Leu  His  Arg  Arg  Leu  Gln  Ser  Lys  Thr  Leu  Ala
     210                      215                 220

Glu  Leu  Glu  Ala  Ile  Phe  Thr  Glu  Thr  Ala  Glu  Ala  Gln  Glu  Leu  Ala
225                      230                 235                           240

Ser  Gly  Ile  Gly  Asp  Ala  Ala  Glu  Ala  Arg  Gln  Trp  Leu  Arg  Thr  Lys
                    245                      250                 255

Leu  Gln  Ala  Val  Gly  Glu  Lys  Ala  Gly  Phe  Pro  Gly  Val  Leu  Asp  Thr
               260                 265                      270

Ala  Lys  Pro  Gly  Lys  Leu  Arg  Thr  Ile  Pro  Ile  Pro  Val  Ala  Arg  Cys
          275                      280                 285

Tyr  Thr  Tyr  Ser  Trp  Asn  Gln  Asp  Ser  Phe  Asp  Ile  Leu  Gln  Glu  Ile
     290                 295                      300

Leu  Leu  Lys  Glu  Gln  Glu  Leu  Leu  Gln  Pro  Glu  Ile  Leu  Asp  Asp  Glu
305                 310                 315                           320

Glu  Asp  Glu  Asp  Glu  Asp  Glu  Glu  Glu  Asp  Leu  Asp  Ala  Asp  Gly
                    325                 330                           335

His  Cys  Ala  Glu  Arg  Asp  Ser  Val  Leu  Ser  Thr  Gly  Ser  Ala  Ala  Ser
               340                 345                      350

His  Ala  Ser  Thr  Leu  Ser  Leu  Ala  Ser  Ser  Gln  Ala  Ser  Gly  Pro  Thr
          355                 360                      365

Leu  Ser  Arg  Gln  Leu  Leu  Thr  Ser  Phe  Val  Ser  Gly  Leu  Ser  Asp  Gly
     370                      375                 380

Val  Asp  Ser  Gly  Tyr  Met  Glu  Asp  Ile  Glu  Glu  Ser  Ala  Tyr  Glu  Arg
385                      390                 395                           400

Pro  Arg  Arg  Pro  Gly  Gly  His  Glu  Arg  Arg  Gly  His  Arg  Arg  Pro  Gly
                    405                      410                 415

Gln  Lys  Phe  Asn  Arg  Ile  Tyr  Lys  Leu  Phe  Lys  Ser  Thr  Ser  Gln  Met
               420                 425                      430

Val  Leu  Arg  Arg  Asp  Ser  Arg  Ser  Leu  Glu  Gly  Ser  Pro  Asp  Ser  Gly
          435                      440                 445

Pro  Pro  Leu  Arg  Arg  Ala  Gly  Ser  Leu  Cys  Ser  Pro  Leu  Asp  Ser  Pro
450                      455                      460

Thr  Leu  Pro  Pro  Ser  Arg  Ala  Gln  Gly  Ser  Arg  Ser  Leu  Pro  Gln  Pro
465                 470                      475                           480

Lys  Leu  Ser  Pro  Gln  Leu  Pro  Gly  Trp  Leu  Leu  Ala  Pro  Ala  Ser  Arg
                    485                 490                      495

His  Gln  Arg  Arg  Arg  Pro  Phe  Leu  Ser  Gly  Asp  Glu  Asp  Pro  Lys  Ala
               500                 505                      510

Ser  Thr  Leu  Arg  Val  Val  Val  Phe  Gly  Ser  Asp  Arg  Ile  Ser  Gly  Lys
          515                      520                 525

Val  Val  Arg  Ala  Tyr  Ser  Asn  Leu  Arg  Arg  Leu  Glu  Asn  Asn  Arg  Pro
     530                 535                      540

Leu  Leu  Thr  Arg  Phe  Phe  Lys  Leu  Gln  Phe  Phe  Tyr  Val  Pro  Val  Lys
545                 550                      555                           560

Arg  Ser  Arg  Gly  Thr  Gly  Thr  Pro  Thr  Ser  Pro  Ala  Pro  Arg  Ser  Gln
                    565                 570                      575

Thr  Pro  Pro  Leu  Pro  Thr  Asp  Ala  Pro  Arg  His  Pro  Gly  Pro  Ala  Glu
               580                 585                      590

Leu  Gly  Ala  Ala  Pro  Trp  Glu  Glu  Ser  Thr  Asn  Asp  Ile  Ser  His  Tyr
```

-continued

|  |  |  | 595 |  |  |  |  | 600 |  |  |  |  | 605 |  |
|---|---|---|---|---|---|---|---|---|---|---|---|---|---|---|
| Leu | Gly | Met | Leu | Asp | Pro | Trp | Tyr | Glu | Arg | Asn | Val | Gly | Leu | Met |
|  | 610 |  |  |  |  | 615 |  |  |  |  | 620 |  |  |  |
| His | Leu | Pro | Pro | Glu | Val | Leu | Cys | Gln | Ser | Leu | Lys | Ala | Glu | Pro | Arg |
| 625 |  |  |  |  | 630 |  |  |  |  | 635 |  |  |  |  | 640 |
| Pro | Leu | Glu | Gly | Ser | Pro | Ala | Gln | Leu | Pro | Ile | Leu | Ala | Asp | Met | Leu |
|  |  |  |  | 645 |  |  |  |  | 650 |  |  |  |  | 655 |  |
| Leu | Tyr | Tyr | Cys | Arg | Phe | Ala | Ala | Arg | Pro | Val | Leu | Leu | Gln | Val | Tyr |
|  |  |  | 660 |  |  |  |  | 665 |  |  |  |  | 670 |  |  |
| Gln | Thr | Glu | Leu | Thr | Phe | Ile | Thr | Gly | Glu | Lys | Thr | Thr | Glu | Ile | Phe |
|  |  | 675 |  |  |  |  | 680 |  |  |  |  | 685 |  |  |  |
| Ile | His | Ser | Leu | Glu | Leu | Gly | His | Ser | Ala | Ala | Thr | Arg | Ala | Ile | Lys |
|  | 690 |  |  |  |  | 695 |  |  |  |  | 700 |  |  |  |  |
| Ala | Ser | Gly | Pro | Gly | Ser | Lys | Arg | Leu | Gly | Ile | Asp | Gly | Asp | Arg | Glu |
| 705 |  |  |  |  | 710 |  |  |  |  | 715 |  |  |  |  | 720 |
| Ala | Val | Pro | Leu | Thr | Leu | Gln | Ile | Ile | Tyr | Ser | Lys | Gly | Ala | Ile | Ser |
|  |  |  |  | 725 |  |  |  |  | 730 |  |  |  |  | 735 |  |
| Gly | Arg | Ser | Arg | Trp | Ser | Asn | Met | Glu | Lys | Leu | Cys | Thr | Ser | Val | Asn |
|  |  |  | 740 |  |  |  |  | 745 |  |  |  |  | 750 |  |  |
| Leu | Ser | Lys | Ala | Cys | Arg | Gln | Gln | Glu | Glu | Leu | Asp | Ser | Ser | Thr | Glu |
|  |  | 755 |  |  |  |  | 760 |  |  |  |  | 765 |  |  |  |
| Ala | Leu | Thr | Leu | Asn | Leu | Thr | Glu | Val | Val | Lys | Arg | Gln | Thr | Pro | Lys |
|  | 770 |  |  |  |  | 775 |  |  |  |  | 780 |  |  |  |  |
| Ser | Lys | Lys | Gly | Phe | Asn | Gln | Ile | Ser | Thr | Ser | Gln | Ile | Lys | Val | Asp |
| 785 |  |  |  |  | 790 |  |  |  |  | 795 |  |  |  |  | 800 |
| Lys | Val | Gln | Ile | Ile | Gly | Ser | Asn | Ser | Cys | Pro | Phe | Ala | Val | Cys | Leu |
|  |  |  |  | 805 |  |  |  |  | 810 |  |  |  |  | 815 |  |
| Asp | Gln | Asp | Glu | Arg | Lys | Ile | Leu | Gln | Ser | Val | Ile | Arg | Cys | Glu | Val |
|  |  |  | 820 |  |  |  |  | 825 |  |  |  |  | 830 |  |  |
| Ser | Pro | Cys | Tyr | Lys | Pro | Glu | Lys | Ser | Ser | Leu | Cys | Pro | Pro | Pro | Gln |
|  |  | 835 |  |  |  |  | 840 |  |  |  |  | 845 |  |  |  |
| Arg | Pro | Ser | Tyr | Pro | Pro | Ala | Pro | Ala | Thr | Pro | Asp | Leu | Cys | Ser | Leu |
|  | 850 |  |  |  |  | 855 |  |  |  |  | 860 |  |  |  |  |
| Leu | Cys | Leu | Pro | Ile | Met | Thr | Phe | Ser | Gly | Ala | Leu | Pro |  |  |  |
| 865 |  |  |  |  | 870 |  |  |  |  | 875 |  |  |  |  |  |

( 2 ) INFORMATION FOR SEQ ID NO:3:

( i ) SEQUENCE CHARACTERISTICS:
        ( A ) LENGTH: 3808 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO:3:

| GGCACGAGGA | ATTTGTTTTG | TTTTCAGAAA | TTAAACAAAT | GATCCTTCAG | CATCATCACC | 60 |
| TCCGCTGCTT | TATCAGGTCG | CATAGGGCAT | GGAGCTGGAG | AACTATGAAC | AGCCCGTGGT | 120 |
| GCTGAGAGAG | GACAACCGCC | GCAGGCGTCG | GAGGATGAAG | CCGCGCAGCA | CGGCAGCCAG | 180 |
| CCTGTCCTCC | ATGGAGCTCA | TCCCCATCGA | GTTTGTTTTG | CCACCAGCC | AGCGCAACAC | 240 |
| CAAGACCCCC | GAAACGGCAC | TGCTGCACGT | GGCCGGCCAC | GGCAATGTGG | AGAAGATGAA | 300 |
| GGCCCAGGTG | TTGTTGCGCG | CGCTGGAGAC | GAGCGTTTCT | TGGGACTTCT | ACCACCGGTT | 360 |
| CGGCCCCGAC | CACTTCCTCC | TGGTCTTCCA | GAAGAAGGGG | GAGTGGTACG | AGATCTATGA | 420 |

-continued

| | | | | | |
|---|---|---|---|---|---|
|CAAGTACCAG|GTGGTGCAGA|CCCTGGACTG|CCTGCGCTAC|TGGGAGGTGT|TGCACCGCAG 480|
|CCCCGGGCAG|ATCCACGTGG|TCCAGCGGCA|CGCGCCCTCG|GAGGAGACAT|TGGCCTTCCA 540|
|GCGCCAGCTC|AACGCCCTCA|TCGGCTACGA|CGTCACCGAC|GTCAGCAACG|TGCATGACGA 600|
|TGAGCTGGAG|TTCACGCGGC|GCCGCCTGGT|CACCCCGCGC|ATGGCCGAGG|TGGCCGGCCG 660|
|CGACCCCAAG|CTTTACGCCA|TGCACCCCTG|GGTGACATCC|AAGCCCCTCC|CTGAGTACCT 720|
|TCTGAAGAAG|ATCACTAACA|ACTGCGTCTT|CATCGTCATT|CACCGCAGCA|CCACCAGCCA 780|
|GACCATCAAG|GTCTCGGCCG|ATGACACCCC|AGGCACCATC|CTCCAGAGCT|TCTTTACCAA 840|
|GATGGCCAAG|AAGAAATCTC|TGATGGATAT|CCCTGAAAGC|CAGAACGAAC|GGGACTTTGT 900|
|GCTGCGCGTC|TGCGGCCGGG|ATGAGTACCT|GGTGGGTGAG|ACGCCCATCA|AAAATTTCCA 960|
|GTGGGTGAGG|CAGTGCCTCA|AGAATGGGGA|GGAGATTCAC|CTTGTGCTGG|ACACTCCTCC 1020|
|AGACCCAGCC|CTGGACGAGG|TGAGGAAGGA|AGAGTGGCCG|CTGGTGGATG|ACTGCACGGG 1080|
|AGTCACTGGC|TACCACGAGC|AGCTGACCAT|CCACGGCAAG|GACCATGAAA|GTGTGTTCAC 1140|
|CGTGTCCCTG|TGGGACTGTG|ACCGCAAGTT|CAGGGTCAAA|ATCAGAGGCA|TTGATATCCC 1200|
|TGTCCTGCCC|CGGACCGCTG|ACCTCACGGT|GTTTGTGGAG|GCAAACATCC|AGTATGGGCA 1260|
|GCAAGTCCTT|TGCCAAAGGA|GAACCAGCCC|CAAACCCTTC|ACGGAGGAGG|TGCTCTGGAA 1320|
|CGTGTGGCTT|GAGTTCAGTA|TTAAAATCAA|AGACTTACCC|AAAGGGGCTC|TGCTGAACCT 1380|
|CCAGATCTAC|TGCGGCAAAG|CTCCAGCACT|GTCTGGCAAG|ACCTCTGCAG|AGATGCCCAG 1440|
|TCCCGAGTCC|AAAGGCAAAG|CTCAGCTTCT|GTACTATGTC|AACCTATTGC|TGATAGACCA 1500|
|CCGCTTCCTC|CTGCGCCATG|GCGAGTATGT|GCTCCACATG|TGGCAGTTAT|CCGGGAAGGG 1560|
|GGAAGACCAA|GGGAGCTTCA|ATGCCGACAA|GCTCACGTCG|GAACCAACC|CGGACAAGGA 1620|
|GGACTCAATG|TCCATCTCCA|TTCTTCTGGA|CAATTACTGC|CACCCCATAG|CCTTGCCTAA 1680|
|GCATCGGCCT|ACCCCTGACC|CAGAAGGGGA|CCGGGTTCGG|GCAGAAATGC|CCAATCAGCT 1740|
|TCGGAAGCAA|CTGGAGGCAA|TCATAGCCAC|GGATCCGCTT|AACCCACTCA|CAGCTGAAGA 1800|
|CAAAGAACTG|CTCTGGCATT|TCAGATATGA|AAGCCTGAAG|GATCCCAAAG|CGTATCCTAA 1860|
|GCTCTTTAGC|TCGGTGAAAT|GGGGACAGCA|AGAAATTGTG|GCCAAAACAT|ACCAATTATT 1920|
|AGCCAAAAGG|GAGGTCTGGG|ATCAGAGTGC|TTTGGATGTG|GGGTTAACCA|TGCAGCTCCT 1980|
|GGACTGCAAC|TTCTCGGATG|AAAACGTGAG|AGCCATTGCA|GTCCAGAAAC|TGGAGAGCTT 2040|
|GGAGGATGAT|GACGTGCTCC|ATTACCTGCT|CCAGCTGGTC|CAGGCTGTGA|AATTTGAACC 2100|
|ATACCATGAC|AGTGCCCTAG|CCAGATTTCT|GCTGAAGCGT|GGTTTAAGAA|ACAAGAGAAT 2160|
|TGGTCACTTC|TTGTTTTGGT|TCTTGAGAAG|TGAGATTGCC|CAGTCTAGGC|ACTATCAGCA 2220|
|GAGGTTTGCA|GTGATCCTGG|AAGCCTACCT|GAGGGGCTGT|GGCACAGCCA|TGCTGCACGA 2280|
|CTTCACCCAG|CAAGTCCAAG|TAATTGACAT|GTTACAAAAA|GTCACCATTG|ACATTAAATC 2340|
|GCTCTCTGCT|GAAAAGTATG|ACGTCAGTTC|CCAAGTTATT|TCCCAACTTA|AGCAAAAGCT 2400|
|TGAAAACCTA|CAGAATTTGA|ATCTCCCCCA|AAGCTTTAGA|GTTCCCTATG|ATCCTGGACT 2460|
|GAAAGCCGGG|GCACTGGTGA|TCGAAAAATG|TAAAGTGATG|GCCTCCAAGA|AGAAGCCCCT 2520|
|GTGGCTTGAG|TTTAAATGTG|CCGATCCTAC|GGCTCTATCA|AATGAAACAA|TTGGAATTAT 2580|
|CTTTAAACAC|GGTGACGATC|TGCGCCAAGA|CATGCTTATT|TTACAGATTC|TACGAATCAT 2640|
|GGAGTCCATT|TGGGAGACCG|AATCTTTGGA|TCTGTGCCTC|CTGCCATATG|GCTGCATTTC 2700|
|AACTGGTGAC|AAAATAGGAA|TGATCGAGAT|CGTGAAGGAC|GCCACGACAA|TCGCCAAAAT 2760|
|TCAGCAAAGC|ACAGTGGGCA|ACACGGGTGC|CTTTAAAGAT|GAAGTCCTGA|GTCACTGGCT 2820|

```
CAAAGAAAAA  TGCCCTATTG  AAGAAAAGTT  TCAGGCAGCT  GTGGAGAGAT  TTGTTTATTC   2880
CTGTGCCGGC  TACTGTGTGG  CAACCTTTGT  TCTCGGAATA  GGCGACAGAC  ACAATGACAA   2940
TATTATGATC  TCAGAAACAG  GAAATCTATT  TCATATTGAT  TTCGGACACA  TTCTTGGGAA   3000
TTACAAAAGT  TTCCTGGGCA  TTAATAAAGA  GAGGGTGCCA  TTTGTGCTAA  CCCCAGACTT   3060
CCTGTTTGTG  ATGGGGACTT  CTGGAAAGAA  GACAAGTCTA  CACTTCCAGA  AATTTCAGGA   3120
TGTCTGCGTC  AAGGCTTACC  TAGCCCTTCG  TCATCACACA  AACCTACTGA  TCATCCTCTT   3180
CTCCATGATG  CTGATGACAG  GAATGCCCCA  GTTAACCAGC  AAAGAAGACA  TTGAATACAT   3240
TCGGGATGCC  CTCACAGTGG  GCAAAAGTGA  GGAGGATGCT  AAAAAGTATT  TTCTGGATCA   3300
GATTGAAGTT  TGCAGAGACA  AAGGATGGAC  CGTGCAGTTT  AACTGGTTCT  TACATCTTGT   3360
TCTTGGCATC  AAACAAGGGG  AGAAGCATCC  CGCATAAAAC  TTTGGGCCAA  GAGTTAAAAC   3420
CCAAGTTATT  GTCCTAATGC  TTTACGTCAG  CAGGACAATC  ACCGAACTTG  ATGTCATGTA   3480
GTGGGACATT  ATGAAAGCTG  GCACTTGAGA  AATATAGCTC  TTCCCCTAAC  TGAACTCTTC   3540
ACTGGAGAAA  AACCTTGGCA  TGTTTAAGTA  ATGTTCAGTG  TTAGGCTTAT  TTGCATGTTT   3600
GTTTTTTCTC  ATGTGCCCCC  TCAGTCATGT  TGGAGACTGT  TCTAAATTTA  AGTGGCCTAA   3660
TGACCTCTGA  AGTTTCAACT  TTCTTGGTAC  TGAGTGCTTC  TGAAATTCTT  TACAATAATT   3720
GGTAACATCT  ATTGTCAGCT  GGGTATCCTC  TCAATTTTGG  TTATCCTTGG  GTTTCTCAAA   3780
CTCCTTACAG  GAAAAAAAAA  AAAAAAA                                         3808
```

(2) INFORMATION FOR SEQ ID NO:4:

(i) SEQUENCE CHARACTERISTICS:
        (A) LENGTH: 1102 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:4:

```
Met  Glu  Leu  Glu  Asn  Tyr  Glu  Gln  Pro  Val  Val  Leu  Arg  Glu  Asp  Asn
 1              5                        10                       15
Arg  Arg  Arg  Arg  Arg  Arg  Met  Lys  Pro  Arg  Ser  Thr  Ala  Ala  Ser  Leu
            20                       25                       30
Ser  Ser  Met  Glu  Leu  Ile  Pro  Ile  Glu  Phe  Val  Leu  Ala  Thr  Ser  Gln
       35                       40                       45
Arg  Asn  Thr  Lys  Thr  Pro  Glu  Thr  Ala  Leu  Leu  His  Val  Ala  Gly  His
       50                       55                       60
Gly  Asn  Val  Glu  Lys  Met  Lys  Ala  Gln  Val  Leu  Leu  Arg  Ala  Leu  Glu
 65                      70                       75                       80
Thr  Ser  Val  Ser  Trp  Asp  Phe  Tyr  His  Arg  Phe  Gly  Pro  Asp  His  Phe
                 85                       90                       95
Leu  Leu  Val  Phe  Gln  Lys  Lys  Gly  Glu  Trp  Tyr  Glu  Ile  Tyr  Asp  Lys
                100                      105                      110
Tyr  Gln  Val  Val  Gln  Thr  Leu  Asp  Cys  Leu  Arg  Tyr  Trp  Glu  Val  Leu
            115                      120                      125
His  Arg  Ser  Pro  Gly  Gln  Ile  His  Val  Val  Gln  Arg  His  Ala  Pro  Ser
       130                      135                      140
Glu  Glu  Thr  Leu  Ala  Phe  Gln  Arg  Gln  Leu  Asn  Ala  Leu  Ile  Gly  Tyr
145                      150                      155                      160
Asp  Val  Thr  Asp  Val  Ser  Asn  Val  His  Asp  Asp  Glu  Leu  Glu  Phe  Thr
                165                      170                      175
```

-continued

| | | | | | | | | | | | | | | |
|---|---|---|---|---|---|---|---|---|---|---|---|---|---|---|
| Arg | Arg | Arg | Leu 180 | Val | Thr | Pro | Arg 185 | Met | Ala | Glu | Val | Ala | Gly 190 | Arg | Asp |
| Pro | Lys | Leu 195 | Tyr | Ala | Met | His | Pro 200 | Trp | Val | Thr | Ser 205 | Lys | Pro | Leu | Pro |
| Glu | Tyr 210 | Leu | Leu | Lys | Lys | Ile 215 | Thr | Asn | Asn | Cys | Val 220 | Phe | Ile | Val | Ile |
| His 225 | Arg | Ser | Thr | Thr | Ser 230 | Gln | Thr | Ile | Lys | Val 235 | Ser | Ala | Asp | Asp | Thr 240 |
| Pro | Gly | Thr | Ile | Leu 245 | Gln | Ser | Phe | Phe | Thr 250 | Lys | Met | Ala | Lys | Lys 255 | Lys |
| Ser | Leu | Met | Asp 260 | Ile | Pro | Glu | Ser | Gln 265 | Asn | Glu | Arg | Asp | Phe 270 | Val | Leu |
| Arg | Val | Cys 275 | Gly | Arg | Asp | Glu | Tyr 280 | Leu | Val | Gly | Glu | Thr 285 | Pro | Ile | Lys |
| Asn | Phe 290 | Gln | Trp | Val | Arg | Gln 295 | Cys | Leu | Lys | Asn | Gly 300 | Glu | Glu | Ile | His |
| Leu 305 | Val | Leu | Asp | Thr | Pro 310 | Pro | Asp | Pro | Ala | Leu 315 | Asp | Glu | Val | Arg | Lys 320 |
| Glu | Glu | Trp | Pro | Leu 325 | Val | Asp | Asp | Cys | Thr 330 | Gly | Val | Thr | Gly | Tyr 335 | His |
| Glu | Gln | Leu | Thr 340 | Ile | His | Gly | Lys | Asp 345 | His | Glu | Ser | Val | Phe 350 | Thr | Val |
| Ser | Leu | Trp 355 | Asp | Cys | Asp | Arg | Lys 360 | Phe | Arg | Val | Lys | Ile 365 | Arg | Gly | Ile |
| Asp | Ile 370 | Pro | Val | Leu | Pro | Arg 375 | Thr | Ala | Asp | Leu | Thr 380 | Val | Phe | Val | Glu |
| Ala 385 | Asn | Ile | Gln | Tyr | Gly 390 | Gln | Gln | Val | Leu | Cys 395 | Gln | Arg | Arg | Thr | Ser 400 |
| Pro | Lys | Pro | Phe | Thr 405 | Glu | Glu | Val | Leu | Trp 410 | Asn | Val | Trp | Leu | Glu 415 | Phe |
| Ser | Ile | Lys | Ile 420 | Lys | Asp | Leu | Pro | Lys 425 | Gly | Ala | Leu | Leu | Asn 430 | Leu | Gln |
| Ile | Tyr | Cys 435 | Gly | Lys | Ala | Pro | Ala 440 | Leu | Ser | Gly | Lys | Thr 445 | Ser | Ala | Glu |
| Met | Pro | Ser 450 | Pro | Glu | Ser | Lys 455 | Gly | Lys | Ala | Gln | Leu 460 | Leu | Tyr | Tyr | Val |
| Asn 465 | Leu | Leu | Leu | Ile | Asp 470 | His | Arg | Phe | Leu | Leu 475 | Arg | His | Gly | Glu | Tyr 480 |
| Val | Leu | His | Met | Trp 485 | Gln | Leu | Ser | Gly | Lys 490 | Gly | Glu | Asp | Gln | Gly 495 | Ser |
| Phe | Asn | Ala | Asp 500 | Lys | Leu | Thr | Ser | Gly 505 | Thr | Asn | Pro | Asp | Lys 510 | Glu | Asp |
| Ser | Met | Ser 515 | Ile | Ser | Ile | Leu | Leu 520 | Asp | Asn | Tyr | Cys | His 525 | Pro | Ile | Ala |
| Leu | Pro 530 | Lys | His | Arg | Pro | Thr 535 | Pro | Asp | Pro | Glu | Gly 540 | Asp | Arg | Val | Arg |
| Ala 545 | Glu | Met | Pro | Asn | Gln 550 | Leu | Arg | Lys | Gln | Leu 555 | Glu | Ala | Ile | Ile | Ala 560 |
| Thr | Asp | Pro | Leu | Asn 565 | Pro | Leu | Thr | Ala | Glu 570 | Asp | Lys | Glu | Leu | Leu 575 | Trp |
| His | Phe | Arg | Tyr 580 | Glu | Ser | Leu | Lys | Asp 585 | Pro | Lys | Ala | Tyr | Pro 590 | Lys | Leu |
| Phe | Ser | Ser 595 | Val | Lys | Trp | Gly | Gln 600 | Gln | Glu | Ile | Val | Ala 605 | Lys | Thr | Tyr |

-continued

| | | | | | | | | | | | | | | |
|---|---|---|---|---|---|---|---|---|---|---|---|---|---|---|
| Gln | Leu | Leu | Ala | Lys | Arg | Glu | Val | Trp | Asp | Gln | Ser | Ala | Leu | Asp | Val |
| | 610 | | | | 615 | | | | | 620 | | | | |
| Gly | Leu | Thr | Met | Gln | Leu | Leu | Asp | Cys | Asn | Phe | Ser | Asp | Glu | Asn | Val |
| 625 | | | | 630 | | | | | 635 | | | | | 640 |
| Arg | Ala | Ile | Ala | Val | Gln | Lys | Leu | Glu | Ser | Leu | Glu | Asp | Asp | Val |
| | | | 645 | | | | 650 | | | | | 655 | |
| Leu | His | Tyr | Leu | Leu | Gln | Leu | Val | Gln | Ala | Val | Lys | Phe | Glu | Pro | Tyr |
| | | | 660 | | | | | 665 | | | | | 670 | | |
| His | Asp | Ser | Ala | Leu | Ala | Arg | Phe | Leu | Leu | Lys | Arg | Gly | Leu | Arg | Asn |
| | | 675 | | | | | 680 | | | | | 685 | | | |
| Lys | Arg | Ile | Gly | His | Phe | Leu | Phe | Trp | Phe | Leu | Arg | Ser | Glu | Ile | Ala |
| | 690 | | | | 695 | | | | | 700 | | | | |
| Gln | Ser | Arg | His | Tyr | Gln | Gln | Arg | Phe | Ala | Val | Ile | Leu | Glu | Ala | Tyr |
| 705 | | | | 710 | | | | | 715 | | | | | 720 |
| Leu | Arg | Gly | Cys | Gly | Thr | Ala | Met | Leu | His | Asp | Phe | Thr | Gln | Gln | Val |
| | | | | 725 | | | | | 730 | | | | | 735 |
| Gln | Val | Ile | Asp | Met | Leu | Gln | Lys | Val | Thr | Ile | Asp | Ile | Lys | Ser | Leu |
| | | | 740 | | | | | 745 | | | | | 750 | | |
| Ser | Ala | Glu | Lys | Tyr | Asp | Val | Ser | Ser | Gln | Val | Ile | Ser | Gln | Leu | Lys |
| | | 755 | | | | | 760 | | | | | 765 | | | |
| Gln | Lys | Leu | Glu | Asn | Leu | Gln | Asn | Leu | Asn | Leu | Pro | Gln | Ser | Phe | Arg |
| | 770 | | | | | 775 | | | | | 780 | | | | |
| Val | Pro | Tyr | Asp | Pro | Gly | Leu | Lys | Ala | Gly | Ala | Leu | Val | Ile | Glu | Lys |
| 785 | | | | | 790 | | | | | 795 | | | | | 800 |
| Cys | Lys | Val | Met | Ala | Ser | Lys | Lys | Lys | Pro | Leu | Trp | Leu | Glu | Phe | Lys |
| | | | | 805 | | | | | 810 | | | | | 815 |
| Cys | Ala | Asp | Pro | Thr | Ala | Leu | Ser | Asn | Glu | Thr | Ile | Gly | Ile | Ile | Phe |
| | | | 820 | | | | | 825 | | | | | 830 | | |
| Lys | His | Gly | Asp | Asp | Leu | Arg | Gln | Asp | Met | Leu | Ile | Leu | Gln | Ile | Leu |
| | | 835 | | | | | 840 | | | | | 845 | | | |
| Arg | Ile | Met | Glu | Ser | Ile | Trp | Glu | Thr | Glu | Ser | Leu | Asp | Leu | Cys | Leu |
| | 850 | | | | 855 | | | | | 860 | | | | |
| Leu | Pro | Tyr | Gly | Cys | Ile | Ser | Thr | Gly | Asp | Lys | Ile | Gly | Met | Ile | Glu |
| 865 | | | | | 870 | | | | | 875 | | | | | 880 |
| Ile | Val | Lys | Asp | Ala | Thr | Thr | Ile | Ala | Lys | Ile | Gln | Gln | Ser | Thr | Val |
| | | | | 885 | | | | | 890 | | | | | 895 |
| Gly | Asn | Thr | Gly | Ala | Phe | Lys | Asp | Glu | Val | Leu | Ser | His | Trp | Leu | Lys |
| | | | 900 | | | | | 905 | | | | | 910 | | |
| Glu | Lys | Cys | Pro | Ile | Glu | Glu | Lys | Phe | Gln | Ala | Ala | Val | Glu | Arg | Phe |
| | | 915 | | | | | 920 | | | | | 925 | | | |
| Val | Tyr | Ser | Cys | Ala | Gly | Tyr | Cys | Val | Ala | Thr | Phe | Val | Leu | Gly | Ile |
| | 930 | | | | 935 | | | | | 940 | | | | |
| Gly | Asp | Arg | His | Asn | Asp | Asn | Ile | Met | Ile | Ser | Glu | Thr | Gly | Asn | Leu |
| 945 | | | | | 950 | | | | | 955 | | | | | 960 |
| Phe | His | Ile | Asp | Phe | Gly | His | Ile | Leu | Gly | Asn | Tyr | Lys | Ser | Phe | Leu |
| | | | | 965 | | | | | 970 | | | | | 975 |
| Gly | Ile | Asn | Lys | Glu | Arg | Val | Pro | Phe | Val | Leu | Thr | Pro | Asp | Phe | Leu |
| | | | 980 | | | | | 985 | | | | | 990 | | |
| Phe | Val | Met | Gly | Thr | Ser | Gly | Lys | Lys | Thr | Ser | Leu | His | Phe | Gln | Lys |
| | | 995 | | | | | 1000 | | | | | 1005 | | | |
| Phe | Gln | Asp | Val | Cys | Val | Lys | Ala | Tyr | Leu | Ala | Leu | Arg | His | His | Thr |
| | 1010 | | | | 1015 | | | | | 1020 | | | | |
| Asn | Leu | Leu | Ile | Ile | Leu | Phe | Ser | Met | Met | Leu | Met | Thr | Gly | Met | Pro |

|      | 1025 |      |      |      | 1030 |      |      |      | 1035 |      |      |      | 1040 |
|------|------|------|------|------|------|------|------|------|------|------|------|------|------|

Gln Leu Thr Ser Lys Glu Asp Ile Glu Tyr Ile Arg Asp Ala Leu Thr
              1045                    1050                    1055

Val Gly Lys Ser Glu Glu Asp Ala Lys Lys Tyr Phe Leu Asp Gln Ile
              1060                    1065                    1070

Glu Val Cys Arg Asp Lys Gly Trp Thr Val Gln Phe Asn Trp Phe Leu
              1075                    1080                    1085

His Leu Val Leu Gly Ile Lys Gln Gly Glu Lys His Pro Ala
              1090                    1095                    1100

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: unknown ( i i ) MOLECULE TYPE: DNA (genomic)

( i x ) FEATURE:
        ( A ) NAME/KEY: misc_feature
        ( B ) LOCATION: 12
        ( D ) OTHER INFORMATION: /note= "N is Inosine."

( i x ) FEATURE:
        ( A ) NAME/KEY: misc_feature
        ( B ) LOCATION: 21
        ( D ) OTHER INFORMATION: /note= "N is Inosine."

( i x ) FEATURE:
        ( A ) NAME/KEY: misc_feature
        ( B ) LOCATION: 27
        ( D ) OTHER INFORMATION: /note= "N is Inosine."

( x i ) SEQUENCE DESCRIPTION: SEQ ID NO:5:

CAYGAYTTYA CNCARCARGT NCARGTNATH GAYATG                                                          3 6

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: unknown ( i i ) MOLECULE TYPE: DNA (genomic)

( i x ) FEATURE:
        ( A ) NAME/KEY: misc_feature
        ( B ) LOCATION: 3
        ( D ) OTHER INFORMATION: /note= "N is Inosine."

( i x ) FEATURE:
        ( A ) NAME/KEY: misc_feature
        ( B ) LOCATION: 18
        ( D ) OTHER INFORMATION: /note= "N is Inosine."

( x i ) SEQUENCE DESCRIPTION: SEQ ID NO:6:

GCNTAYATGG ARGAYATNGA RGA                                                                        2 3

( 2 ) INFORMATION FOR SEQ ID NO:7:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: unknown ( i i ) MOLECULE TYPE: peptide -continued (xi) SEQUENCE DESCRIPTION: SEQ ID NO:7:

Met Glu Glu Glu Glu Phe Met Pro Met Pro Met Glu Phe
1               5                   10

(2) INFORMATION FOR SEQ ID NO:8:

(i) SEQUENCE CHARACTERISTICS:
      (A) LENGTH: 13 amino acids
      (B) TYPE: amino acid
      (C) STRANDEDNESS:
      (D) TOPOLOGY: unknown (ii) MOLECULE TYPE: peptide (xi) SEQUENCE DESCRIPTION: SEQ ID NO:8:

Met Glu Glu Glu Glu Phe Met Pro Met Glu Phe Ser Ser
1               5                   10

(2) INFORMATION FOR SEQ ID NO:9:

(i) SEQUENCE CHARACTERISTICS:
      (A) LENGTH: 13 amino acids
      (B) TYPE: amino acid
      (C) STRANDEDNESS:
      (D) TOPOLOGY: unknown (ii) MOLECULE TYPE: peptide (xi) SEQUENCE DESCRIPTION: SEQ ID NO:9:

Met Glu Gln Lys Leu Ile Ser Glu Glu Asp Leu Glu Phe
1               5                   10

(2) INFORMATION FOR SEQ ID NO:10:

(i) SEQUENCE CHARACTERISTICS:
      (A) LENGTH: 15 amino acids
      (B) TYPE: amino acid
      (C) STRANDEDNESS:
      (D) TOPOLOGY: unknown (ii) MOLECULE TYPE: peptide (xi) SEQUENCE DESCRIPTION: SEQ ID NO:10:

Met Glu Gln Lys Leu Ile Ser Glu Glu Asp Leu Glu Phe Ser Ser
1               5                   10                  15